US008835376B2

(12) United States Patent
Shen et al.

(10) Patent No.: US 8,835,376 B2
(45) Date of Patent: Sep. 16, 2014

(54) PROCESS FOR MAKING PARTICLES FOR DELIVERY OF DRUG NANOPARTICLES

(75) Inventors: Zhigang Shen, Singapore (SG); Jimmy Sung Lai Yun, Singapore (SG); Jun Hu, Singapore (SG); Nital Arvind Jugade, Singapore (SG); Jiyao Zhang, Singapore (SG); Wenhao Chen, Singapore (SG); Zhe Wang, Singapore (SG); Lingyan Gao, Singapore (SG); William Glover, New South Wales (AU); Jian Feng Chen, Beijing (CN)

(73) Assignee: Nanomaterials Technology Pte Ltd, Singapore (SG)

( * ) Notice: Subject to any disclaimer, the term of this patent is extended or adjusted under 35 U.S.C. 154(b) by 325 days.

(21) Appl. No.: 13/120,146

(22) PCT Filed: Sep. 24, 2009

(86) PCT No.: PCT/SG2009/000353
§ 371 (c)(1),
(2), (4) Date: Aug. 26, 2011

(87) PCT Pub. No.: WO2010/036211
PCT Pub. Date: Apr. 1, 2010

(65) Prior Publication Data
US 2011/0306539 A1   Dec. 15, 2011

Related U.S. Application Data

(60) Provisional application No. 61/100,133, filed on Sep. 25, 2008.

(30) Foreign Application Priority Data

May 29, 2009 (GB) .................................. 0909154.7

(51) Int. Cl.
| | | |
|---|---|---|
| A61K 38/02 | (2006.01) | |
| A61K 31/216 | (2006.01) | |
| A61K 31/513 | (2006.01) | |
| A61K 31/546 | (2006.01) | |
| A61K 38/13 | (2006.01) | |
| A61K 31/357 | (2006.01) | |
| A61K 31/57 | (2006.01) | |
| A61K 31/7052 | (2006.01) | |
| A61K 31/277 | (2006.01) | |
| A61K 31/197 | (2006.01) | |
| A61K 47/38 | (2006.01) | |
| A61K 47/24 | (2006.01) | |
| B01J 2/06 | (2006.01) | |
| A61K 9/16 | (2006.01) | |
| A61K 9/20 | (2006.01) | |
| A61K 9/14 | (2006.01) | |
| B01J 19/00 | (2006.01) | |

(52) U.S. Cl.
CPC ... *A61K 9/14* (2013.01); *B01J 2/06* (2013.01); *A61K 9/1652* (2013.01); *A61K 9/2077* (2013.01); *B01J 2219/00788* (2013.01); *B01J 2219/00889* (2013.01); *A61K 9/1694* (2013.01); *B01J 19/0093* (2013.01); *A61K 9/1623* (2013.01)
USPC ............ 514/1.1; 514/169; 514/545; 514/274; 514/202; 514/20.5; 514/452; 514/178; 514/29; 514/522; 514/567; 514/781; 514/772; 514/777; 514/772.5

(58) Field of Classification Search
None
See application file for complete search history.

(56) References Cited

U.S. PATENT DOCUMENTS

| | | | | |
|---|---|---|---|---|
| 5,989,583 | A  * | 11/1999 | Amselem ...................... | 424/439 |
| 2003/0096013 | A1 * | 5/2003 | Werling et al. ............... | 424/489 |
| 2003/0152500 | A1 * | 8/2003 | Dalziel et al. .............. | 422/245.1 |
| 2007/0148252 | A1 * | 6/2007 | Shaw et al. ................... | 424/489 |
| 2009/0297565 | A1 | 12/2009 | Müller et al. | |

FOREIGN PATENT DOCUMENTS

| | | | |
|---|---|---|---|
| CA | 2062303 | A1 | 3/1993 |
| CN | 1765487 | A | 6/2006 |
| CN | 1973827 | A | 6/2007 |
| CN | 101199482 | A | 6/2008 |
| JP | 05-05882 | A | 9/1993 |
| WO | WO 2005/041970 | A1 | 5/2005 |
| WO | 2008/057048 | A1 | 5/2008 |
| WO | WO 2009/020434 | A1 | 2/2009 |

OTHER PUBLICATIONS

Azithromycin. European Pharmacopoeia 5.0. p. 1039-1040. 2005.*
Hu et al. Drug Development and Industrial Pharmacy. 30(3); 233-245:2004.*

(Continued)

*Primary Examiner* — Karlheinz R Skowronek
*Assistant Examiner* — Schuyler Milton
(74) *Attorney, Agent, or Firm* — Kilpatrick Townsend & Stockton LLP

(57) ABSTRACT

A process for making particles for delivery of drug nanoparticles is disclosed herein. The process comprises the steps of (a) forming a suspension of drug nanoparticles by mixing a precipitant solution with an anti-solvent solution under micro-mixing environment, where the formed nanoparticles have a narrow particle size distribution; (b) providing an excipient to at least one of the precipitant solution, the anti-solvent solution and the suspension of drug nanoparticles, the excipient being selected to maintain said drug nanoparticles in a dispersed state when in liquid form; and (c) drying the suspension of drug nanoparticles containing the excipient therein to remove solvent therefrom, wherein removal of the solvent causes the excipient to solidify and thereby form micro-sized matrix particles, each micro-sized particle being comprised of drug nanoparticles dispersed in a solid matrix of the excipient.

15 Claims, 24 Drawing Sheets

(56) References Cited

OTHER PUBLICATIONS

Luo, Guangsheng, et al., "Advance in micro-mixing devices and property research thereof", Modern Chemical Industry, 2003, p. 10-13, vol. 23, No. 8, [English Abstract].

First Office Action for Chinese Patent Application No. 200980137850.3, mailed on Apr. 24, 2012. [English Translation].

International Search Report for PCT/SG2009/000353, dated Dec. 18, 2009.

Westmeier et al., "Combination Particles Containing Salmeterol Xinafoate and Fluticasone Propionate: Formulation and Aerodynamic Assessment," Journal of Pharmaceutical Sciences 97(6): 2299-2310 (1997).

* cited by examiner

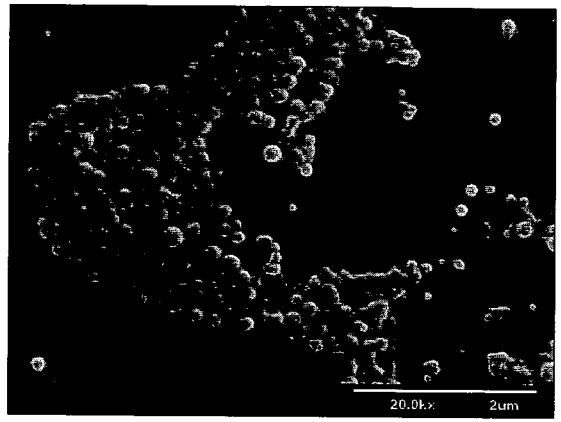 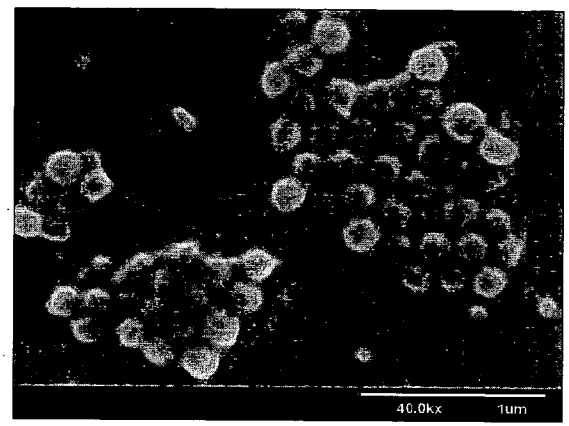
Fig. 23a  Fig. 23b
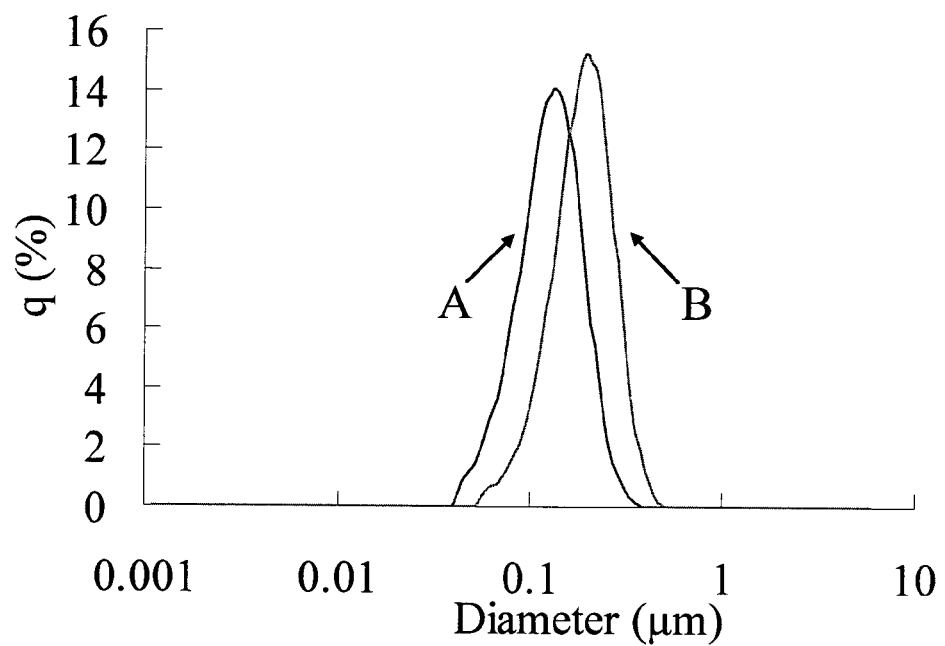
Fig. 24

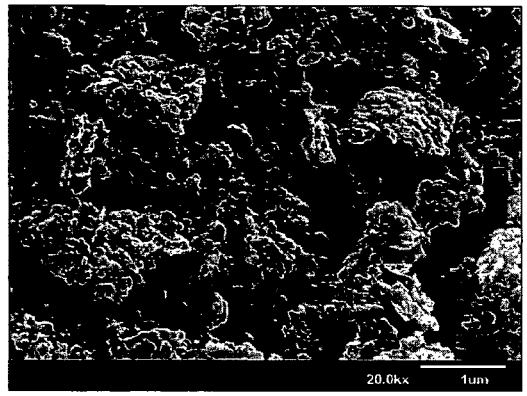 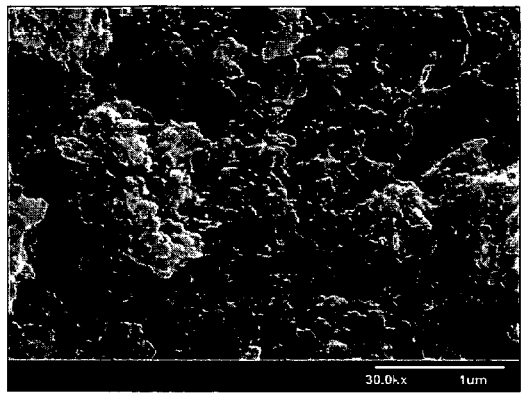
Fig. 31a　　　　　　　　　　　　　　Fig. 31b
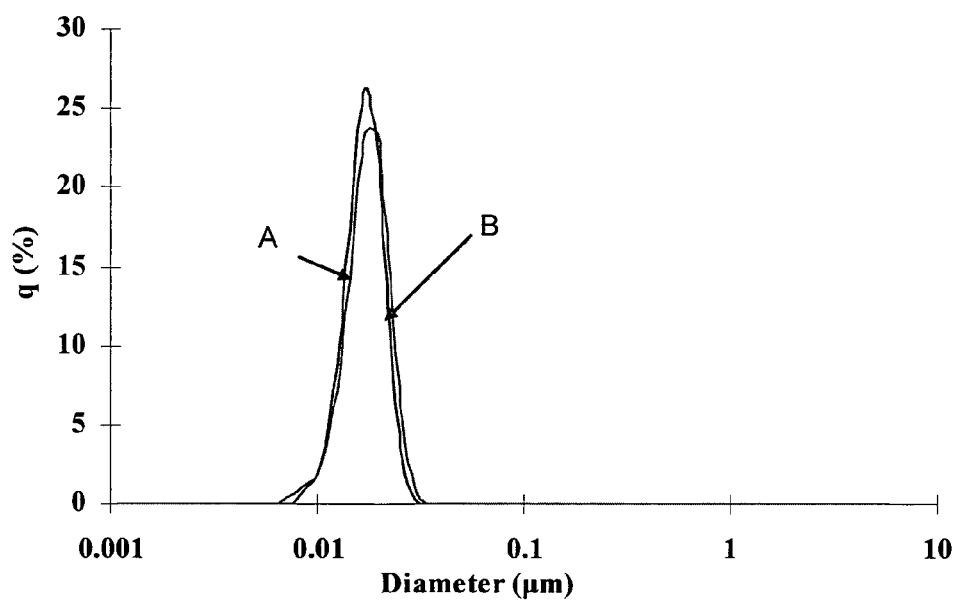
Fig. 32a

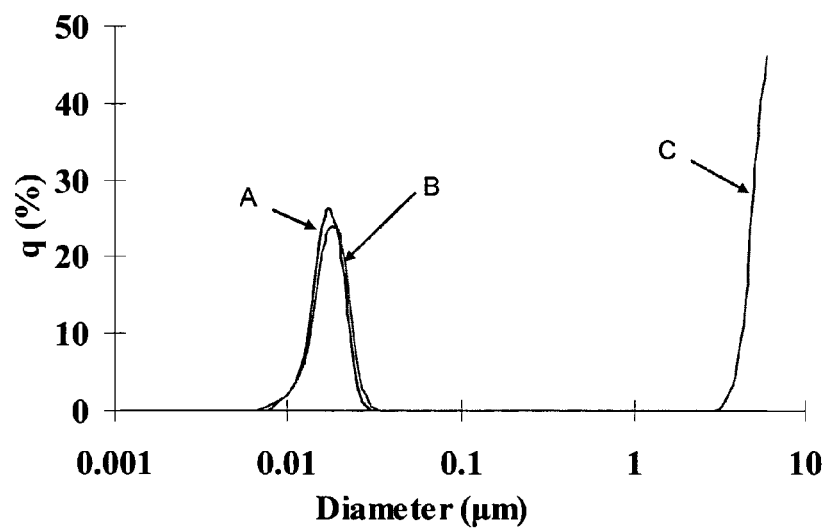
Fig. 32b
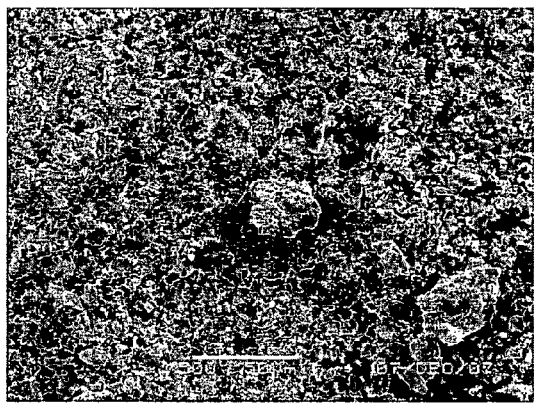 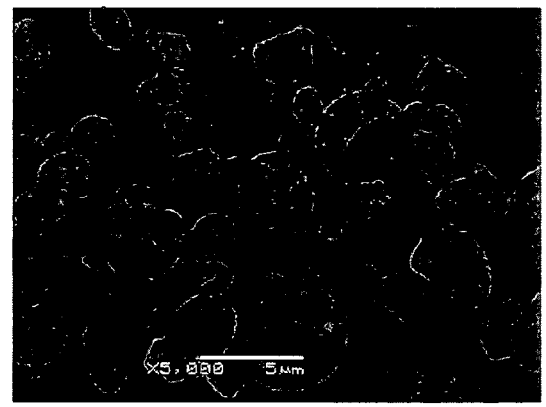
Fig. 33a                Fig. 33b

US 8,835,376 B2

PROCESS FOR MAKING PARTICLES FOR DELIVERY OF DRUG NANOPARTICLES

TECHNICAL FIELD

The present invention generally relates to a process for making particles for delivery of drug nanoparticles. This process may be generally suitable for mass-producing drug nanoparticles on an industrial scale.

BACKGROUND

Synthetic or natural drugs aim to serve as remedies or preventive agents for illnesses and can be administered into the body by methods such as injection or ingestion. In comparing the various routes of drug administration available, ingestion or oral administration is preferred as it is less painful and has a higher rate of patient compliance. It is also a more convenient and simple or uncomplicated method as compared to injection.

More often than not, many poorly water-soluble drugs are the keys to treatment for many diseases. Thus, it is an arduous task and challenge for scientists to formulate a method for the generation of these drugs to improve their solubility within the human body. Further, water-insoluble drugs have low bioavailability. Ultimately, it would be ideal for drugs to have as high a level of bioavailability in the body as possible. However, when a poorly water-soluble drug is consumed orally, its bioavailability in vivo may be compromised due to incomplete absorption and first-pass metabolism in a patient's stomach. Hence, its medicinal purpose would not be as effective when consumed. As a result, it is desirable to maximize the bioavailability of drugs in vivo.

In recent years, research has been undertaken to develop alternate processes to generate nanoparticulate drugs in a bid to rectify the problem of poorly water-soluble drugs. Accordingly, the reduction of particle size can increase dissolution rate, and hence increase bioavailability. This is seen in a known method such as physical grinding in which nanoparticles are reduced from a big size to a smaller size in a media-milling step. However, a problem posed by this method is that it is very time consuming, and hence, it is an inconvenient method of producing nanoparticles. Another problem with this process is that the nanoparticles tend to agglomerate, leading to the growth of nanoparticles, which may result in instability of the nanoparticles.

Another known method relates to a combination of solid dispersion and spray granulation techniques. More particularly, it relates to a process for the preparation of a particulate material by controlled agglomeration method that enables a controlled growth in particle size. This method is especially suitable for use in the preparation of pharmaceutical compositions containing a therapeutically and/or prophylactically active substance which has a relatively low aqueous solubility and/or which is subjected to chemical decomposition. However, this method is not suitable for drugs which have a high melting-point.

Another known method relates to a process for producing a solid dispersion of an active ingredient which comprises feeding the active ingredient and an excipient to an extruder and forming a uniform extrudate. One disadvantage of this method is that a high temperature of the extruder barrel would be needed when the active ingredient has a high melting point in order to attain adequate dispersion of the active ingredient. This would inevitably lead to higher energy costs.

Further, other disadvantages of using solid dispersion of an active ingredient include the inability to scale-up bench-top formulations to manufacturing-sized batches; difficulty in controlling physicochemical properties of the drug; difficulty in delivering solid dispersion formulations as tablet or capsule dosage forms; the need for special handling and storage conditions of the formed drug due to its inability to withstand high temperatures; and instability of the drug and/or the formulation itself.

Another known method for producing drug nanoparticles involves the use of a supercritical fluid, such as supercritical carbon dioxide, to precipitate out drug nanoparticles dissolved in a solvent. The drug nanoparticles are then encapsulated in a polymer by using a non-aqueous solid-oil-oil-oil solid dispersion technique. However, due to the use of a supercritical fluid, high pressures that are in excess of 10 kPa are generally required in order to preserve the supercritical conditions of the supercritical fluid. As such, this method increases the operation costs required due to the use of specialized equipment needed to handle the supercritical fluids and can result in potential safety issues due to the high pressures involved. This method is also highly inflexible because the type of supercritical fluids that is suitable for use in such process is extremely limited.

Another method involved the use of an emulsion containing one or more compounds to be solidified in its dispersed phase and dosing this emulsion with an antisolvent in order to force the compounds to solidify from the emulsion. A disadvantage of this method is that due to the inherent incompatibility of the materials, substantial amounts of emulsifiers are necessary in order to form a stable emulsion. The size of the droplets is highly dependent on the system so that the particle size of the drug particles formed from this process cannot be accurately and adequately controlled. Further, the use of large amounts of emulsifiers could induce undesirable side-effects and is particularly undesirable in the manufacturing or formulation of active pharmaceutical compounds.

Furthermore, a common disadvantage with most of the above methods is the problem of scaling up production to an industrial scale in the pharmaceutical industry.

Therefore, there is a need to provide a process of making drugs nanoparticles that overcomes, or at least ameliorates, one or more of the problems and disadvantages described above.

There is also a need to provide drug nanoparticles that are suitable for oral administration to a patient diagnosed with a disease that requires the use of poorly-soluble drugs for treatment.

SUMMARY

According to a first aspect, there is provided a process for making particles for delivery of drug nanoparticles, the process comprising the steps of (a) forming a suspension of drug nanoparticles by mixing a precipitant solution with an anti-solvent solution under micro-mixing environment, where the formed nanoparticles have a narrow particle size distribution; (b) providing an excipient to at least one of the precipitant solution, the anti-solvent solution and the suspension of drug nanoparticles, the excipient being selected to maintain the drug nanoparticles in a dispersed state when in liquid form; and (c) drying the suspension of drug nanoparticles containing the excipient therein to remove solvent therefrom, wherein removal of the solvent causes the excipient to solidify and thereby form micro-sized matrix particles, each micro-sized particle being comprised of the drug nanoparticles dispersed in a solid matrix of the excipient.

Advantageously, the disclosed process may be used to form drug nanoparticles of compounds that typically have low solubility in an aqueous medium. The drug nanoparticles may be present as substantially individualized particles in the micro-sized matrix particles such that the drug nanoparticles may not substantially aggregate or clump together. The drug nanoparticles may be present as a nano-dispersion in the micro-sized matrix particle. The drug nanoparticles may be more stable as compared to drug particles that are formed from conventional processes. The stability of the drug may be determined by the lack of, or at least, minimal particle growth upon formation of the nanoparticles.

More advantageously, the disclosed process may aid in increasing the solubility of the poorly-soluble drugs upon ingestion by a patient via oral administration. The disclosed process may aid in substantially reducing the size of the drug particles such that drug particles formed from the disclosed process may be in the nano-sized range. By reducing the particle size of the drug particles, the dissolution rate of the drug particles may be substantially increased such that the bioavailability of the drug particles may be increased upon ingestion of the drug.

The use of excipients in the precipitant solution and/or anti-solvent solution may ensure that the excipients at least partly surround or encapsulate the drug nanoparticles as the nanoparticles are being formed. The use of excipients in a suspension of drug nanoparticles before the drying step may ensure that the drug nanoparticles are dried together with the excipients to form a micro-sized matrix particle. The excipients may be in an admixture with the nanoparticles. The excipients, together with the drug nanoparticles, may form at least one matrix particle. Each matrix particle may at least partly surround each drug nanoparticle, such that a plurality of drug nanoparticles may be nanodispersed within each matrix particle. The excipients that surround the drug nanoparticles may stabilize the nanoparticles by substantially preventing particle growth of the nanoparticles.

The disclosed process may form drug nanoparticles that are of the crystal form. The disclosed process may form drug nanoparticles that are of the amorphous form. The disclosed process may form drug nanoparticles that are of the semi-crystalline form. The disclosed process may be used to form a metastable drug nanoparticle or a mixture of drug nanoparticles with crystalline and amorphous form.

The disclosed process may be capable of scaling up to an industrial scale. The disclosed process may be a continuous or a semi-continuous process.

According to a second aspect, there is provided a continuous process for making particles for delivery of drug nanoparticles, the process comprising the steps of (a) forming a suspension of drug nanoparticles by mixing a precipitant solution with an anti-solvent solution under micro-mixing environment, where said formed nanoparticles have a narrow particle size distribution, and wherein at least one of said precipitant solution and said anti-solvent solution comprises an excipient therein, said excipient being selected to maintain said drug nanoparticles in a dispersed state when in liquid form; and (b) drying said suspension of drug nanoparticles containing said excipient therein to remove solvent therefrom, wherein removal of said solvent causes said excipient to solidify and thereby form micro-sized matrix particles, each micro-sized particle being comprised of said drug nanoparticles dispersed in a solid matrix of said excipient, with the proviso that said process does not comprise an ageing step.

According to a third aspect, there is provided a process for making particles for delivery of drug nanoparticles, the process comprising the steps of (a) forming a suspension of drug nanoparticles by mixing a precipitant solution with an anti-solvent solution under micro-mixing environment, where said formed nanoparticles have a narrow particle size distribution; (b) ageing said formed suspension of drug nanoparticles for a period of time sufficient to alter the polymorphic form of said drug; (c) isolating said drug nanoparticles from said suspension; (d) washing said isolated drug nanoparticles to substantially remove solvent therefrom; (e) adding said washed drug nanoparticles to an aqueous solvent having an excipient therein to thereby form a second suspension of drug nanoparticles, said excipient being selected to maintain said drug nanoparticles in a dispersed state when in liquid form; and (f) drying said suspension of drug nanoparticles containing said excipient therein to remove solvent therefrom, wherein removal of said solvent causes said excipient to solidify and thereby form micro-sized matrix particles, each micro-sized particle being comprised of said drug nanoparticles dispersed in a solid matrix of said excipient.

According to a fourth aspect, there is provided a process for making particles for delivery of drug nanoparticles, the process comprising the steps of (a) forming a suspension of drug nanoparticles by mixing a precipitant solution with an anti-solvent solution under micro-mixing environment, where said formed nanoparticles have a narrow particle size distribution; (b) isolating said drug nanoparticles from said suspension; (c) washing said isolated drug nanoparticles to substantially remove solvent therefrom; (d) adding said washed drug nanoparticles to an aqueous solvent having an excipient therein to thereby form a second suspension of drug nanoparticles, said excipient being selected to maintain said drug nanoparticles in a dispersed state when in liquid form; and (e) drying said suspension of drug nanoparticles containing said excipient therein to remove solvent therefrom, wherein removal of said solvent causes said excipient to solidify and thereby form micro-sized matrix particles, each micro-sized particle being comprised of said drug nanoparticles dispersed in a solid matrix of said excipient.

Definitions

The following words and terms used herein shall have the meaning indicated:

The term "nano-sized" is to be interpreted broadly to, unless specified, relate to an average particle size of less than about 1000 nm, particularly between about 50 nm to about 1000 nm, more particularly less than about 500 nm. The term "nanoparticle" refers to a particle with a particle size in the nano-sized range. The particle size may refer to the diameter of the particles where they are substantially spherical. The particles may be non-spherical and the particle size range may refer to the equivalent diameter of the particles relative to spherical particles or may refer to a dimension (length, breadth, height or thickness) of the non-spherical particle.

The term "micro-sized" is to be interpreted broadly to, unless specified, relate to an average particle size of between about 1 μm to about 1000 μm. The particle size may refer to the diameter of the particles where they are substantially spherical. The particles may be non-spherical and the particle size range may refer to the equivalent diameter of the particles relative to spherical particles or may refer to a dimension (length, breadth, height or thickness) of the non-spherical particle.

The term "precipitant solution" is to be interpreted broadly to refer to any solution which comprises one or more solutes dissolved in a solvent or a mixture of solvents that, when added to an anti-solvent, causes a precipitate to form.

The term "anti-solvent" is to be interpreted broadly to refer to a solvent or a mixture of solvents which, when added in a sufficient quantity to the precipitant solution, cause the solute to precipitate from the precipitant solution without removal or reduction of the solvent medium. The anti-solvent used may be substantially miscible with the solvent of the precipitant solution such that the interaction between the anti-solvent and the solvent allows the solute to precipitate from the precipitant solution. The anti-solvent may comprise salts or compounds that promote precipitation.

The term "narrow particle size distribution" is to be interpreted broadly to refer to a steepness ratio, as measured on a SediGraph, of the precipitate particles being less than about 3. The size distribution of the precipitate particles in a given composition may be represented on a SediGraph which plots cumulative mass percent as a function of particle size, where cumulative mass percent is the percent, by weight, of a distribution having a particle size of less than or equal to a given value and where particle size is the diameter of an equivalent spherical particle. The mean particle size in a distribution is the size in micrometers or nanometers of the precipitate particles at the 50% point on the SediGraph for that distribution. The width of the particle size distribution of a given composition can be characterized using a steepness ratio. As used herein, the "steepness ratio" is defined as the average diameter of the particles in the seventy-fifth mass percentile divided by the average diameter of the particles in the twenty-fifth mass percentile. The "narrow particle size distribution" may also be determined using a Malvern Mastersizer™ 2000 which measures particles having sizes from 0.020 µm to 2000 µm or via dynamic light scattering, which measures particles having sizes of less than about 1 µm. A particle size distribution of $D_{50}$ as used herein is defined as the size at which distribution where 50 volume-% of the particles are smaller than that size given. A particle size distribution of $D_{10}$ as used herein is defined as the distribution where 10 volume-% of the particles are smaller than that size given. A particle size distribution of $D_{90}$ as used herein is defined as the distribution where 90 volume-% of the particles are smaller than that size given. The span value is defined as Span=([particle diameter at 90% cumulative size]-[particle diameter at 10% cumulative size])/[particle diameter at 50% cumulative size]. Therefore, the term "narrow particle size distribution" of the precipitate particles refers to a span value of the precipitate particles as being less than about 3, less than about 1.5 or about 1.

The term "micro-mixing environment" is to be interpreted broadly to refer to an environment wherein molecular mixing occurred in a mixing zone when the fluids are mixed. Ultrafast molecular mixing, which creates molecular diffusion between fluid droplets in a turbulent flow environment, is referred as micro-mixing and the resulting mixture is known as a microfluid. The device which provides for the micro-mixing environment is referred as a molecular mixing unit.

The term "high impingement" is to be interpreted broadly to refer to a condition when an impingement force applied may result in the fluids being mixed in the mixing zone to have a Reynolds number in the range selected from the group consisting of 2000-200000, 5000-150000 and 8000-100000. The high impingement created may enable a high degree of mixing in the mixing zone.

The term "high gravity" is to be interpreted broadly to refer to a condition wherein the acceleration of gravity created by centrifuge force in the mixing zone of a molecular mixing unit may be in the range of about 100 to about 15000 m·s$^{-2}$. The high gravity condition created in the mixing zone may generate the high shear required.

The term "high shear" is to be interpreted broadly to refer to a condition when the shear force applied may result in the fluids being mixed in the mixing zone to have a Reynolds number in the range selected from the group consisting of 2000-200000, 5000-150000 and 8000-100000. The high shear created may enable a high degree of mixing in the mixing zone.

The term "agglomeration" and related term "agglomerated" is to be interpreted broadly to refer to an assemblage of a plurality of nano-sized drug particles—which are either loosely or rigidly joined together.

The terms "ageing" or "aging" are to be interpreted broadly to refer to maintaining a suspension of precipitate particles such as drug nanoparticles under conditions (ie such as temperature, pressure, pH value and agitation rate) for a period of time to allow the drug nanoparticles to form a substantially crystalline structure.

The term "continuous", when referring to a process, is to be interpreted broadly to refer to the sequential movement of the drug particles through the steps of the process. The movement of the drug particles from one step to the next step may be almost uninterrupted such that the particles do not substantially remain at one step for an undesired period of time. The term "continuous" may also indicate that the process may not substantially require the step of ageing the precipitate particles.

The term "semi-continuous", when referring to a process, is to be interpreted broadly to refer to a process that is almost continuous, with periodic interruption of the process as necessary for certain steps to be carried out. When the process is interrupted, the particles may stay at one step for a certain period of time, as desired.

The terms "nanodispersion" or "nanodispersed" are to be interpreted broadly to refer to a mixture of drug nanoparticles and at least one type of excipient, where the drug nanoparticles are present in the mixture as substantially discrete particles with minimal aggregation or agglomeration. However, in embodiments where the drug nanoparticles clump together, the size of the resultant particle is still in the nano-sized range and can be considered as being nanodispersed within the mixture.

The term "excipient" is to be interpreted broadly to refer to any inactive ingredient that is part of a medicament or pharmaceutical composition that is suitable for administration to a mammal. The excipient may form the bulk of a matrix particle in which the formed drug nanoparticles are nanodispersed therein. The excipient may aid in substantially preventing agglomeration of the drug nanoparticles that are nanodispersed in the matrix particle.

The term "surfactant", as used herein, is to be interpreted broadly to relate to any composition that is capable of altering surface tension between a liquid and any precipitated particles suspended in the liquid. Suitable surfactants are taught in *McCutcheon's Emulsifiers & Detergents*, at pages 287-310 of the North American Edition (1994), and in *McCutcheon's Emulsifiers & Detergents*, at pages 257-278 and 280 of the International Edition (1994), both published by MC Publishing Co. (McCutcheon Division) of Glen Rock, N.J.

The term "drug" is to be interpreted broadly to refer to a chemical or biological molecule that is capable of conferring beneficial prophylactic and/or therapeutic effects upon administration to a mammal.

The term "poorly-soluble drug" is to be interpreted broadly to refer to a drug which is insoluble or poorly soluble in an aqueous medium, such as water. The solubility of a poorly-soluble drug is typically less than about 10 mg/ml, or less than about 5 mg/ml, in an aqueous medium at physiological temperature and pH.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Disclosure of Optional Embodiments

Exemplary, non-limiting embodiments of a process for making particles for delivery of drug nanoparticles will now be disclosed.

The process comprises the steps of (a) forming a suspension of drug nanoparticles by mixing a precipitant solution with an anti-solvent solution under micro-mixing environment, where the formed nanoparticles have a narrow particle size distribution; (b) providing an excipient to at least one of the precipitant solution, the anti-solvent solution and the suspension of drug nanoparticles, the excipient being selected to maintain the drug nanoparticles in a dispersed state when in liquid form; and (c) drying the suspension of drug nanoparticles containing the excipient therein to remove solvent therefrom, wherein removal of the solvent causes the excipient to solidify and thereby form micro-sized matrix particles, each micro-sized particle being comprised of the drug nanoparticles dispersed in a solid matrix of the excipient.

The drug may be a poorly-soluble drug. Exemplary types of poorly-soluble drugs include, but are not limited to analgesic and anti-inflammatory drugs; antianginals; anti-arrhythmic drugs; antibacterial and antiprotozoal agents; anti-coagulants; antidepressants; anti-diabetic drugs; anti-epileptic drugs; antifungal agents; antihistamines; anti-hypertensive drugs; anti-muscarinic agents; antineoplastic agents; anti-migraine drugs; anti-parasitic agents; anti-Parkinsonian drugs; antipsychotic, hypnotic and sedating agents; anti-stroke agents; anti-thrombotic agents; antitussives; antivirals; beta-adrenoceptor blocking agents; calcium channel blockers; cardiac inotropic agents; contraceptive agents; corticosteroids; dermatological agents; disinfectants; diuretics; gastro-intestinal agents; general anaesthetics; haemostatics; local anaesthetics; opioid analgesics; parasympathomimetics; peptides; sex hormones; steroids; stimulating agents; vasodilators; N-oxides thereof; pharmaceutically acceptable acid or base addition salts thereof and stereochemically isomeric forms thereof.

Specific examples of the above types of poorly-soluble drugs include, but are not limited to the following:

analgesic and anti-inflammatory drugs such as ibuprofen, indomethacin, ketoprofen, meloxicam, nabumetone, naproxen, piroxicam, and COX-2 inhibitors such as celecoxib and rofecoxib;

antianginals such as glyceryl nitrate, isosorbide dinitrate, molsidomine and verapamil;

anti-arrhythmic drugs such as quinidine and verapamil;

antibacterial and antiprotozoal agents such as ampicillin, azithromycin, benzathine, benzylpenicillin, cefprozil, cefuroxime axetil, cephalexin, chloroquine, ciprofloxacin, clarithromycin, clindamycin, doxyxycline, erythromycin, flucloxacillin, fusidic acid, halofantrine, mefloquine, metronidazole, mupirocine, nalidixic acid, ofloxacin, oxacillin, oxytetracycline, pyrimethamine, tetracycline and streptomycin and sulphamethizole;

anti-coagulants such as warfarin;

antidepressants such as amineptine, amoxapine, butriptyline, clomipramine, desipramine, dothiepin, doxepin, fluoxetine, gepirone, imipramine, mianserin, milnacipran, nortriptyline, paroxetine, selegiline, and sertraline;

anti-diabetic drugs such as glibenclamide and metformin;

anti-epileptic drugs such as carbamazepine, clonazepam, gabapentin, lamotrigine, phenobarbitone, phenyloin, primidone, tiagabine, and valpromide;

antifungal agents such as amorofine, amphotericin, bifonazole, clotrimazole, econazole, fluconazole, griseofulvin, itraconazole, ketoconazole, nystatin, terbinafine, terconazole, tolnaftate and voriconazole;

antihepatotoxic drug such as silybin;

antihistamines such as astemizole, cinnarizine, cyproheptadine, fexofenadine, flunarizine, levocabastine, loratadine, oxatomide, promethazine, and terfenadine;

anti-hypertensive drugs such as enalapril, ketanserin, minoxidil, prazosin, ramipril, reserpine, and telmisartan;

anti-muscarinic agents such as Pirenzepine and Flavoxate;

antineoplastic agents and antimetabolites such as taxanes, such as paclitaxel and docetaxel; tecans such as camptothecin, irinotecan and topotecan; vinca alkaloids such as vinblastine, vincristine and vinorelbine; nucleoside derivatives and folic acid antagonists such as thioguanine, cladribine and methotrexate; alkylating agents such as the nitrogen mustards, e.g. chlorambucil, melphalan, or the nitrosoureas, e.g. carmustine, lomustine, or other alkylating agents, e.g. busulphan, procarbazine; nonsteroidal antiandrogens such as bicalutamide; antibiotics such as daunorubicin, doxorubicin, idarubicin, epirubicin, bleomycin, dactinomycin; HER 2 antibodies such as trastuzumab; podophyllotoxin derivatives such as etoposide and teniposide; farnesyl transferase inhibitors; anthrachinon derivatives such as mitoxantron;

anti-migraine drugs such as dihydroergotamine, ergotamine, and sumatriptan;

anti-parasitic agents such as albendazole;

anti-Parkinsonian drugs such as benzhexyl, levodopa and selegiline;

antipsychotic, hypnotic and sedating agents such as alprazolam, buspirone, chlordiazepoxide, chlorpromazine, clozapine, diazepam, flupenthixol, fluphenazine, flurazepam, 9-hydroxyrisperidone, lorazepam, olanzapine, oxazepam, pimozide, pipamperone, promazine, risperidone, selfotel, seroquel, sertindole, sulpiride, temazepam, thiothixene, triazolam, trifluperidol, and ziprasidone;

anti-stroke agents such as aptiganel, eliprodil lubeluzole, lubeluzole oxide, remacemide and riluzole;

anti-thrombotic agents such as warfarin;

antitussives such as dextromethorphan and laevodropropizine;

antivirals such as abacavir, acyclovir, adefovir, amprenavir, delavirdine, efavirenz, ganciclovir, indinavir, loviride, lopinavir, nevirapine, nelfinavir, ritonavir, saquinavir, and tivirapine;

beta-adrenoceptor blocking agents such as carvedilol, nebivolol and propanolol;

calcium channel blockers such as diltiazem, nicardipine, nifedipine and verapamil;

cardiac inotropic agents such as digitoxin, digoxin and milrinone;

contraceptive agents such as ethinyl estradiol, etynodiol, lynestrenol, mestranol, norethisterone, norgestrel, levonorgestrel and medroxyprogesterone;

corticosteroids such as alklometasone-dipropionate, beclomethasone, betamethasone, betamethasone-17-valerate, betamethasone-dipropionate, chlorchinaldol, cliochinol, clobetasol, clobetasol-17-butyrate, clobetasol-propionate, desonide, desoxymethasone, dexamethasone, diflucortolone, diflurason-diacetate, fluocinoide, fluocinolone acetonide, fluocortolone, flumethasone, flumethasone-pivalte, flupred-nide acetate, fluticason-propionte, hacinonide, halquinol, hydrocortisone, hydrocortisone-17-butyrate, hydrocortisonebuteprate, methylprednisolone, mometasone-furate and triamcinolone acetonide;

dermatological agents such as clioquinol, dithranol, isotretionin, methoxsalen, nitrofurantoin, and tretionin;

disinfectants such as chlorhexidine;

diuretics such as acetazolamide, flunarizine, furosemide, hydrochlorothiazide, isosorbide and minoxidil;

gastro-intestinal agents such as cisapride, diphenoxylate, domperidone, famotidine, lansoprazole, loperamide, metoclopramide, omeprazole, and sulphasalazine;

general anaesthetic such as alfaxalone;

haemostatics such as phytonadione and menadione;

lipid regulating agents such as atorvastatin, fenofibrate, lovastatin, pravastatin, probucol and simvastatin;

local anaesthetics such as benzocaine and lignocaine;

opioid analgesics such as buprenorphine, oxymorphone, and morphine;

parasympathomimetics and anti-dementia drugs such as AIT-082, tacrine, donepezil, rivastigmine, and memantine;

peptides such as growth hormone releasing factors, growth factors (e.g. epidermal growth factor (EGF)), calcitonin, insulin, interferons, IL-2 etc., oxytodin, erythropoietin (EPO), cyclosporine and tacrolimus;

sex hormones such as oestrogens, conjugated oestrogens, ethinyloestradiol, mestranol, oestradiol, oestriol, chlormadinone acetate, cyproterone acetate, desogestrel, dienogest, dydrogesterone, ethynodiol diacetate, gestodene, 3-keto desogestrel, levonorgestrel, lynestrenol, medroxyprogesterone acetate, megestrol, megestrol acetate norethindrone, norethindrone acetate, norethynodrel, norgestimate, norgestrel, norgestrienone, and progesterone;

steroids such as estradiol, progesterone, norethindrone, levonorgestrel, ethynodiol, norgestimate, gestanin, desogestrel, 3-ketone-desogesterel, demegestone, promethoestrol, testosterone, spironolactone and esters thereof;

stimulating agents such as sildenafil, and vardenafil; and vasodilators such as amlodipine, amyl nitrite, diltiazem, dipyridamole, isosorbide dinitrate, lidoflazine, molsidomine, nicardipine, nifedipine, and pentaerythritol tetranitrate.

The above poorly-soluble drugs may be dissolved in a suitable solvent to form the precipitant solution. Exemplary solvents that are suitable for the poorly-solution drug to be dissolved therein can be selected from haloforms, lower ($C_1$ to $C_{10}$) alcohols, organic acids, amides, nitriles, esters, ethers, aldehydes and ketones. It is to be appreciated that the choice of a suitable solvent for the poorly-soluble drug is known in the art without undue experimentation. Further, it is to be appreciated that the solvent may be selected such that it is substantially miscible with the anti-solvent. The choice of solvent used to form the precipitant solution may depend on the type of post-precipitation step required, as will be explained further below.

Exemplary types of haloforms include dichloromethanes and chloroforms. Exemplary types of lower alcohols include methanols, ethanols, isopropanols and isobutanols. Exemplary organic acids include formic acids and acetic acids. Exemplary amides include formamides, dimethylformamides and N,N-dimethylformamides. Exemplary nitriles include aceto-nitriles. Exemplary esters include ethyl acetates. Exemplary ethers include tetrahydrofurans. Exemplary ketones include methyl ethyl ketones and acetones.

The precipitant solution and/or antisolvent solution may comprise at least one excipient. In some embodiments, the excipient may be selected such that it is able to form a matrix particle that surrounds the drug nanoparticles that may be nanodispersed therein.

Types of excipients may include diluents, surfactants, disintegrants, etc.

The excipient may be selected from the group consisting of synthetic polymers, polyacrylamides, polyvinylformamides, modified natural polymers, starch degradation products, natural polymers, cellulose derivatives, natural surfactants, nonionic surfactants, anionic surfactants, cationic surfactants and colloidal clays.

Types of excipients may include, but are not limited to, the following:

synthetic polymers such as polyvinyllactams, polyvinylpyrrolidones (PVP), copolymers of vinyllactams such as N-vinylpyrrolidone, N-vinylpiperidone and N-vinyl-e-caprolactam, copolymers of vinyl acetate and crotonic acid, partially hydrolyzed polyvinyl acetates, polyvinyl alcohols, (meth)acrylic resins. (such as poly(hydroxyalkyl(meth)acrylates), poly(meth)acrylates, acrylate copolymers and copolymers of dimethylaminoethyl acrylates and methacrylic esters), polyalkylene glycols such as polypropylene glycols and polyethylene glycols with molecular weights in the range from about 1000 to about 20000000 Dalton, polyalkylene oxides such as polypropylene oxides and polyethylene oxides, and copolymers of methyl methacrylate and acrylic acid;

modified natural polymers such as modified starches and modified celluloses, such as cellulose esters and cellulose ethers, such as, for example, methylcelluloses, ethylcelluloses, hydroxyalkylcelluloses (such as hydroxypropylcelluloses), hydroxyalkylakylcelluloses (such as hydroxypropylmethylcelluloses or hydroxypropylethylcelluloses), cellulose phthalates, cellulose acetate phthalates and hydroxypropylmethylcellulose phthalates;

starch degradation product such as maltodextrin;

natural polymers such as gelatins, polyhydroxyalkanoates, polyhydroxybutryric acids and polylactic acids, polyamino acids, polyhydroxybutyric acids, polyasparagines, polydioxanes, polypeptides, mannans and galactomannans;

nonpolymeric binders such as polyols, and sugar alcohols such as maltitol, mannitol, sorbitol, cellobitol, lactitol, xylitol, erythritol and isomalt;

natural surfactants such as caseins, gelatins, tragacanths;

nonionic surfactants such as polyoxyethylene fatty alcohol ethers, sorbitan fatty acid esters, polyoxyethylene fatty acid esters, sorbitan esters, glycerol monostearates, cetyl alcohols; cetostearyl alcohols, stearyl alcohols, poloxamers, polaxamines, noncrystalline cellulose and synthetic phospholipids;

anionic surfactants such as potassium laurates, triethanolamine stearates, sodium lauryl sulfates, alkyl polyoxyethylene sulfates, sodium alginate, negatively charged phospholipids (phosphatidyl glycerols, phosphatidyl inosites, phosphatidylserines, phosphatidic acids and their salts), and negatively charged glyceryl esters, sodium carboxymethylcelluloses, and calcium carboxymethylcelluloses;

cationic surfactants such as quaternary ammonium compounds, benzalkonium chlorides, cetyltrimethylammonium bromides, chitosans and lauryldimethylbenzylammonium chlorides; and colloidal clays such as bentonite and veegum.

Exemplary excipients for the anti-solvent/precipitant system may include lactose monohydrates, anhydrous lactose, various starches, various celluloses and cross-linked polyvinylpyrrolidones, microcrystalline celluloses, such as Avicel® PH101 and Avicel® PH102, microcrystalline celluloses, and silicified microcrystalline celluloses (ProSolv SMCC™), inert fillers, such as microcrystalline celluloses, lactose, dibasic calcium phosphates, saccharides, sorbitols, sucrose, glucose and/or mixtures of any of the foregoing.

Exemplary disintegrants may include, but are not limited to, lightly crosslinked polyvinyl pyrrolidones, corn starches, potato starches, maize starches, and modified starches, croscarmellose sodiums, povidones, cross-povidones, sodium starch glycolates, and mixtures thereof.

It is to be appreciated that the above list of exemplary excipients is not exhaustive and it is to be regarded that any pharmaceutical excipients or excipients that are recognized by the United States Food and Drug Administration as "Generally Regarded As Safe" (GRAS) excipients are within the scope of this invention.

The anti-solvent may be at least partially miscible with the solvent used in the precipitant solution. In one embodiment, the anti-solvent is miscible with the solvent used in the precipitant solution. In another embodiment, the anti-solvent is completely miscible with the solvent used in the precipitant solution such that an emulsion is not formed. The anti-solvent may be selected such that the poorly-soluble drug precipitates from the precipitant solution when the precipitant solution and anti-solvent solution are mixed together. The anti-solvent may be an aqueous solvent such as water.

The type of solvent or anti-solvent chosen should be selected such that it does not substantially affect the biological activity, chemical properties or the physical integrity of the drug.

In one embodiment, the solvent or anti-solvent chosen is not a supercritical fluid such as supercritical carbon dioxide.

In another embodiment, the solvent or anti-solvent chosen is not an emulsion whereby two immiscible liquids are present in the emulsion.

The amount of excipient used in the anti-solvent/precipitant system may be dependent on the type of excipient used and/or dependent on the type of drug. The amount of excipient present in the matrix particle may be in the range of about 0.1 wt % to about 90 wt %, about 0.1 wt % to about 10 wt %, about 0.1 wt % to about 20 wt %, about 1 wt % to about 80 wt % or about 10 wt % to about 20 wt % based on the weight of the matrix particle. The amount of drug present in the matrix particle may be about 5 wt % to about 90 wt %, about 10 wt % to about 90 wt %, or about 5 wt % to about 10 wt %, or about 20 wt % to about 60 wt % based on the weight of the matrix particle.

The precipitant solution and anti-solvent solution are mixed to allow the drug to precipitate out from the mixture. The precipitated drug particles may be in the nano-sized range.

The precipitating step may be conducted in a micro-mixing environment. In the micro-mixing environment, a high impingement force or high shear force may be applied to the precipitant solution in the presence of an anti-solvent solution in order to form drug nanoparticles in the mixing zone of a micro-mixing unit.

Advantageously, the high impingement force or high shear force applied in the mixing zone forms the drug nanoparticles having a relatively narrow particle size distribution characterized in that the steepness ratio or span value of the final drug nanoparticles suspended in the mixture is less than about 3, or less than about 2, or less than about 1.9, or less than about 1.8, or less than about 1.7, or less than about 1.6, or less than about 1.5, or less than 1.3. In one embodiment, the span value may be about 1.

The dimension of the drug nanoparticles may be in a range selected from the group consisting of about 50 nm to about 500 nm; about 50 nm to about 100 nm; about 50 nm to about 200 nm; about 50 nm to about 300 nm; about 50 nm to about 400 nm; about 100 nm to about 500 nm; about 200 nm to about 500 nm; about 300 nm to about 500 nm and about 400 nm to about 500 nm. In embodiments where the drug nanoparticle is substantially non-spherical in shape, the above particle size refers to the equivalent diameter of the drug nanoparticle, wherein said equivalent diameter is relative to a completely spherical diameter. In some embodiments, the drug nanoparticles are completely spherical and the equivalent diameter is equal to the actual diameter of the drug nanoparticles.

The drug nanoparticles may be of a shape selected from the group consisting of rod, plate, flake, sphere and needle. The morphology of the drug nanoparticle may alter based on the process conditions. Due to the possibility of tailoring the morphology of the drug nanoparticles, the rate of dissolution or the solubility of the drug nanoparticles in an, oral dosage from can be influenced as the morphology of the drug nanoparticles changes.

In order to meet the requirement of micro-mixing for precipitation in a very short time, the molecular mixing unit may be operated under a turbulent state in order to impart high impingement force or high shear force to the mixing zone and to mechanically mix the precipitant solution and the anti-solvent solution into thin films, threads and very fine droplets rapidly. The thin films, threads and very fine droplets of the precipitant solution and the anti-solvent solution in the molecular mixing unit are quickly mixed by the turbulent fluid flow. In order to promote the mixing of the precipitant solution and the anti-solvent solution rapidly, two factors should be present. The first factor is that the Reynolds number should be high enough so that turbulent mixing is achieved in order to intensify the rate of mixing. As will be explained further below, the Reynolds number can be increased by either introducing an impingement force to the mixing zone or by the high shear present in the mixing zone. The second factor is related to the type of reactor used as the molecular mixing unit. The molecular mixing unit can either be a multiple micro-channels impinging stream mixer (MMISM) or a high gravity controlled precipitation (HGCP) reactor. The detailed description of each reactor will be provided further below.

The Reynolds Number shall be regulated on the basis of the equation of:

$$Re = \frac{d \cdot u \cdot \rho}{\mu}$$

wherein, d is the diameter of the pipe inlet (or distributor in the molecular mixing unit) providing the liquid stream (i.e. precipitant solution or anti-solvent) to the molecular mixing unit, u is the flow speed of the liquid stream, ρ is the density of the liquid stream and μ is the viscosity of the liquid stream.

The relationship of the diameter of the pipe inlet or distributor, the flow speed and flux is shown in the equation of:

$$Q = \frac{\pi \cdot d^2 \cdot u}{4}$$

wherein, Q is the flux of the liquid stream. As can be seen, once the diameter of the pipe inlet or distributor is determined, the flow speed is determined by the flux of the liquid stream. It shall be further noted that a pressure is required to maintain the flux of the ejected flow. Therefore, the related parameters can be concluded as the diameter of pipe, the flux, the pressure and the Reynolds Number.

The process may comprise the step of impinging the mixture of precipitant solution and anti-solvent solution substantially throughout the mixing zone to induce the impingement force. The impingement force may result in the fluids mixed in the mixing zone having a Reynolds number in the range selected from the group consisting of 2000-200000, 5000-150000 and 8000-100000, thereby enabling a high degree of mixing in the mixing zone.

The process may comprise the step of agitating the mixture of precipitant solution and anti-solvent solution substantially throughout the mixing zone to induce the shear force. The shear force may result in the fluids mixed in the mixing zone having a Reynolds number in the range selected from the group consisting of 2000-200000, 5000-150000 and 8000-100000, thereby enabling a high degree of mixing in the mixing zone.

In one embodiment, the mixing zone is located within an enclosed chamber of a molecular mixing unit. The molecular mixing unit may further comprise at least two fluid inlets to introduce fluids such as the precipitant solution and the anti-solvent solution into the enclosed chamber and optionally one outlet to allow suspended drug nanoparticles to be removed from the enclosed chamber.

In one embodiment, the molecular mixing unit may comprise a MMISM within the enclosed chamber. The impinging step to induce the high impingement force during the mixing step may be provided by a MMISM as previously disclosed in the Chinese Patent Application number CN200910131858.0 filed on 9 Apr. 2009 (published as CN 101507908A), the disclosure of which is herein incorporated as reference.

In another embodiment, the molecular mixing unit may comprise an agitator within the enclosed chamber. The agitating step to induce the shear force during the reacting step may be provided by an agitator and shear means as previously disclosed in the International Patent Application number. PCT/SG2007/000333 (published as WO 2008/041951), the disclosure of which is herein incorporated as reference.

The use of a MMISM to impart high impingement force or an agitator to impart high shear force to the mixing fluids in the mixing zone may ensure that the precipitant solution and the anti-solvent fluid may be adequately and homogeneously mixed in a short period of time, such as less than about 1 hour, less than about 1 minute, less than about 10 s, less than about 1 s, or less than about 10 ms, to form an intimate mixture leading to formation of a precipitate of drug nanoparticles.

The operating temperature and pressure of the molecular mixing unit are not particularly limited but in most embodiments, the operating temperature may be in the range of about 0° C. to about 100° C. while the operating pressure may be at atmospheric pressure. In one embodiment, the operating temperature may be in the range of about 20° C. to about 90° C. In another embodiment, the operating temperature may be less than about 40° C. The operating temperature used may be selected based on the boiling point of the solvent used in the precipitant solution, the boiling point of the anti-solvent as well as the stability of the drug or excipient used in the process.

In one embodiment, the agitator in the molecular mixing unit comprises a rotator-stator (or rotor-stator) disposed within an enclosed chamber, the rotator (or rotor) being rotatable about a longitudinal axis and the stator being stationary for imparting a high shear force to the mixture of precipitant solution and anti-solvent solution within the mixing zone.

In one embodiment, the agitator comprises a packed bed disposed within the enclosed chamber, the packed bed being rotatable about a longitudinal axis for imparting a shear force to the mixture of precipitant solution and anti-solvent solution within the mixing zone in use. The packed bed may aid to split the precipitant solution and the anti-solvent solution into thin films, threads and very fine droplets under the high shear environment. The packing may have a surface area in the range of about 100-3000 m$^2$/m$^3$. The packing can be such that it is structured packing or random packing. In one embodiment, the packing is a packing of the wire mesh type packing that can be made from a relatively inert material such as stainless steel, plain metal alloy, titanium metal or plastic.

In one embodiment, the packing is substantially cylindrically-shaped and comprises at least one mesh layer. In one embodiment, the packing is comprised of a plurality of overlapping mesh layers.

Applying a shear force to the mixture of precipitant solution and anti-solvent solution within the mixing zone may be undertaken by a shear means. In one embodiment, the shear means is in the form of a rolling mesh to form a cylindrical shear means, wherein the cylindrical section has sides formed by a plurality of overlapping mesh layers. The mesh may have a mesh size of about 0.05 mm to about 3 mm or about 0.1 mm to about 0.5 mm: The mesh may have mesh porosity of at least 90%, or more than 95%.

In one embodiment, the packed bed is mounted on a shaft in the mixing zone and rotates in the mixing zone. As the packed bed rotates, the packing imparts high shear onto the injected precipitant solution and, anti-solvent solution. In one embodiment, the rotating packed bed is cylindrically shaped and defines a hollow to accommodate the inlets for the precipitant solution and anti-solvent solution.

Advantageously, in order to meet the requirement of micro-mixing of the precipitant solution and anti-solvent solution within a very short period of time, the agitator rotates in the mixing zone at a speed to achieve a high-gravity level $g_r$ (m/s$^2$) sufficient to input high shear to the mixture of precipitant solution and anti-solvent in the mixing zone. The high-gravity level can be regulated based on the equation of:

$$g_r = \left(\frac{2\pi N}{60}\right)^2 \cdot \frac{d_{in} + d_{out}}{2}$$

where N is the rotating speed of the agitator in rpm, $d_{in}$ is the inner diameter and $d_{out}$ is the outer diameter of the agitator.

The high gravity level is selected from the group consisting of about 100 to about 15000 m·s$^{-2}$, about 500 to about 2000 m·s$^{-2}$, about 1000 to about 5000 m·s$^2$, and about 800 to about 5000 m·s$^{-2}$. The use of such a strong high-gravity level of the agitator ensures that the precipitant solution and anti-solvent solution in the mixing zone are subjected to strong shear immediately upon injection into the mixing zone. Therefore, the type of precipitation carried out here may be termed as High Gravity Controlled Precipitation (or HGCP). Accordingly, the molecular mixing unit may be termed as a HGCP reactor.

In one embodiment, the molecular mixing unit comprises an inner distributor and an outer distributor, an inner distributor nozzle and an outer distributor nozzle. The distributors and nozzles can be made from a relatively inert material such as stainless steel, plain metal alloy, titanium metal or plastic. The diameter of eyelet for inner distributor nozzle is selected from the group consisting of about 0.01 to about 5.0 mm, about 0.05 to about 1.0 mm, and about 0.1 to about 2.0 mm. The diameter of eyelet for outer distributor nozzle is selected from the group consisting of about 0.02 to about 5.5 mm, about 0.08 to about 1.5 mm, and about 0.2 to about 3.0 mm. The use of such small diameter of eyelet for distributor nozzles ensures that the precipitation solution and anti-solvent solution in the mixing zone are subjected to strong impingement, collision and mixing immediately upon injection into the mixing zone. Hence, the Reynolds number in the mixing zone is increased due to the high velocity of the precipitant solution and anti-solvent solution through the small diameter of eyelet. Therefore, the molecular mixing unit is known as a Multiple Micro-channels Impinging Stream Mixer (or MMISM).

In one embodiment, the outer distributor surrounds the inner distributor. The outer distributor nozzle surrounds the inner distributor nozzle. In one embodiment, the molecular mixing unit is comprised of a plurality of distributors and distributor nozzles.

In one embodiment, the MMISM comprises a cylindrical collection chamber to collect and further mix the mixture of the precipitation solution and anti-solvent solution.

In one embodiment, the MMISM may comprise an ultrasonic probe located at the bottom of the cylindrical collection chamber to prevent the formed nanoparticles from aggregating.

In one embodiment, the MMISM may comprise a nozzle cleaner to clean the inner distributor nozzle regularly in order to ensure continuous flow in the mixing zone.

The MMISM may be capable of intensifying liquid-liquid micromixing and can be used for continuous production of micro- or nano-particles for inorganic, organic and pharmaceutical compounds.

In one embodiment, the precipitant solution and anti-solvent solution are injected into the mixing zone via a plurality of the inlets extending through a mixing chamber surrounding the mixing zone. The inlets may be arranged in a number of ways depending on the structural design of the mixer. In one embodiment, the inlets are located in a distributor capable of distributing the precipitant solution and anti-solvent solution into the mixing zone. The distributor may comprise a body having a plurality of inlets for each of the precipitant solution and anti-solvent solution.

In one embodiment, the precipitant solution and anti-solvent solution are respectively injected into the mixing zone via separate inlets.

The molecular mixing unit may comprise at least one liquid outlet means for draining the suspension of drug nanoparticles from the mixing zone when the mixing unit is operated in either batch mode or continuous mode.

In one embodiment, the suspension may be drained directly into the inlet of a drying unit. This allows for the possibility of an integrated unit made up of the micro-mixing unit and the drying unit. This may allow for the possibility of scaling up to larger capacities and hence increases the yield of drug nanoparticles obtained.

Due to the direct feeding of the suspension from the molecular mixing unit into the drying unit, a continuous process may be created such that the precipitated drug nanoparticles may not be substantially subjected to an ageing step. Accordingly, the time interval between the formation of the precipitate drug nanoparticles and introduction of the nanoparticles into the drying unit may be in the order of seconds or milliseconds. Due to the lack of, or at least, minimal ageing time of the formed drug nanoparticles, the drug nanoparticles may be prevented from growing in size such that the stability of the drug nanoparticles may be controlled.

In another embodiment, the suspension of drug nanoparticles from the mixing zone may be subjected to an ageing step before the drying step. Due to the use of an ageing step, the resultant process becomes a semi-continuous process.

The ageing step may be carried out at a temperature of about 5° C. to about 85° C.; about 5° C. to about 70° C.; about 5° C. to about 50° C.; about 5° C. to about 30° C.; about 5° C. to about 10° C.; about 10° C. to about 85° C.; about 30° C. to about 85° C.; about 50° C. to about 85° C.; about 70° C. to about 85° C.; or about 50° C. to about 60° C.

The ageing step may be carried out for a period of time selected from the group consisting of about 0.1 hours to about 5 hours; about 0.5 hours to about 5 hours; about 1 hour to about 5 hours; about 3 hours to about 5 hours; about 0.1 hours to about 3 hours; about 0.1 hours to about 1 hours; about 0.1 hours to about 0.5 hours; and about 1 hour to about 2 hours.

The ageing step may be carried out at a selected temperature for a selected period of time at an agitation speed selected from the group consisting of about 0 rpm to about 20,000 rpm; about 0 rpm to about 800 rpm; about 0 rpm to about 400 rpm; about 400 rpm to about 1200 rpm; about 1000 rpm to about 20,000 rpm; and about 8000 rpm to about 1200 rpm.

The ageing step may be carried out in a beaker that is heated at the defined temperature and having a magnetic stirrer therein to provide the agitation. Alternatively, the ageing step may be carried out in a homogenizer or in a rotating packed bed reactor as shown in FIG. 1c.

The ageing step may aid in altering the degree of crystallinity of the drug nanoparticles in the suspension. For example, the suspended drug nanoparticles may be of the amorphous form or semi-crystalline form before the ageing step and the aged drug nanoparticles may at least be in the crystalline form.

It is to be appreciated that the conditions of the ageing step should not result in a significant increase in the particle size of the drug nanoparticles. The conditions in the ageing step may be selected such that the drug nanoparticles are converted from the amorphous form or semi-crystalline form to the crystalline form while keeping the particle size of the drug nanoparticles to be in the nano-sized range.

The ageing step may be followed by an isolating step. In another embodiment, the suspension of drug nanoparticles from the mixing zone may be subjected directly to an isolating step, without passing through an ageing step.

In the isolating step, the drug nanoparticles may be substantially removed or separated from the suspension. The isolating step may be carried out by filtering or centrifuging the suspension in order to obtain the drug nanoparticles. A vacuum filtration or pressure filtration may be used in the filtering step. It is to be appreciated that the time required for the filtering step will vary depending on the capacity of the filtration unit, the amount of slurry to be filtered and the pressure used in the filtration unit. The temperature used in the filtering step is typically room temperature (about 20° C. to about 25° C.).

The obtained drug nanoparticles may be subjected to a washing step to further remove any solvent or anti-solvent that had not been removed during the isolating step. In one embodiment, the anti-solvent may be used as the washing solvent. The washing solvent may aid in substantially removing solvent and/or impurities which may have been generated during the precipitation process. The isolating and washing step may aid in the removal of solvents that are not suitable to be present in a drying unit. For example, certain solvents used in the precipitant solution may have a high boiling point such that their presence in the suspension during the drying step may result in partial or inefficient drying of the suspension because a higher temperature may be required to substantially remove the solvent to obtain dried drug nanoparticles. It is to be appreciated that the washing solvent is chosen such that it does not dissolve the drug and does not affect the morphology of the drug particle.

Accordingly, the choice of solvent used may determine the process route after the mixing step. For example, if a solvent having a low boiling point is used, the mixing step may proceed to the drying step directly or be subjected to an isolation process. In another example, if a solvent having a high boiling point is used, the suspension of drug nanoparticles that is formed from the mixing step may be subjected to an isolating step to substantially remove the solvent.

After the washing step, the drug nanoparticles are collected. The collected drug nanoparticles may be redispersed in a redispersion solvent to form a suspension of drug nanoparticles in the redispersion solvent. Excipients may be added to the redispersion solvent such that the excipients are in admixture with the drug nanoparticles. The suspension comprising drug nanoparticles in admixture with the excipients may be fed to a drying unit. An exemplary redispersion solvent may be water or may be an organic solvent such as an alcohol (for example, ethanol or methanol). It is to be appreciated that any solvent that is capable of solubilizing an excipient but does not dissolve the drug nanoparticles can be used as the redispersion solvent.

In one embodiment, the drying unit may be a spray dryer. Suitable spray-drying techniques are described, for example, by K. Masters in "Spray Drying Handbook", John Wiley & Sons, New York, 1984. Generally, during spray-drying, heat from a hot gas such as heated air or nitrogen is used to evaporate the solution in which the drug nanoparticles are suspended in. Typically the nano-particles, while suspended in the mixture, are atomized by an atomizer to form an atomized droplet wherein the liquid of the atomized droplet is rapidly evaporated by application of heat. Due to the small nature of the atomized droplet, and the application of heat, the liquid medium is rapidly evaporated.

The inventors have surprisingly discovered that by rapidly spray drying the suspension, the excipients substantially surround or encapsulate the drug nanoparticles such that the drug nanoparticles are substantially individualized particles. Further, depending on the nature and type of excipients used, the excipients may form a solid or semi-solid matrix particle around the nanoparticles such that the nanoparticles are individual particles within the matrix particle. Accordingly, the nanoparticles may be nanodispersed within the matrix particle.

The matrix particle may be in the micro-sized range. The dimension of the matrix particles may be in a range selected from the group consisting of about 1 µm to about 1000 µm; about 1 µm to about 100 µm; about 1 µm to about 50 µm; about 1 µm to about 10 µm; about 1 µm to about 5 µm; about 1 µm to about 2 µm; about 5 µm to about 1000 µm; about 10 µm to about 1000 µm; about 100 µm to about 1000 µm; and about 500 µm to about 1000 µm. In embodiments where the matrix particle is substantially non-spherical in shape, the above particle size refers to the equivalent diameter of the matrix particle, wherein said equivalent diameter is relative to a completely spherical diameter. In some embodiments, the matrix particles are completely spherical and the equivalent diameter is equal to the actual diameter of the drug nanoparticles.

In one embodiment, a spray dryer using rotary atomization such as the Mobile Minor™ spray drier by Niro A/S of Søborg, Denmark is used. In another embodiment, a spray dryer using nozzle atomizers such as the Büchi™ 290 laboratory scale spray dryer from BÜCHI Labortechnik AG of Switzerland is used.

The physical properties of the spray-dried drug nanoparticles depend on a number of parameters such as direction of flow of the drying gas in the drying chamber; the degree and uniformity of atomization due to the type of atomizer used; the amount of nano-sized drug particles in the liquid medium in % solids concentration; the temperature of the liquid medium; efficiency of the collection mechanism and choice of anti-solvent used.

The flow of the drying gas in the drying chamber may be substantially opposite to the flow of the atomized solution (that is, countercurrent flow) or the flow of the drying gas in the drying chamber may be in the same direction as the flow of the atomized solution (that is, cocurrent flow). Some spray dryers may combine both countercurrent and cocurrent flow in the drying chamber. The type of flow pattern in the drying chamber may aid in the generation of turbulence in the drying chamber and hence, may lead to an increased rate of interaction between the drying gas and the atomized droplets in order to increase the rate of heat transfer from the drying gas to the atomized droplets.

Atomization of the suspension into droplets may be effected through atomizing devices such as rotary atomizers and nozzle atomizers. Exemplary nozzle atomizers include pressure nozzles and two-fluid nozzles. The types of atomizers used may determine the size of the atomized droplets, the degree of atomization as well as the spray characteristics such as spray angle or spray direction of the droplets sprayed from the atomizers into the drying chamber.

The inlet temperature of the drying gas into the spray dryer may be in a range selected from the group consisting of about 50° C. to about 220° C.; about 50° C. to about 70° C.; about 50° C. to about 90° C.; about 50° C. to about 110° C.; about 50° C. to about 130° C.; about 70° C. to about 150° C.; about 90° C. to about 150° C.; about 110° C. to about 150° C.; about 150° C. to about 180° C. and about 180° C. to about 220° C. The outlet temperature may be dependent on the inlet temperature selected and is typically in the range of about 20° C.

to about 120° C. In one embodiment, the outlet temperature may be kept below 80° C. in order to ensure that the activity of the drug is retained.

The drying time to convert a droplet to dry powder may be less than about 10 seconds, particularly less than about 5 seconds and more particularly about 1 second.

In another embodiment, the suspension may be dried using freeze-drying. During this process, the suspension is aliquoted out into partially-stoppered glass vials. The vials are then placed in a freeze dryer. To start the freezing process, the temperature of the freeze dryer is reduced until the sample is frozen to a uniform, defined temperature. The cooling temperature may be selected according to the ability of the freeze dryer, but this is not particularly limited. The cooling temperature may be set to below −40° C.

The drying of the liquid medium from the suspension takes place in two stages, termed as primary drying and secondary drying. Primary drying may be initiated by lowering the pressure to form a partial vacuum and slightly increasing the temperature in the freeze dryer such that water present in the frozen sample as ice sublimates to form water vapour that escapes from the frozen sample. The pressure can be lowered by the use of a vacuum pump.

Secondary drying involves further reduction in pressure and further increase in temperature such that any water that is absorbed to the semi-dried mass may be removed until the remaining water content reduces to a desired level.

After the freeze-drying process is completed, an inert gas such as nitrogen may be introduced into the freeze-dryer to break the partial vacuum. The vials may be fully stoppered and stored or the contents may be removed.

In yet another embodiment, the drying unit may be a spray granulator. Suitable spray-granulation techniques are described, for example, in the document titled "Innovative Technologies for Granules and Pellets" available on the website of the company, Glatt GmbH of Germany. Generally, spray-granulation refers to the drying of liquid medium from a suspension while simultaneously building particle size of the particles suspended therein.

During the process, the precipitated drug nanoparticles may act as seeds for the granulation process and can be introduced into the granulation chamber from the outlet of the molecular mixing unit. The seeds may be exposed to sprayed droplets which substantially spread across and cover the entire seed. The sprayed droplets may be made up of a typical formulation that includes a lipid such as partially hydrogenated cottonseed oil, an emulsifying agent such as polysorbate and/or a wax such as castor wax. The sprayed droplets then solidify to form a solidified shell around the seed. The final product is called, a granule, which may have an "onion-like" structure, in that it may have a few layers forming the external shell of the seed. The granule displays properties such as excellent dosing properties, a compact structure and good solubility in an aqueous medium.

The spray-granulation process can be carried out in a number of processing units such as Glatt GFG fluid bed granulator, Glatt AGT continuous fluid bed granulator, and Procell spouted bed granulator, all available from Glatt GmbH of Germany. The difference between the Glatt GFG fluid bed granulator and Glatt AGT continuous fluid bed granulator is that the entire fluid bed is mixed and the product is discharged through a central discharge pipe for the Glatt AGT continuous fluid bed granulator process, while a plug flow is created in the Glatt GFG fluid bed granulator process. As for the Procell spouted bed granulator, air is used during the process to prevent lumping of sticky material. This allows for very small particles to be generated from the granulation process. When compared to the fluid bed processes, the Procell spouted bed granulator allows for the residence time in the granulator chamber to be decreased, resulting in a very gentle process for temperature sensitive materials. The Procell spouted bed granulator requires short processing times but operates at high spray rates. The inlet air temperature for the Glatt GFG fluid bed granulator is about 90° C. while the Procell spouted bed granulator and Glatt AGT continuous fluid bed granulator work at 175° C. and 250° C. respectively.

The resultant granules formed from the spray-granulation process may be used as oral dosage forms for oral administration.

In a further embodiment, the drying unit may be a spray coater. More particularly, this process is referred to as the coating and encapsulation of drug nanoparticles. The drug nanoparticles may be coated in this process such that their surface properties may be altered, leading to a change in the properties of the resultant product, such as stability in storage, good solubility and masking of taste and odor.

The coating liquid can be a solution, suspension or melt. The coating liquid used here may be similar to that used as the formulation to produce sprayed droplets in spray-granulation. Accordingly, the coating liquid may be made up of a typical formulation such as a lipid, an emulsifying agent and/or a wax. Generally, the coating liquid may be sprayed onto the drug nanoparticles and spread over the drug nanoparticles. Low viscosity and small droplets are needed to provide even spreading of the coating liquid on the surface of the drug nanoparticles.

Similar to spray-granulation, the coating process can be carried out using a Glatt AGT continuous fluid bed granulator, a Glatt GFG fluid bed granulator or a Procell spouted bed granulator. For Glatt AGT continuous fluid bed granulator and Glatt GFG fluid bed granulator, when coating in the fluid bed, the drug nanoparticles are fluidized and the coating liquid is sprayed into the bed while the drug nanoparticles are being dried. Over-wetting is prevented so as to substantially curb agglomeration of the drug nanoparticles. As for the Procell spouted bed granulator, when compared to the fluid bed granulators, the residence time in the Procell spouted bed granulator is shorter, allowing for a more even coating in the continuous process.

The spray coating process may lead to the formation of coated drug nanoparticles.

In another embodiment, the coating liquid may be a suspension of the drug nanoparticles to coat an inert core of excipients.

The drug nanoparticles may be in a crystal form, may be in a semi-crystalline form, or may be in an amorphous form. The polymorphic form of the drug may be dependent on the process conditions and the nature of the drug. The drug nanoparticles may be formulated for oral administration in solid, liquid or aerosol form. Types of oral dosage forms that are suitable for administration include tablets, capsules, sachets, lozenges, powders, pills or granules. The dosage form may be releasable at different rates to the body. It is to be appreciated that the type of process used to form the tablets is known to a person skilled in the art and may include wet-granulation process or powder direct compression process.

In the formulation of oral dosage forms, excipients may be added to the formulation. Such excipients may include those that have been described above. The excipients to be added to the formulation may include filling agents, binding agents, lubricants, sweeteners, flavoring agents, preservatives, diluents, disintegrants and effervescent agents.

Exemplary filling agents may include, but are not limited to, lactose monohydrates, anhydrous lactose, and various starches.

Exemplary binding agents may include, but are not limited to, various celluloses and cross-linked polyvinylpyrrolidones, microcrystalline celluloses, such as Avicel® PH101 and Avicel® PH102, microcrystalline celluloses, and silicified microcrystalline celluloses (ProSolv SMCC™).

Exemplary lubricants may include, but are not limited to, colloidal silicon dioxides, such as Aerosil® 200, talc, stearic acids, magnesium stearates, calcium stearates, polyethylene glycols, sodium stearyl fumarates and silica gels.

Exemplary sweeteners may include, but are not limited to, sucrose, xylitol, sodium saccharins, cyclamate, aspartame, and acsulfame.

Exemplary flavoring agents may include, but are not limited to, Magnasweet®, bubble gum flavor, and fruit flavors, and the like.

Exemplary preservatives may include, but are not limited to, potassium sorbates, methylparabens, propylparabens, benzoic acids and its salts, other esters of parahydroxybenzoic acid such as butylparabens, alcohols such as ethanols or benzyl alcohols, phenolic compounds such as phenols, or quarternary compounds such as benzalkonium chlorides.

Exemplary diluents may include, but are not limited to, pharmaceutically acceptable inert fillers, such as microcrystalline celluloses, lactose, mannitol, dibasic calcium phosphates, saccharides, sorbitols, sucrose, glucose and/or mixtures of any of the foregoing.

Exemplary disintegrants may include, but are not limited to, lightly crosslinked polyvinyl pyrrolidones, corn starches, potato starches, maize starches, and modified starches, croscarmellose sodiums, cross-povidones, sodium starch glycolates, and mixtures thereof.

Exemplary effervescent agents may include, but are not limited to, effervescent couples such as an organic acid and a carbonate or bicarbonate. Suitable organic acids include, for example, citric acids, tartaric acids, malic acids, fumaric acids, adipic acids, succinic acids, and alginic acids and anhydrides and acid salts. Suitable carbonates and bicarbonates include, for example, sodium carbonates, sodium-bicarbonates, potassium carbonates, potassium bicarbonates, magnesium carbonates, sodium glycine carbonates, L-lysine carbonates, and arginine carbonates.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 8a was obtained from micron-sized fenofibrate that was not made according to a disclosed embodiment. FIG. 8b was obtained from spray-dried fenofibrate nanoparticles made in accordance with a disclosed embodiment. FIG. 8c was obtained from spray dried micron-sized fenofibrate particles that were physically mixed with excipients in water.

FIG. 15a (API) was obtained from micron sized crystal Lopinavir that was not made according to a disclosed embodiment. FIG. 15b was obtained from micron sized amorphous Lopinavir that was not made according to a disclosed embodiment. FIG. 15c was obtained from spray-dried powder of Lopinavir nanoparticles made in accordance with a disclosed embodiment.

FIGS. 23a and 23b are FESEM images obtained at 20,000× and 40,000× magnification, respectively, of spray-dried cyclosporine nanoparticles that are redispersed in water.

FIG. 24 is a graph of the particle size distribution of precipitated cyclosporine nanoparticles (A) and of spray-dried cyclosporine nanoparticles that were redispersed in water (B).

In FIG. 30b, the levodopa nanoparticles are further provided in povidone matrix.

FIG. 31a and FIG. 31b are FESEM images at 20,000× and 30,000× magnification, respectively, of the powder levodopa nanoparticles of FIG. 30a and FIG. 30b, respectively, that are re-dispersed in methanol.

FIG. 32a is a graph of the particle size distribution of a suspension of precipitated levodopa nanoparticles (A) and of spray-dried powder levodopa nanoparticles and povidone matrix particles that were redispersed in methanol (B).

FIG. 32b is a graph of the particle size distribution of the samples (A) and (B) of FIG. 32a with spray-dried powder of pure levodopa nanoparticles that were redispersed in methanol (C).

FIG. 33a is a FESEM image obtained at 500× magnification of micro-sized silybin particles that were not obtained according to a disclosed embodiment.

FIG. 33b is FESEM image obtained at 5,000× magnification of processed spray-dried powder silybin nanoparticles.

DETAILED DESCRIPTION OF DRAWINGS

Figure 1A:
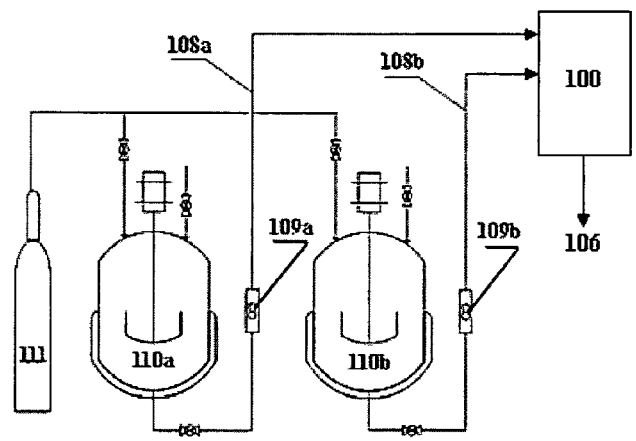
FIG. 1a shows a schematic drawing of a molecular mixing unit for making the nano-sized drug particles according to one disclosed embodiment.
Figure 1B:
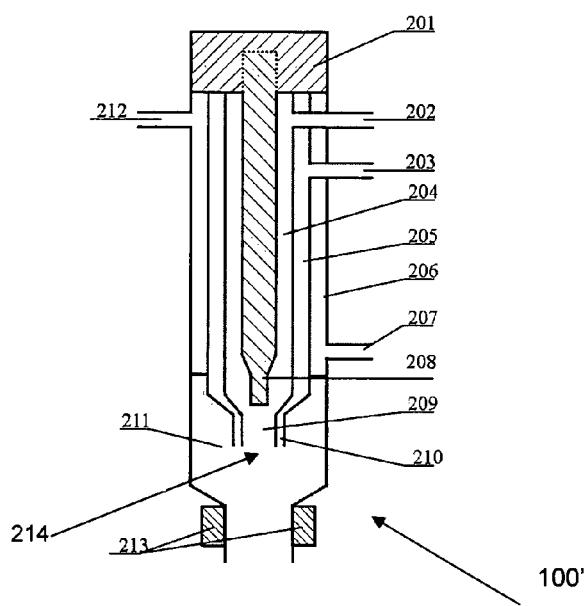
FIG. 1b shows a schematic drawing of a MMISM reactor according to one disclosed embodiment.
Figure 1C:
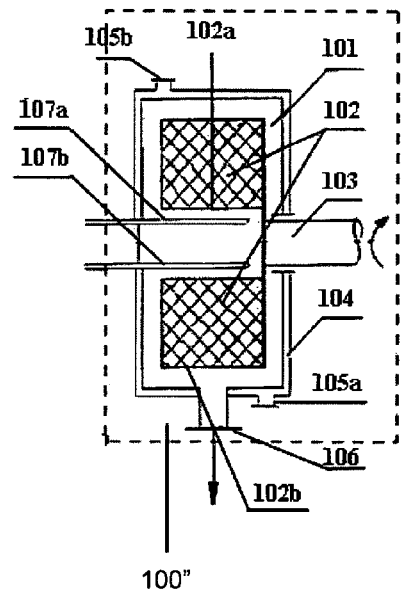
FIG. 1c shows a schematic drawing of a HGCP reactor according to one disclosed embodiment.

Referring to FIG. 1a, there is shown a molecular mixing unit 100 which can be of two types, one of which is shown in FIG. 1b as a multiple micro-channels impinging stream mixer 100' and the other of which is shown in FIG. 1c as a high gravity controlled precipitation reactor 100".

Referring to FIG. 1b, there is shown a molecular mixing unit 100' in the form of a multiple micro-channels impinging stream mixer (MMISM).

The MMISM reactor is also named as multiple channels micro-reactor (MCMR). The MMISM reactor 100' is suitable for carrying out the process for forming drug nanoparticles. The reactor 100' comprises two solution inlet (solution inlet 1202 and solution inlet II 203), an inner distributor 204, an outer distributor 205, an inner distributor nozzle 209, and an outer distributor nozzle 210. The outer distributor 205 surrounds the inner distributor 204. The outer distributor nozzle 210 surrounds the inner distributor nozzle 209 to form the multiple micro-channels structure.

A temperature jacket 206 surrounds the outer distributor 205 to regulate the temperature within the outer distributor 205 and inner distributor 204. The temperature jacket 206 comprises a jacket inlet 207 for allowing heated or cooled medium to enter, and a jacket outlet 212 for allowing the fluid to exit from the jacket.

The solution inlet 1202 is linked by pipe 108a of FIG. 1a to a precipitant-solution feed tank 110a where the precipitant solution containing the drug compound is stored under pressure provided by a nitrogen gas cylinder 111. The precipitant solution may contain a surfactant. The pressure pushes the precipitant solution from the storage tank 110a to the solution inlet 1202. The solution inlet II 203 is also linked by pipe 108b of FIG. 1a to an anti-solvent solution feed tank 110b where the anti-solvent solution, in which the drug compound is insoluble, is stored under pressure provided by the nitrogen gas cylinder 111. The anti-solvent solution may contain at least one excipient. The pressure pushes the anti-solvent solution from the storage tank 110b to the solution inlet II 203.

As shown in FIG. 1a, a pair of flow meters 109a, 109b is positioned along the pipes 108a, 108b respectively to regulate the flow of the precipitant solution and the anti-solvent solution to the inner distributor 204, and the outer distributor 205 of FIG. 1b.

As the inner distributor nozzle 209 and outer distributor nozzle 210 serve to narrow the cross-sectional flow area of the distributors and due to the fast flow rates of precipitant and anti-solvent solutions when passing through the distributor nozzles, both solutions are subjected to strong impingement, collision and mixing immediately upon injection into the mixing zone 214. Accordingly, this results in an intense micro-mixing and high mass transfer rate between the two solutions to form a uniformly-supersaturated solution in which precipitates of nano-sized drug compounds are formed.

A nitrogen driven probe 208 is provided in the MMISM to clear the particles on the core of the internal distributor nozzle 209 by periodically purging the internal distributor nozzle 209 with nitrogen driven probe 208 to prevent blockage of the core. The nitrogen driven probe 208 can either be a hollow structure or a solid structure and can be used to clear the core about 1 to 200 times/minute, depending on the requirement.

The nitrogen driven probe 208 is controlled by a probe controller 201 which comprises a spring and a valve. The spring is installed on top of the nitrogen driven probe 208 and connected to the valve. The other end of the valve is connected to the nitrogen source which is stored under high pressure. The valve is controlled by a computer program and can be opened or closed at predefined time intervals. When the valve is closed, the pressure drops to atmospheric pressure so that the spring reverts to its original position. The nitrogen driven probe 208 can then ensure the continuous operation of the MMISM by periodically clearing the core of the inner distributor nozzle 209. If the nitrogen driven probe 208 has a hollow structure, the nitrogen driven probe 208 is connected to the valve directly without the need for a spring. The surfactant imparts surface charge to the particles of drug compounds, which results in electrostatic, steric or electrosteric repulsion between the drug particles.

The electrostatic, steric or electrosteric repulsion between the drug particles aids in substantially reducing or eliminating the aggregation of the drug particles during and after the precipitation process. As the drug particles formed during precipitation do not substantially grow and aggregate, nano-sized drug particles can be formed in the resultant precipitate. Furthermore, because the drug particles do not substantially aggregate even after the precipitation process, they have a narrow particle size distribution which remains substantially constant with time.

The nano-sized particles of drug compounds suspended in the mixture of solvent and anti-solvent are removed from the cylindrical collection chamber 211 via product outlet 106 of FIG. 1a. An ultrasonic probe 213 is installed at the bottom of the collection chamber 211 to disperse the agglomerated particles and hence prevent the formed nanoparticles from aggregating. Thereafter, the suspension may be treated by three different post-precipitation processes.

Referring to FIG. 1c, there is shown a molecular mixing unit 100 in the form of a high gravity controlled precipitation (HGCP) reactor 100".

The HGCP reactor is also named as a rotating packed bed (RPB) reactor. HGCP reactor 100" is suitable for carrying out the process for forming drug nanoparticles. The reactor 100" comprises a chamber 101 having a shaft 103 extending horizontally into the chamber 101. The shaft 103 is driven by a motor (not shown), which rotates the shaft 103. The reactor 100" also comprises an outlet 106 for allowing nano-sized particles of drug compounds to be removed from the chamber 101.

A packed bed 102 is mounted onto the shaft 103 in the chamber 102.

The packed bed 101 is substantially cylindrical in shape and comprises a structured arrangement of a plurality of layers of wire mesh having a mesh size of 5 mm. The wire mesh is made from stainless steel.

A temperature jacket 104 surrounds the chamber 101 to regulate the temperature within the chamber 101. The temperature jacket 104 comprises a jacket inlet 105a for allowing heated fluid to enter, and a jacket outlet 105b for allowing the fluid to exit from the jacket.

A precipitant solution feed distributor 107a and an anti-solvent solution feed distributor 107b are mounted into chamber 102 to enable introduction of the precipitant solution and the anti-solvent solution, respectively, at an inner surface 102a of the packed bed 102.

The precipitant solution feed distributor 107a is linked by pipe 108a of FIG. 1a to a precipitant-solution feed tank 110a where the precipitant solution containing the drug compound is stored under pressure provided by a nitrogen gas cylinder 111. The precipitant solution may contain a surfactant. The pressure pushes the precipitant solution from the storage tank 110a to the precipitant solution feed distributor 107a. The anti-solvent solution feed distributor 107b is also linked by pipe 108b of FIG. 1a to an anti-solvent solution feed tank 110b where the anti-solvent solution, in which the drug compound is insoluble, is stored under pressure provided by the nitrogen gas cylinder 111. The anti-solvent solution may contain an excipient. The pressure pushes the anti-solvent solution from the storage tank 110b to the anti-solvent solution feed distributor 107b.

As shown in FIG. 1a, a pair of flow meters 109a, 109b is positioned along the pipes 108a, 108b respectively to regulate the flow of the precipitant solution and the anti-solvent solution to the feed distributors 107a, 107b of FIG. 1c. The feed distributors 107a, 107b ejects the precipitant solution and the anti-solvent solution into the chamber 101 at the inner surface 102a of the packed bed 102. As the shaft 103 rotates, the packed bed 120 rotates to thereby cause the precipitant solution and the anti-solvent solution to pass through the packed bed 102 in a radial direction from the inner surface 102a toward the outer surface 102b of the packed bed. When passing through the packed bed 102, both solutions are mixed and precipitates of the drug compound of the nano-sized range are formed in a suspension.

In the packed bed 102, the precipitant solution and the anti-solvent solution are subjected to high shear forces in the form of centrifugal forces or gravity field created by the rotational motion of the shaft 103 and the packed bed 102. Accordingly, the precipitant solution and the anti-solvent solution are separated into very fine droplets, threads or thin films under the high gravity field to thereby result in a high mass transfer rate between the two solutions. This results in an intense micro-mixing between the precipitant solution and the anti-solvent solution to form a uniformly-supersaturated solution in which precipitates of nano-sized drug compounds are formed.

The magnitude of the centrifugal force exerted on the mixture within the packed bed 102 is dependent on the speed of rotation of the shaft 103. The higher the speed of rotation of the shaft 103, the larger the magnitude of the centrifugal force acting on the solutions.

The nano-sized particles of drug compounds suspended in the mixture of solvent and anti-solvent are removed from the chamber 101 via product outlet 106. Thereafter, the suspension may be treated by three different post-precipitation processes.

Figure 2:
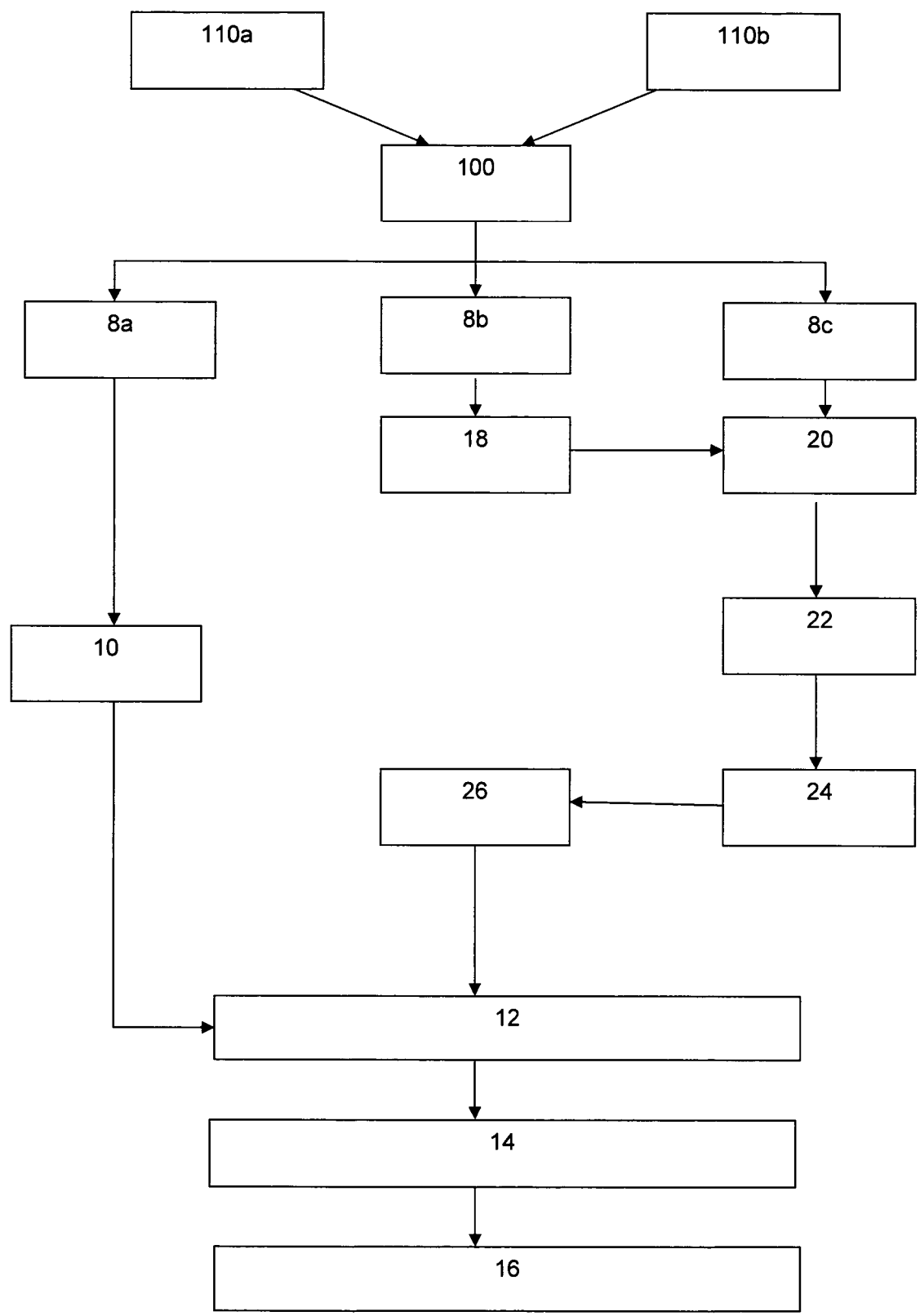
FIG. 2 is a flow chart of the process as disclosed herein.

Referring to FIG. 2, there is provided a process flow diagram showing the different post-precipitation routes that can be taken after the suspension of drug nanoparticles are formed from the rotating packed bed reactor 100 of FIG. 1.

In FIG. 2, the precipitant solution from the precipitant solution storage tank 110a and the anti-solvent solution from the anti-solvent solution storage tank 110b are fed into the rotating packed bed reactor 100 of FIG. 1. The suspension of drug nanoparticles that is obtained from the molecular mixing unit 100 can be processed via one of three post-precipitation routes (8a, 8b, 8c).

Figure 3:
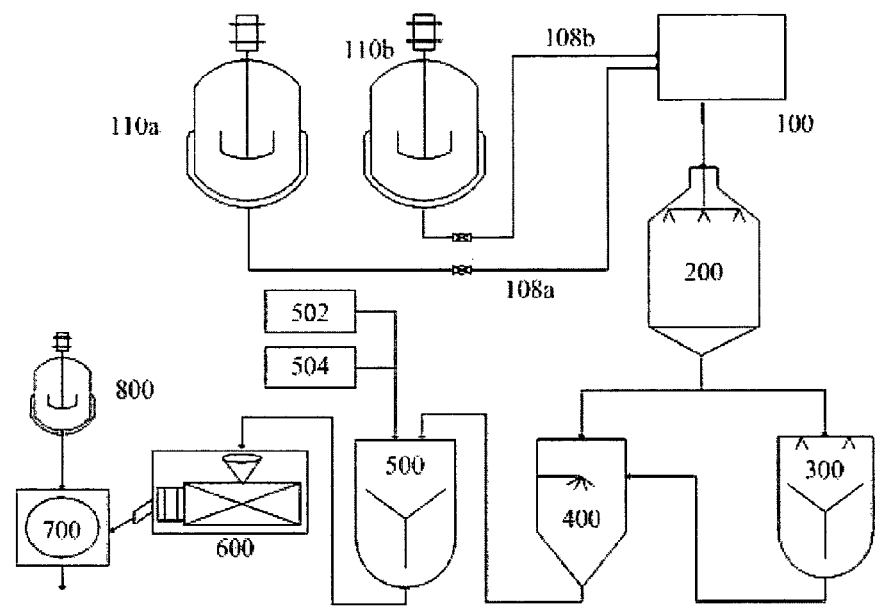
FIG. 3 is a schematic drawing of the process units used in the disclosed continuous process from the precipitating step until the formation of oral dosage forms.

In post-precipitation route 8a, the suspension of drug nanoparticles from the rotating packed bed reactor 100 is almost immediately spray-dried in a continuous process. An inlet of a spray dryer 200 is connected to the outlet of the molecular mixing unit 100 as shown in FIG. 3. In this post-precipitation route 8a, the residence time of the suspension of drug nanoparticles in the molecular mixing unit 100 is minimized to substantially reduce or prevent the growth of particle size and the agglomeration of the drug nanoparticles. Accordingly, an ageing step is not required in this post-precipitation route 8a.

The suspended drug nanoparticles in admixture with the excipients that are present in either or both of the precipitant solution and anti-solvent solution are homogeneously mixed or inter mixed together when dried in the spray dryer 200 to form a powder of nanodispersed drug particles 12. The powder nanodispersed drug particles 12 may comprise a matrix particle comprising nano-sized drug particles and excipients. The matrix particle may be of the micro-sized range. The drug particles may form a nanodispersion within the matrix particle. The powder nanodispersed drug particle may be formulated in a formulation step 14 to form oral dosage forms 16 such as tablets, capsules, pellets, powders, etc. Additional excipients like lubricants or bulking agents can be used in the formulation step 14 to form the oral dosage form 16.

Post-precipitation route 8a can be used to form drug particles with amorphous, semi-crystalline or crystalline forms.

In post-precipitation route 8b, an ageing step 18 is undertaken to obtain the crystalline form of an amorphous or semi-crystalline drug after precipitation in the molecular mixing unit 100. The particle size of the aged drug particle may be of the nano-sized range, indicating that the ageing step did not dramatically increase the particle size of the precipitated drug particles.

After the ageing step 18, an isolating step 20 is undertaken to separate the drug nanoparticles from the suspension. The isolating step 20 may comprise a centrifuge or filtering step. After the drug nanoparticles are isolated, the drug nanoparticles are washed in washing step 22 to obtain drug nanoparticles that are substantially free of the solvent used in the precipitant solution and the impurities which may exist in solvent/anti-solvent system after precipitation.

The obtained drug nanoparticles are then redispersed in a redispersion solvent in a redispersion step 24. In the redispersion step 24, an excipient may be added to the redispersion solvent. A stirrer or an ultrasonicator may be used in the redispersion step 24 to ensure that the drug nanoparticles are adequately mixed with the excipients that are essentially soluble in the redispersion solvent. A resultant suspension of drug nanoparticles in the redispersion solvent is formed after this redispersion step 24.

The suspension of drug nanoparticles with excipients after the redispersion step 24 is then dried in a drying step 26. The type of dryer used in the drying step 26 may be a spray dryer, a spray granulator, a spray coater or a freeze dryer. In this step, the liquid medium is removed from the suspension to form powder nanodispersed drug particles 12. The powder nanodispersed drug particles 12 may comprise a matrix particle with the drug nanoparticles being nanodispered therein. The excipients may form the bulk of the matrix particle and may surround the nanodispersed drug particles therein. The powder nanodispersed drug particles 12 are then formulated in a formulation step 14 to form oral dosage forms 16.

Post-precipitation step 8b can be used to alter the polymorphic form of drug nanoparticles from the amorphous form or semi-crystalline form to crystalline form.

Post-precipitation route 8c is similar to post-precipitation route 8b, except that no ageing step is used in post-precipitation route 8c.

FIG. 3 is a schematic diagram of the process units used in the post-precipitation route 8a of FIG. 2. In FIG. 3, the precipitant solution from precipitant solution storage tank 110a is fed via pipe 108a to the molecular mixing unit 100. The anti-solvent solution from anti-solvent solution storage tank 110b is fed via pipe 108b to the molecular mixing unit 100. After the suspension of drug nanoparticles is obtained from the molecular mixing unit 100, the suspension is almost immediately fed to a spray dryer 200.

The dried powder nanodispersed drug particles are fed to either a high-shear granulator 300 or fluid bed processor 400 to form granules of the powder drug particles.

After the granules are formed, they are blended in a blender 500 with additional tableting excipients 502 and/or lubricants 504 before entering into the tableting machine 600. After the tablets are formed, they are coated in a film coating pan 700 using coating solution from a coating suspension vessel 800. The resultant coated tablets can be suitable for oral administration.

EXAMPLES

Non-limiting examples of the invention will be further described in greater detail by reference to specific Examples, which should not be construed as in any way limiting the scope of the invention.

List of Chemicals

Fenofibrate was obtained from Zhejiang Hisoar Pharmaceutical Co Ltd of China. Lopinavir was obtained from Xiamen Mchem Laboratories of China. Cefuroxime axetil (crystalline) was obtained from North China Pharmaceutical Group Corporation of China. Cyclosporine A was obtained from Fujian Kerui Pharmaceutical Co., Ltd. Bicalutamide was obtained from AstraZeneca Pharmaceuticals of Wilmington of Delaware of the United States of America. Levodopa was obtained from Impax Laboratories, Inc of Hayward of California of the United States of America. Silybin was obtained from Panjin Green Biological Development Co., Ltd. of Liaoning of China. Hypromellose was obtained from Shin-Etsu Chemical of Tokyo, Japan. Sodium lauryl Sulphate was obtained from Sigma Aldrich of St. Louis of Missouri of the United States of America. Lactose was obtained from Friesland Foods Domo of the Netherlands. Ethanol was obtained from Merck & Co, Inc. of Whitehouse Station of New Jersey of the United States of America. Methanol and isopropanol were obtained from Tedia Company Inc. of Fairfield of Ohio of the United States of America. Dimethyl sulphoxide (DMSO) was obtained from Fisher Scientific of Pittsburgh of Pennsylvania of the United States of America. Ammonia solution (25%) and hydrochloric acid (37%) were obtained from Lactose monohydrate was obtained from DMV International in the Netherlands. Microcrystalline cellulose was obtained from JRS Pharma of Patterson of New York of the United States of America. Sodium stearyl fumarate was obtained from Kemimac (S) Pte Ltd of Singapore. Crospovidone and povidone were obtained from BASF of Germany.

Example 1

Manufacture of Fenofibrate Nanoparticles

In this example, fenofibrate nanoparticles are manufactured according to a disclosed process and according to post-precipitation route 8a of FIG. 2. The process involves precipitating fenofibrate nanoparticles from a precipitant solution and then spray-drying the fenofibrate nanoparticles formed.

During the precipitation step, a precipitant solution containing fenofibrate was mixed with an anti-solvent solution under micro-mixing environment to form a suspension of fenofibrate nanoparticles in admixture with the excipients.

The precipitant solution was prepared by dissolving 20 g of Fenofibrate and 0.5 g of sodium lauryl sulphate (SLS) in 200 ml ethanol at a temperature of 40° C. The temperature of the solution was maintained at 35° C.

The anti-solvent solution was prepared by dissolving 76 g of Lactose, 2g of hydroxy propyl methyl cellulose (HPMC)-E3 and 1.5 g of SLS in 2000 ml water at a temperature of 25° C. The temperature of the solution was maintained at 4° C.

The precipitant solution and anti-solvent solution were introduced into the HGCP reactor 100" of FIG. 1c through liquid inlets 107a and 107b, respectively, to carry out high gravity controlled precipitation. HGCP was carried out at room temperature, that is, at a temperature of about 20 to about 23.5° C. and at atmospheric pressure. The volumetric ratio of precipitant solution to anti-solvent solution was 1:10.

The frequency of motor of the HGCP reactor 100" was set at 20 Hz such that the rotation speed of the packed bed 102 was about 2500 rpm.

After precipitation, the suspension of fenofibrate nanoparticles in admixture with the excipients was removed from the outlet conduit 106 of the HGCP reactor and immediately spray dried. A Büchi™ mini spray dryer 200 (B-290) from BÜCHI Labortechnik AG of Switzerland as shown in FIG. 2 was used. The spray drying conditions were set as follows: 0.7 mm nozzle; inlet temperature of the drying gas was 150° C.; atomizing rate was 600 L/hr; aspirator was set at 100%; and peristaltic pump rate was set at 10 ml/min.

The resultant spray dried fenofibrate nanoparticles in admixture with the excipients were removed from the collector of the spray dryer 200 in a powder form. The yield of the fenofibrate nanoparticles before and after the spray drying step is 100% and 90~100%, respectively. The fenofibrate nanoparticles in admixture with the excipients before and after spray drying were characterized using a Field Emission Scanning Electron Microscope (FESEM), a Dynamic Light Scattering (DLS) Particle Size Analyzer, a Differential Scanning calorimetry (DCS) and an USP Dissolution Apparatus 2.
Field Emission Scanning Electron Microscope (FESEM)

The samples to be examined were mounted on aluminium sample studs using double-sized carbon tapes and sputtered coated with gold at 50 mA for 50 seconds. The particle size and morphology were then observed using a field emission gun scanning electron microscope (FESEM) at 10 kV.

Figure 4A:
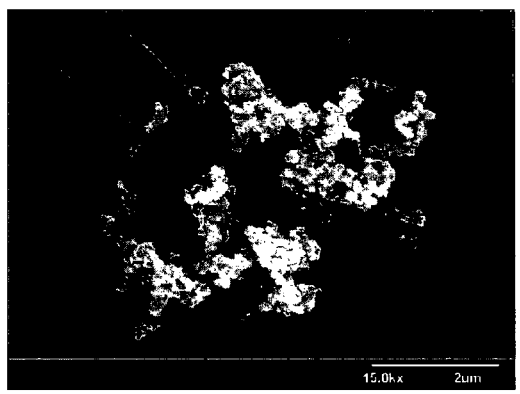
FIG. 4a and FIG. 4b are Field Emission gun Scanning Election Microscopic (FESEM) images obtained at 15,000× and 45,000× magnification; respectively, of precipitated fenofibrate nanoparticles.
Figure 4B:
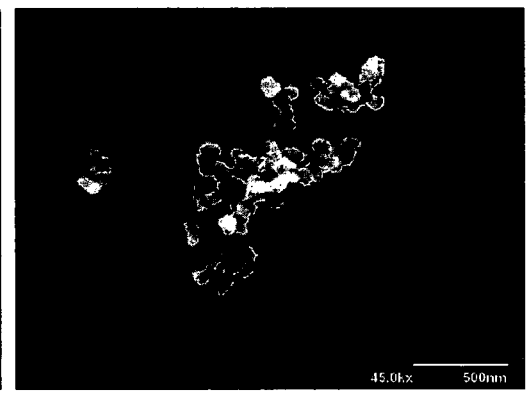

FIG. 4a and FIG. 4b are FESEM images at respective magnification at 15 000× and 45 000× of fenofibrate nanoparticles in the suspension after the precipitation step. It can be seen from these figures that the fenofibrate nanoparticles are in the nanometer range.

Figure 5A:
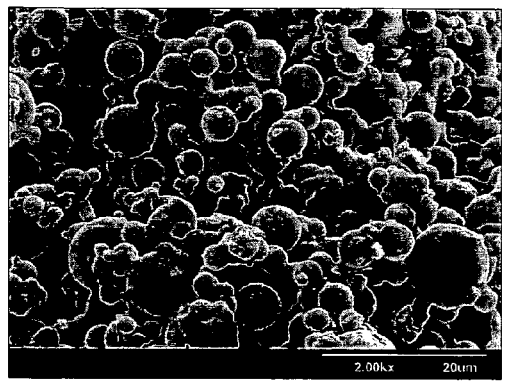
FIG. 5a is a FESEM image obtained at 2,000× magnification of processed spray-dried powder fenofibrate nanoparticles.
Figure 5B:
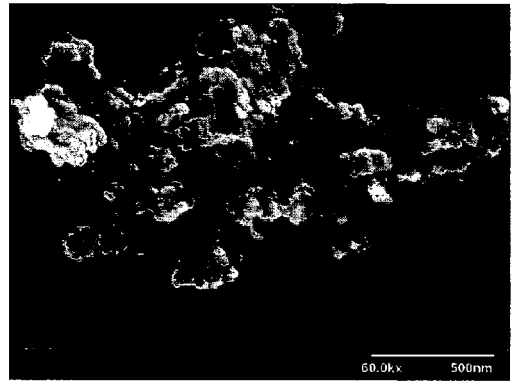
FIG. 5b is a FESEM image obtained at 60,000× magnification of the processed spray-dried powder fenofibrate nanoparticles of FIG. 5a that were redispersed in water.

FIG. 5a is a FESEM image obtained at 2,000× magnification of processed spray-dried powder fenofibrate nanoparticles. FIG. 5b is a FESEM image obtained at 60,000× magnification of the processed spray-dried powder fenofibrate nanoparticles of FIG. 5a that were redispersed in water.

FIG. 5a shows that fenofibrate nanoparticles and excipients are formed as micron-sized matrix particles. FIG. 5b shows fenofibrate nanoparticles that are nanodispersed in the matrix particles.

Figure 6:
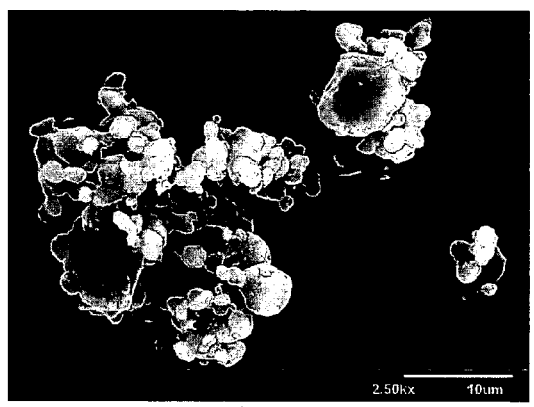
FIG. 6 is a FESEM image obtained at 2,500× magnification of micron-sized fenofibrate particles that were not obtained according to a disclosed embodiment.

FIG. 6 is a FESEM image obtained at 2,500× magnification of micron sized fenofibrate particles that were not obtained according to a disclosed process. The fenofibrate particles in FIG. 6 are commercially-available micron sized fenofibrate API. Normally, it is obtained by milling process.
Dynamic Light Scattering (DLS) Particle Size Analyzer Two samples were tested using the DLS Particle Size Analyzer from Horiba, LB-550. The first sample (Sample A) is an aliquot of the suspension of fenofibrate nanoparticles in admixture with the excipients that was obtained after the precipitation step. The second sample (Sample B) is the redispersed powder fenofibrate nanoparticles.

For Sample A, 0.2 ml of the suspension was diluted in 2 ml of water and the diluted sample was measured in a cuvette by DLS. For Sample B, 50 mg of the dried powder was ultrasonically dispersed in 10 ml deionized water and sonicated for one minute and tested using DLS Particle Size Analyzer. The results of this analysis are shown in FIG. 7 and in Table 1 below.

Figure 7:
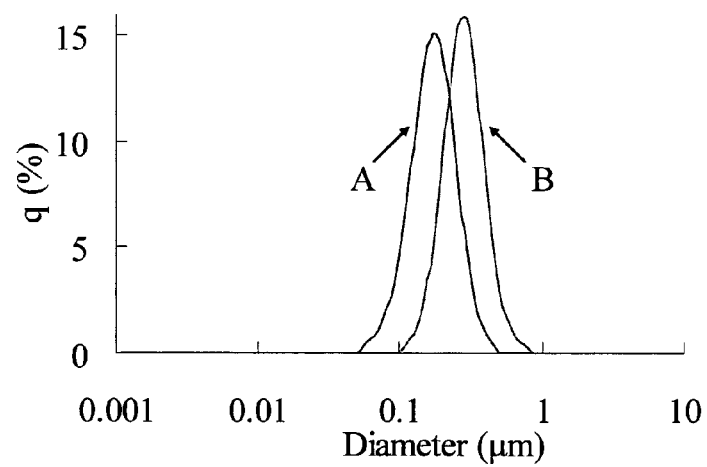
FIG. 7 is a graph of the particle size distribution of precipitated fenofibrate nanoparticles (A) and of spray-dried fenofibrate nanoparticles that were redispersed in water (B).

FIG. 7 is a graph of the particle size distribution obtained from the DLS Particle Size Analyzer. The y-axis indicates the percentage of fenofibrate nanoparticles (volume %) that corresponds to the diameter (in μm) on the x-axis. It can be seen from FIG. 7 that the diameter of the fenofibrate nanoparticles from Sample B is greater than that of the fenofibrate nanoparticles from Sample A.

TABLE 1

| Sample | Mean Size (μm) | D10 (μm) | D50 (μm) | D90 (μm) |
| --- | --- | --- | --- | --- |
| Suspension after precipitation (A) | 0.1718 | 0.1001 | 0.1630 | 0.2549 |
| Powder redispersion in water (B) | 0.4021 | 0.1757 | 0.2701 | 0.4581 |

As seen from Table 1, the particle size of the fenofibrate nanoparticles in Sample A is smaller than that of the fenofibrate nanoparticles in Sample B. The results of FIG. 7 and Table 1 may indicate that the excipients function to form a matrix that surrounds or encapsulates the substantially individualized fenofibrate nanoparticles that are dispersed therein. Therefore, without being bound by theory, it is thought that the spray drying step aids in the formation of the matrix as well as the encapsulation of the nanodispersed fenofibrate nanoparticles by the matrix. This increase in the particle size between Sample A and Sample B could be due to drying process where some fenofibrate nanoparticles fused together or aggregated together.

Differential Scanning Calorimetry (DSC) Analysis

About 5 mg sample of the powder obtained after the spray drying step was loaded into an aluminium pan and analyzed using a DSC, with a heating rate of 10° C./min from 30° C. to 120° C. A dry nitrogen purge of 60 ml/min was employed to provide an inert atmosphere to inhibit oxidation of the fenofibrate drug upon heating.

Figure 8A:
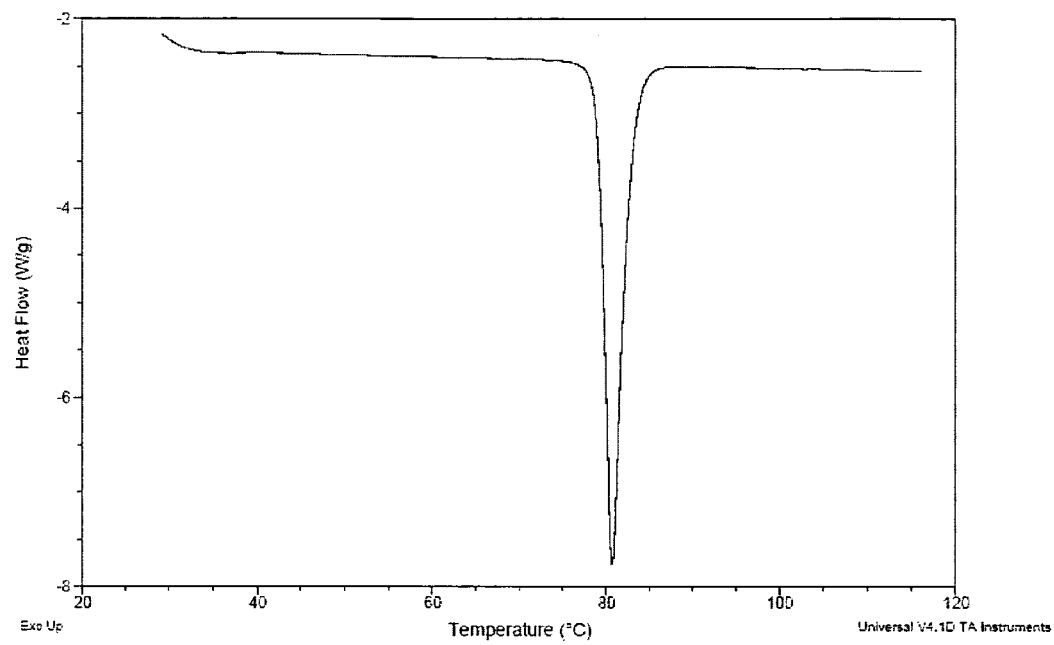
FIG. 8a, FIG. 8b and FIG. 8c are graphs showing the thermal spectra of the fenofibrate samples obtained from a Differential Scanning calorimetry (DSC).
Figure 8B:
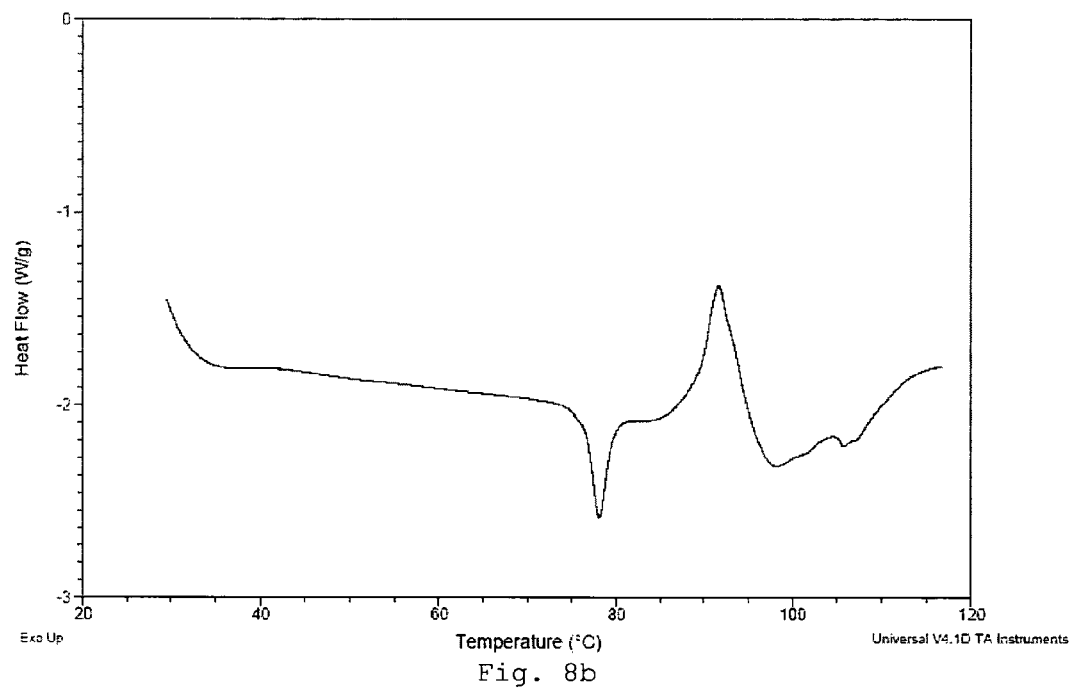
Figure 8C:
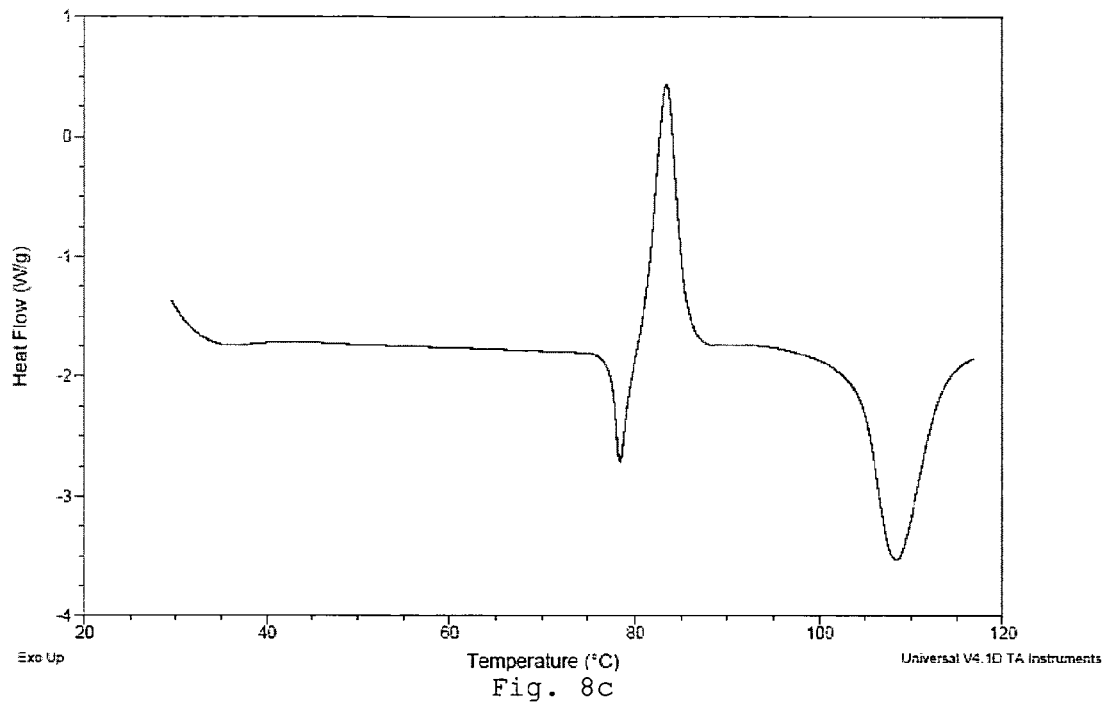

The results of this test are shown in FIGS. 8a, 8b and 8c. FIG. 8a is obtained from commercially available micron-sized unprocessed fenofibrate (API). This micron-sized fenofibrate was obtained via milling. FIG. 8b is obtained from fenofibrate powder after the spray-drying step. The amount and type of excipients used in the precipitant and anti-solvent solutions to make the fenofibrate nanoparticles are shown in Table 2 below under sample number 1. FIG. 8c was obtained from spray-drying a mixture of the micro-sized fenofibrate particles of FIG. 8a with excipients in water. The micro-sized fenofibrate particles and excipients were homogenized for 2 minutes before spray-drying. The type of excipients used is also shown in Table 2 below under sample number 2. The spray drying conditions was set as: inlet temperature: 150° C.; nitrogen flow rate: 40 mm; Pump rate: 30%; and aspirator: 100%.

TABLE 2

| | Solvent system | | | Antisolvent system | | |
| --- | --- | --- | --- | --- | --- | --- |
| Sample No. | Wt. of Drug (g) | Vol. of Solvent (ml) | T (° C.) | Wt. of Excipients (g) | Vol. of water (ml) | T (° C.) |
| 1 | 0.2 | 0.005 g SLS 2 ml Ethanol | ~35 | 0.3 g Lactose 0.02 g HPMC E3 0.015 g SLS | 20 | 5~10 |
| 2 | 0.2 | NA | | 0.3 g Lactose 0.02 g HPMC E3 0.02 g SLS | 20 | 5~10 |

Dissolution Characteristic Analysis

The same samples as those used in the above DSC Analysis were analyzed here for their inherent dissolution properties.

For each sample, 145 mg of fenofibrate particles was added to 1000 ml of USP simulated gastric fluid without enzymes (pH of 1.2) with 0.3% SLS as the dissolution medium. The temperature of the solution was maintained at 37° C. (±0.5° C.) to mimic the conditions in the stomach. The speed of the USP Dissolution Apparatus 2 (Paddle) was set at 50 rpm. At specific time intervals of 2.5 minutes, 5 minutes, 10 minutes, 15 minutes, 20 minutes, 30 minutes, 45 minutes and 60 minutes, a 5 ml aliquot was removed and filtered through a 0.22 μm syringe filter. The concentration of fenofibrate in the dissolution medium was then determined by comparing the raw value to a known standard solution using a High Performance Liquid Chromatography (HPLC) from Shimadzu-Prominence HPLC System.

Figure 9:
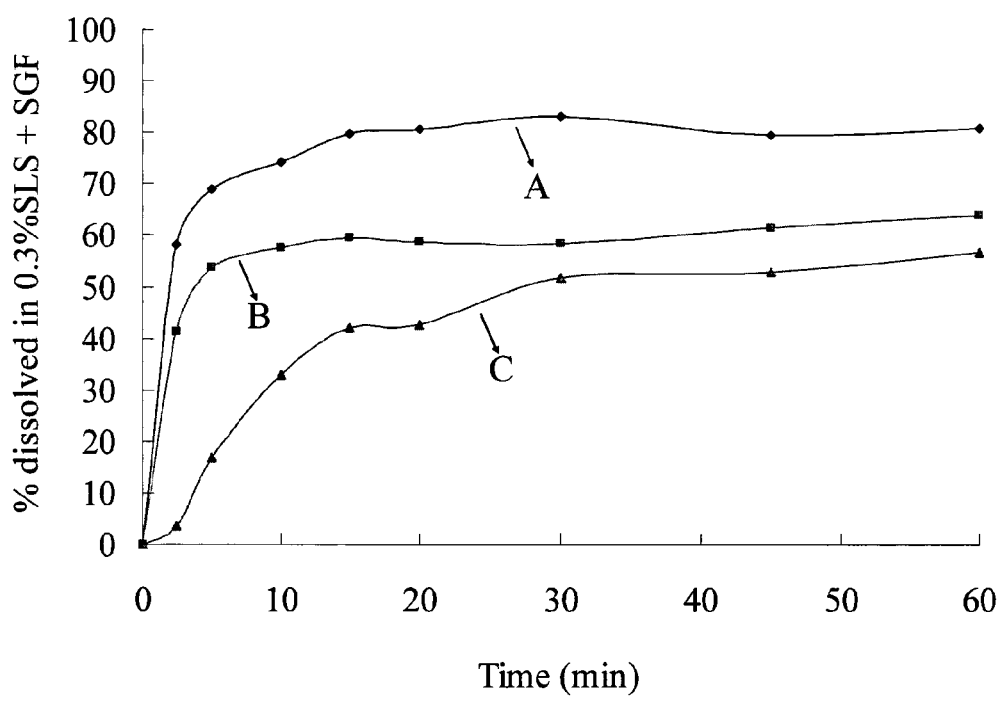
FIG. 9 shows the dissolution profiles of three fenofibrate samples as a function of time. Sample A refers to fenofibrate particles that were made according to a disclosed embodiment. Sample B refers to spray dried micron-sized fenofibrate particles that were physically mixed with excipients in water. Sample C refers to micron-sized fenofibrate.

The result of this test is shown in FIG. 9, which is a graph showing the percentage of fenofibrate dissolved in the dissolution medium as a function of time. Sample A refers to fenofibrate particles that were made according to a disclosed embodiment. Sample B refers to spray dried micron-sized fenofibrate particles that were physically mixed with excipients in water. Sample C refers to micron-sized fenofibrate.

From FIG. 9, the advantage of nanoparticles of fenofibrate can be seen in the dissolution test compared to the microparticles of fenofibrate. The nanodispersed fenofibrate powder sample made by a disclosed process has higher dissolution rate and extent compared to the micron-sized fenofibrate powder sample in the discriminatory medium. Therefore, by using the disclosed process to make nanodispersed fenofibrate powder sample that is suitable to be made into an oral solid dosage form, a greater amount of fenofibrate will be available to a patient at a faster rate upon ingestion.

Example 2

Manufacture of Lopinavir Nanoparticles

In this example, Lopinavir nanoparticles are manufactured according to a disclosed process and according to post-precipitation route 8a of FIG. 2. The process involves precipitating Lopinavir nanoparticles from a precipitant solution and then spray-drying the Lopinavir nanoparticles formed.

During the precipitation step, a precipitant solution containing Lopinavir was mixed with an anti-solvent solution under conditions of high shear and high gravity to form a suspension of Lopinavir nanoparticles in admixture with the excipients.

The precipitant solution was prepared by dissolving 20 g of Lopinavir and 0.5 g of sodium lauryl sulphate (SLS) in 200 ml ethanol at a temperature of 40° C. The temperature of the solution was cooled down and maintained at 20° C.

The anti-solvent solution was prepared by dissolving 76 g of Lactose, 2 g of hydroxy propyl methyl cellulose (HPMC)-E3 and 1.5 g of SLS in 2000 ml water at a temperature of 25° C. The temperature of the solution was maintained at 4° C.

The precipitant solution and anti-solvent solution were introduced into the HGCP reactor 100" of FIG. 1c through liquid inlets 107a and 107b, respectively, to carry out high gravity controlled precipitation (HGCP). HGCP was carried out at room temperature, that is, at a temperature of about 20 to about 23.5° C. and at atmospheric pressure. The volumetric ratio of precipitant solution to anti-solvent solution was 1:10.

The frequency of motor of the HGCP reactor 100" (or HGCP reactor) was set at 20 Hz such that the rotation speed of the packed bed 102 was about 2500 rpm.

After precipitation, the suspension of Lopinavir nanoparticles in admixture with the excipients was removed from the outlet conduit 106 of the HGCP reactor and immediately spray dried using the Büchi™ mini, spray dryer 200 (B-290). The spray drying conditions were set as follows: 0.7 mm nozzle; inlet temperature of the drying gas was 150° C.; atomizing rate was 600 L/hr; aspirator was set at 100%; and peristaltic pump rate was set at 10 ml/min.

The resultant spray dried Lopinavir nanoparticles in admixture with the excipients were removed from the collector of the spray dryer 200 in a powder form. The yield of the Lopinavir nanoparticles before and after the spray-drying step before and after the spray-drying step is 100% and 90~100%, respectively.

The Lopinavir nanoparticles in admixture with the excipients before and after spray drying were characterized using a FESEM, a DLS Particle Size Analyzer, a DSC, a X-ray diffraction (XRD) analysis, a HPLC to determine solubility and an USP Dissolution Apparatus 2.

FESEM

The samples to be examined were mounted on aluminium sample studs using double-sized carbon tapes and sputtered, coated with gold at 50 mA for 50 seconds. The particle size and morphology were then observed using a field emission gun scanning electron microscope (FESEM) at 10 kV.

Figure 10A:
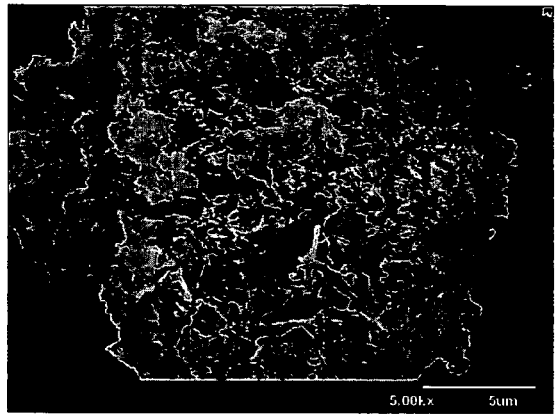
FIGS. 10a and 10b are FESEM images obtained at 5,000× and 20,000× magnification, respectively, of micron sized crystal Lopinavir that was not obtained according to a disclosed embodiment.
Figure 10B:
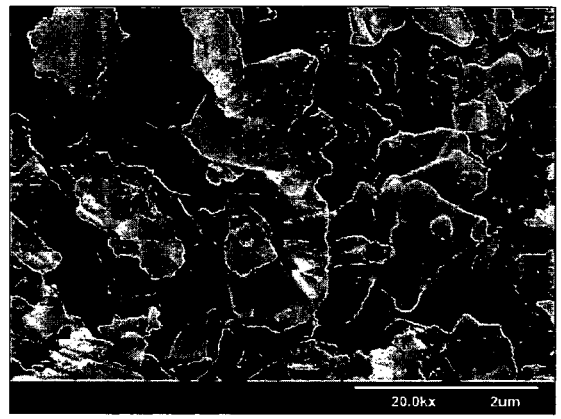
Figure 10C:
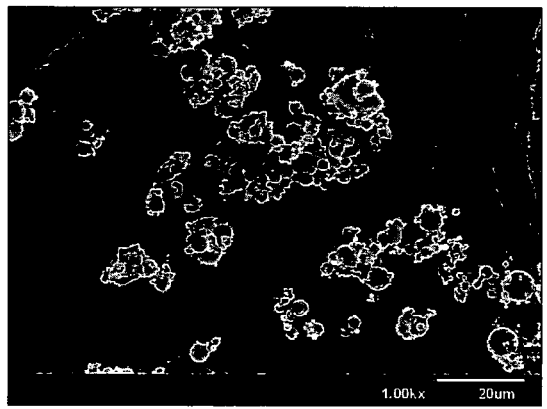
FIGS. 10c and 10d are FESEM images obtained at 1,000× and 5,000× magnification, respectively, of micron-sized amorphous Lopinavir that was not obtained according to a disclosed embodiment.
Figure 10D:
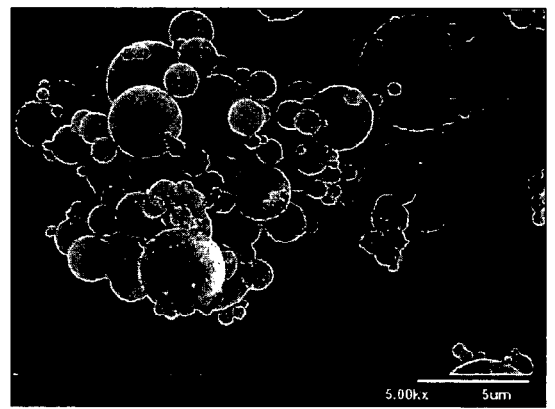

FIG. 10a and FIG. 10b are FESEM images at respective magnification at 5 000× and 20 000× of micron-sized crystal Lopinavir particles that were not obtained according to a disclosed process. These Lopinavir particles were commercially available and were made by milling. FIG. 10c and FIG. 10d are FESEM images at respective magnification at 1 000× and 5 000× of micron-sized amorphous Lopinavir particles that were not obtained according to a disclosed process. The Lopinavir particles were obtained by spray-drying the commercially available Lopinavir particles in an ethanol solution.

Figure 11A:
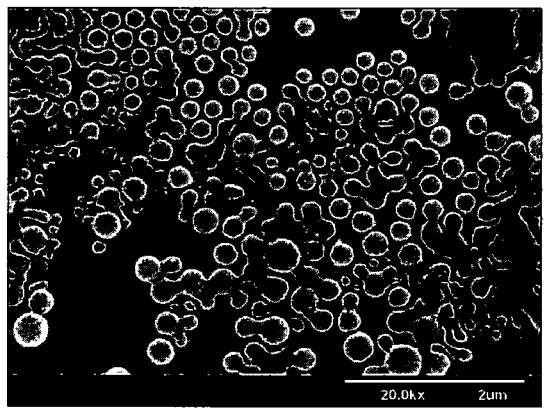
FIGS. 11a and 11b are FESEM images obtained at 20,000× and 40,000× magnification, respectively, of precipitated Lopinavir nanoparticles.
Figure 11B:
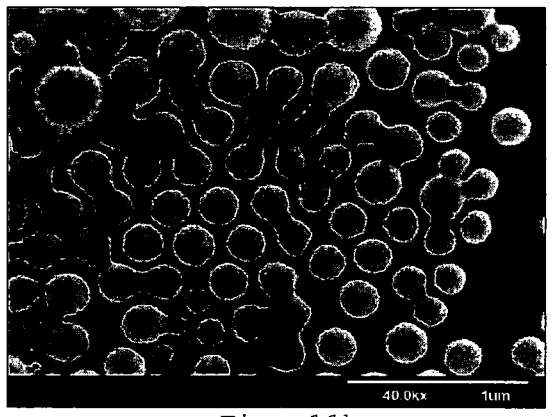

FIG. 11a and FIG. 11b are FESEM images at respective magnification at 20 000× and 40 000× of Lopinavir nanoparticles in the suspension after the precipitation step. It can be seen from these figures that the Lopinavir nanoparticles are in the nanometer range.

Figure 12A:
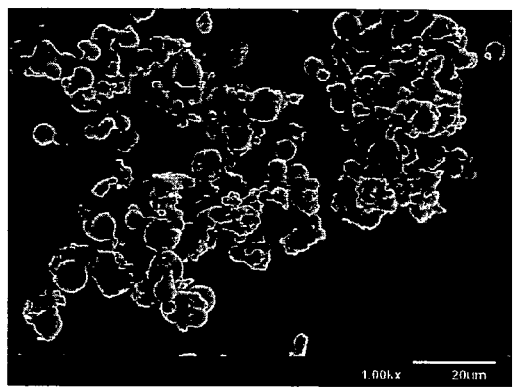
FIGS. 12a and 12b are FESEM images obtained at 1,000× and 5,000× magnification, respectively, of processed spray-dried powder of Lopinavir nanoparticles.
Figure 12B:
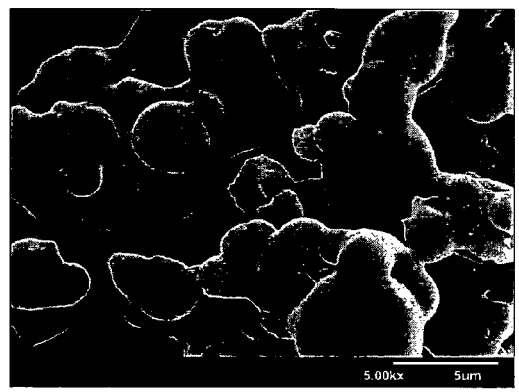

FIGS. 12a and 12b are FESEM images obtained at 1,000× and 5,000× magnification, respectively, of processed spray-dried powder Lopinavir nanoparticles. From these figures, it can be seen that the nanoparticles are dispersed and separated very well in the matrix particles after the spray drying process.

Figure 13A:
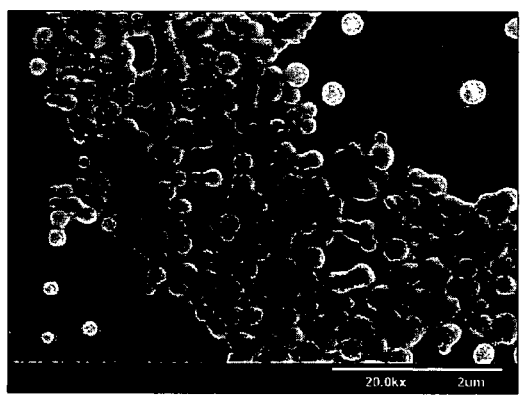
FIGS. 13a and 13b are FESEM images obtained at 20,000× and 40,000× magnification, respectively, of processed spray-dried powder lopinavir nanoparticles of FIGS. 12a and 12b that were redispersed in water.
Figure 13B:
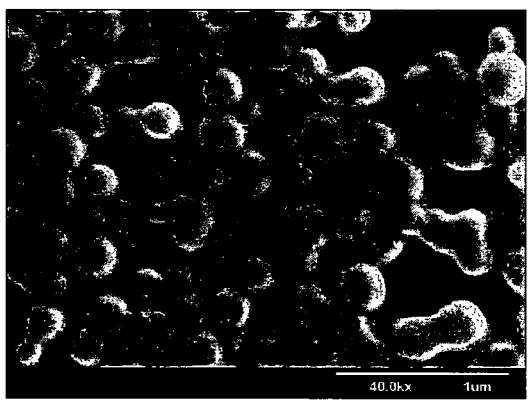

FIG. 13a and FIG. 13b are FESEM images of processed spray-dried powder lopinavir nanoparticles of FIGS. 12a and 12b that were redispersed in water. FIG. 13a was obtained at a magnification of 20,000× and FIG. 13b was obtained at a magnification of 40,000×. FIG. 13b shows that upon redispersion in water, the Lopinavir nanoparticles are nanodispersed particles that do not substantially aggregate or clump together with each other. Without being bound by theory, this could be due to the presence of the excipients which form a matrix. The matrix surrounds the nanoparticles that are dispersed in the matrix such that the nanoparticles are substantially prevented from agglomerating or coagulating with each other.

DLS Particle Size Analyzer

Two samples were tested using the DLS Particle Size Analyzer. The first sample (Sample A) is an aliquot of the suspension of Lopinavir nanoparticles in admixture with the excipients that was obtained after the precipitation step. The second sample (Sample B) is the redispersed powder Lopinavir nanoparticles.

For Sample A, 0.2 ml of the suspension was diluted 10 times with 2 ml water and the diluted sample was measured in a cuvette using DLS. For Sample B, 50 mg of the dried powder was ultrasonically dispersed in 10 ml deionized water, sonicated for one minute and tested using a DLS. The results of this analysis are shown in FIG. 14 and in Table 3 below.

Figure 14:
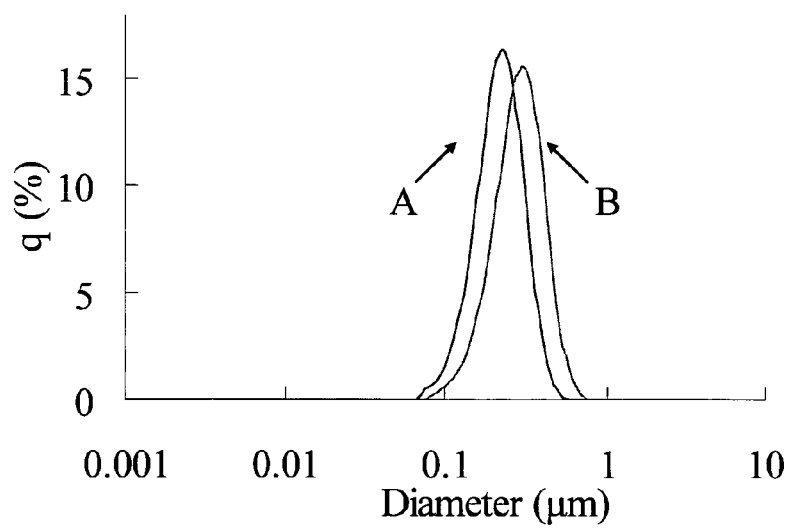
FIG. 14 is a graph of the particle size distribution of precipitated Lopinavir nanoparticles (A) and of spray-dried powder of Lopinavir nanoparticles that were redispersed in water (B).

FIG. 14 is a graph of the particle size distribution obtained from the DLS Particle Size Analyzer of precipitated Lopinavir nanoparticles (A) and of spray-dried powder of Lopinavir nanoparticles that were redispersed in water (B). The y-axis indicates the percentage of Lopinavir nanoparticles (volume %) that corresponds to the diameter (in μm) on the x-axis. It can be seen from FIG. 14 that the diameter of the Lopinavir nanoparticles from Sample B is greater than that of the Lopinavir nanoparticles from Sample A.

TABLE 3

| Sample | Mean Size (μm) | D10 (μm) | D50 (μm) | D90 (μm) |
|---|---|---|---|---|
| Suspension after precipitation (A) | 0.2136 | 0.1298 | 0.2060 | 0.3086 |
| Powder redispersion in water (B) | 0.2805 | 0.1638 | 0.2705 | 0.4116 |

As seen from Table 3, the particle size of the Lopinavir nanoparticles in Sample B is not significantly greater than that of the Lopinavir nanoparticles in Sample A. The results of FIG. 14 and Table 3 may indicate that the excipients function to form a matrix that surrounds or encapsulates the substantially individualized Lopinavir nanoparticles that are dispersed therein. The matrix particles are in the micro-sized range. Without being bound by theory, it is thought that the spray drying step aids in the formation of the matrix as well as the encapsulation of the nanodispersed, discrete, individualised Lopinavir nanoparticles by the excipients that form the bulk of the matrix particle. The spray drying step may aid to remove solvent and hence prevents particle growth of the drug nanoparticles.

DSC Analysis

About 5 mg sample of the powder obtained, after the spray drying step was loaded into an aluminium pan and analyzed using a DSC, with a heating rate of 10° C./min from 30° C. to 150° C. A dry nitrogen purge of 60 ml/min was employed to provide an inert atmosphere to inhibit oxidation of the Lopinavir drug upon heating.

Figure 15A:
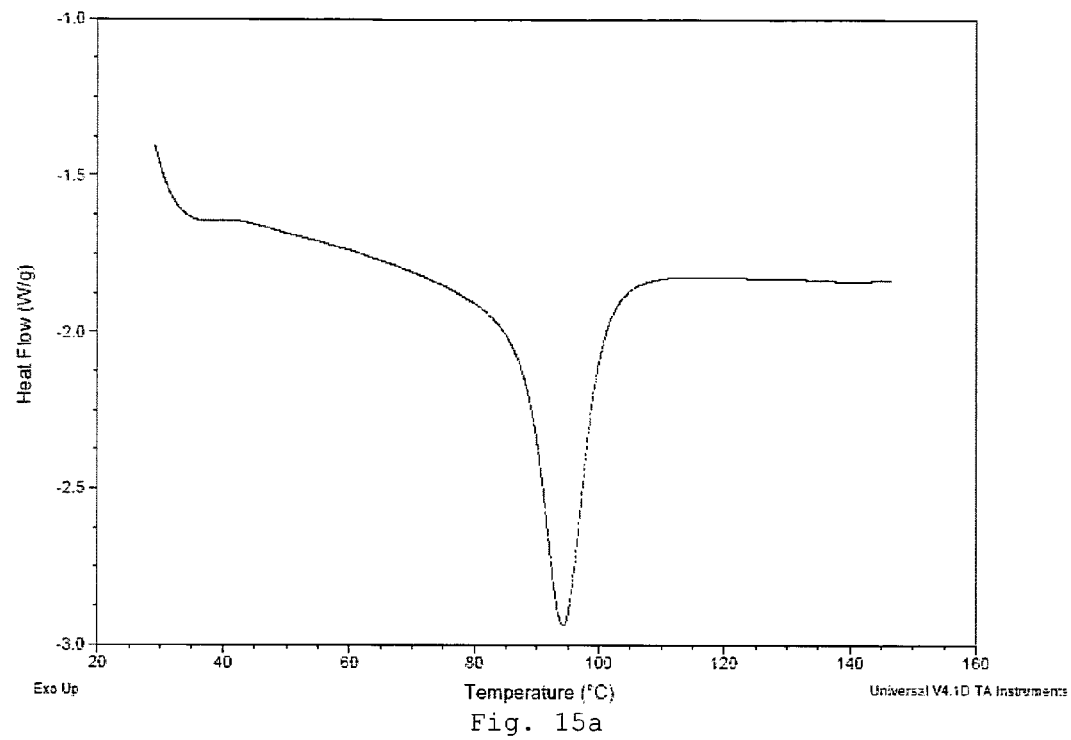
FIG. 15a, FIG. 15b and FIG. 15c are graphs showing the thermal spectra of the Lopinavir samples obtained from a DSC.
Figure 15B:
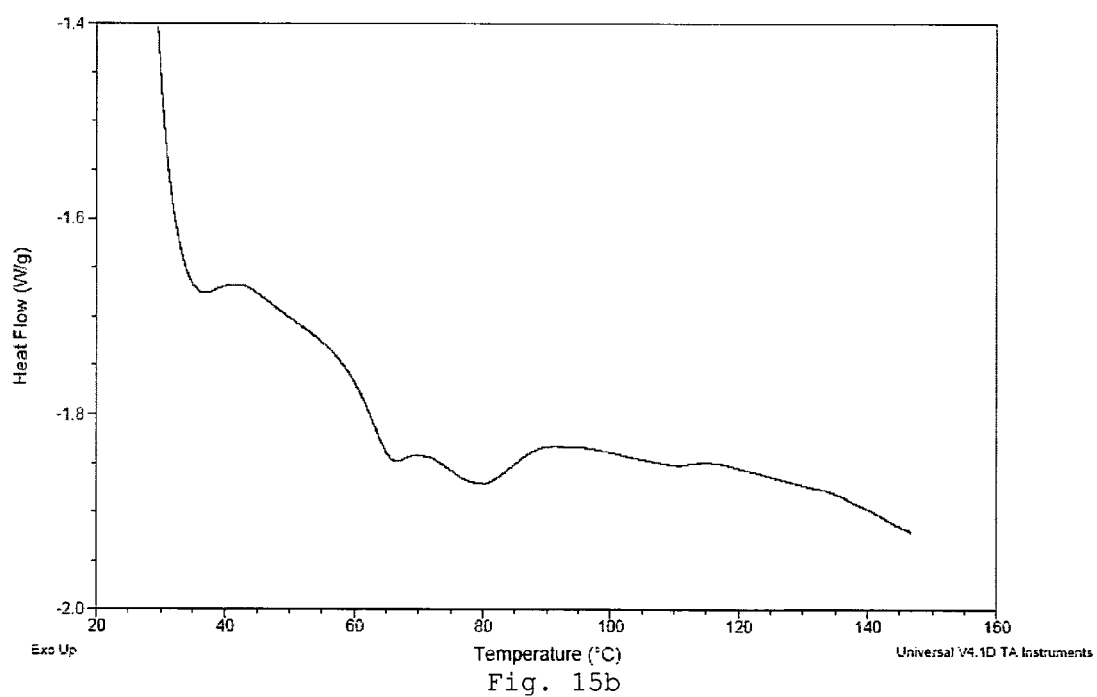
Figure 15C:
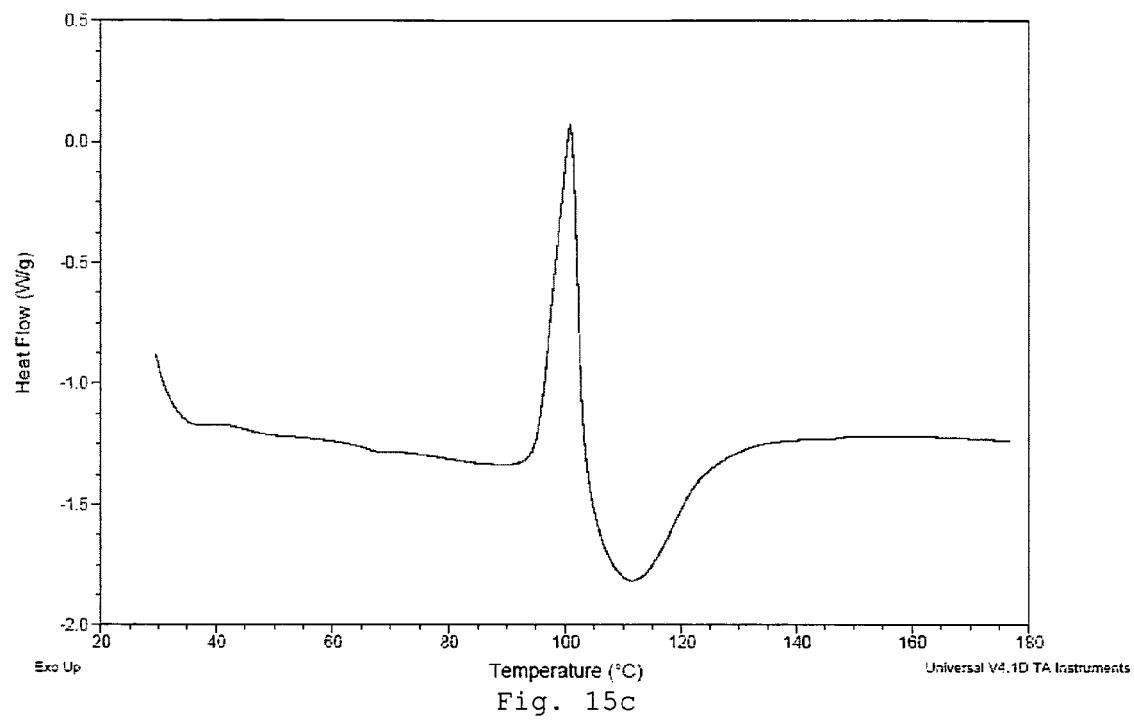

The results of this test are shown in FIGS. 15a, 15b and 15c. FIG. 15a was obtained from analyzing commercially available micro-sized crystalline Lopinavir. FIG. 15b was obtained from analyzing spray dried micro-sized amorphous Lopinavir in an ethanol solution. FIG. 15c was obtained from analyzing spray-dried Lopinavir powder that had been obtained in this example. FIG. 15c shows that the Lopinavir powder obtained from this example are of the amorphous form.

X-Ray Diffraction (XRD) Analysis

The crystallinity of the Lopinavir nanoparticles made in this Example was investigated using XRD from X'pert, Philips, using CuK α radiation at a scanning speed of 0.1 o/s across a range of 5° to 40°.

Figure 15D:
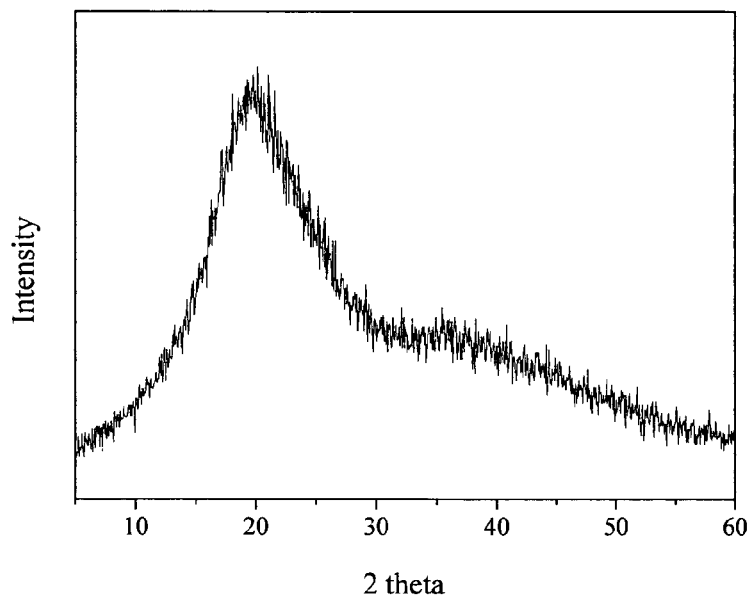
FIG. 15d is a X-ray diffraction (XRD) spectrum of the amorphous powder lopinavir nanoparticles of FIG. 15c.

FIG. 15d is the XRD spectrum of the lopinavir particles used in FIG. 15c. FIG. 15d shows that the Lopinavir particles from this Example were in the amorphous form.

Solubility Test

Five samples were used in this solubility test. For each sample, 37.5 mg of sample was dissolved in 250 ml water. The test solution was stirred at 500 rpm using a magnetic stirrer for 1 hour at room temperature, that is, at a temperature of about 20 to about 23.5° C. At each time point of 1, 2.5, 5, 10, 20, 30, 45 and 60 minutes, an aliquot of 5 ml was removed from the test solution, filtered to remove undissolved Lopinavir particles using a 0.22 µm filter and tested using a HPLC.

Figure 16:
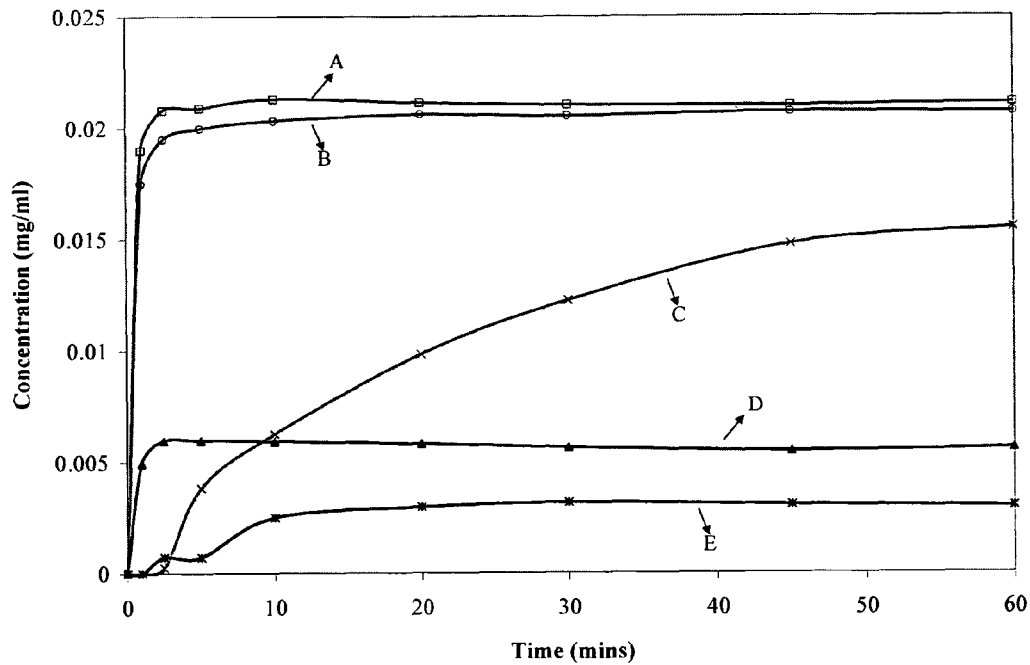
FIG. 16 shows the solubility profiles of five Lopinavir samples as a function of time. Sample A refers to spray-dried Lopinavir powder that was prepared according to a disclosed embodiment. Sample B refers micron sized amorphous Lopinavir that had been physically mixed with excipients. Sample C refers to micron sized amorphous Lopinavir. Sample D refers to micron sized crystal Lopinavir that had been physically mixed with excipients. Sample E refers to micron sized crystal Lopinavir.

FIG. 16 shows the solubility profile of the five samples. Sample A is processed Lopinavir powder that was prepared according to this Example and according to the excipient amounts as shown in Table 4. Sample B is micron-sized amorphous Lopinavir that had been physically mixed with excipients according to Table 4. Sample C is micron-sized amorphous Lopinavir. Sample C was prepared by dissolving 2.5 g Lopinavir in 50 ml ethanol and then filtered through 0.45 µm filter paper. The solution was then spray dried according to the conditions: nozzle diameter of 0.7 mm; inlet temperature of 100° C.; nitrogen flow rate of 35 mm; aspirator of 100%; and pump rate of 25%. The dried powder was then subjected to the solubility test as described above. Sample D is micron-sized crystalline Lopinavir that had been physically mixed with excipients according to Table 4. Sample E is commercially available micron-sized crystalline Lopinavir.

TABLE 4

| | Solvent system | | | Antisolvent system | | |
|---|---|---|---|---|---|---|
| Sample No. | Wt. of Drug (g) | Vol. of Solvent (ml) | Temp (° C.) | Wt. of Excipients (g) | Vol. of water (ml) | Temp (° C.) |
| A | 0.1 | 0.0025 g SLS 1 ml Ethanol | Room temp | 0.4 g Lactose 0.01 g HPMC E3 0.0075 g SLS | 10 | 5~10 |
| B | 0.1 of sample C | | | 0.4 g Lactose 0.01 g HPMC E3 0.01 g SLS | 10 | 5~10 |
| D | 0.1 sample E | | | 0.4 g Lactose 0.01 g HPMC E3 0.01 g SLS | 10 | 5~10 |

Figure 17:
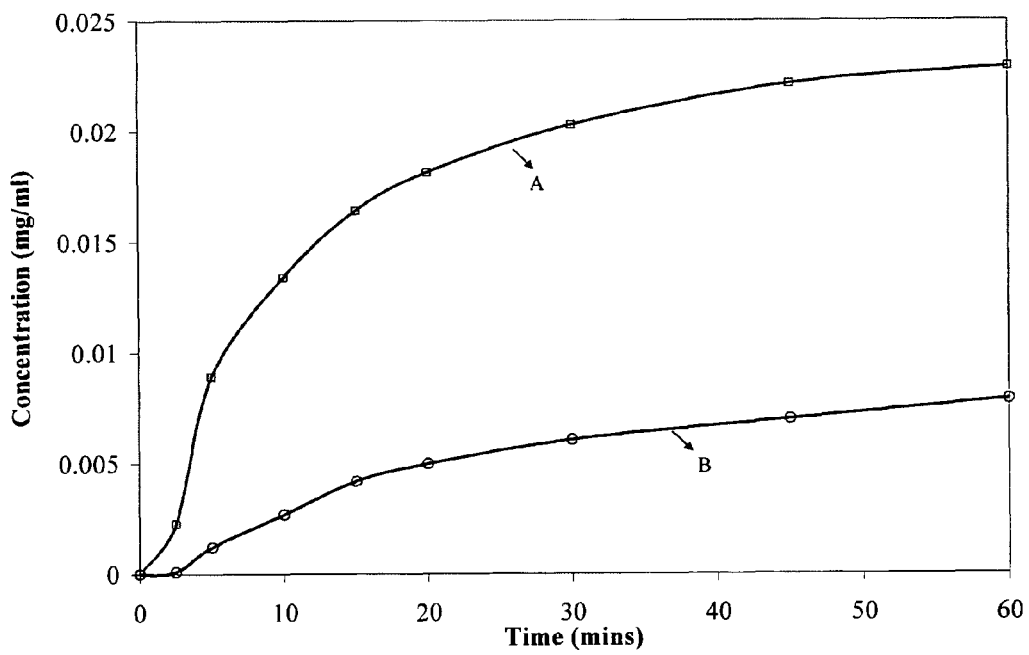
FIG. 17 shows the dissolution profiles of two Lopinavir samples as a function of time. Sample A refers to spray-dried Lopinavir powder that was prepared according to a disclosed embodiment. Sample B refers micron sized amorphous Lopinavir that had been physically mixed with excipients.

FIG. 16 shows that amorphous form has higher solubility in water compared to the crystal form. For some very poorly water-soluble drugs, maintaining particles in the amorphous form in the solid dosage forms can help improve the bioavailability of this drug in patient's body. The disclosed process resulted in a Lopinavir sample (Sample A) in which the Lopinavir nanoparticles maintain their amorphous form in the matrix particles. The result of the solubility test on Sample A and Sample B shows that solubility is not related with particle size. This means that solubility is only related with drug's polymorphic form (FIG. 16). Particle size will not influence drug's solubility, but will influence the dissolution rate which may influence bioavailability in patients (FIG. 17).

Dissolution Characteristic Analysis

Two samples were analyzed here for their inherent dissolution properties. Sample A and Sample B are the same as those used in the above solubility test.

For each sample, 40 mg of Lopinavir particles was added to 900 ml of pure deionised water as the dissolution medium. The temperature of the solution was maintained at 37° C. (±0.5° C.). The speed of the USP Dissolution Apparatus 2 (Paddle) was set at 75 rpm. At specific time intervals of 2.5 minutes, 5 minutes, 10 minutes, 15 minutes, 20 minutes, 30 minutes, 45 minutes and 60 minutes, a 5 ml aliquot was removed and filtered through a 0.22 µm syringe filter. Then, the concentration of Lopinavir in the dissolution medium was determined by comparing the raw value to a known standard solution using a High Performance Liquid Chromatography (HPLC).

The result of this test is shown in FIG. 17, which is a graph showing the percentage of Lopinavir dissolved in the dissolution medium as a function of time. From FIG. 17 and FIG. 16, it can be seen that although Sample A and Sample B have the same solubility due to their same amorphous form, the dissolution rate and extent of the processed Lopinavir sample in Sample A are much higher than those of Sample B, under the tested time conditions. Hence, the advantage of nanoparticulate Lopinavir powder sample of an amorphous form compared to the conventional amorphous micron-sized Lopinavir powder sample is the increased dissolution effect.

Example 3

Manufacture of Cefuroxime Axetil (CFA) Nanoparticles

In this example, CFA nanoparticles are manufactured according to a disclosed process and according to post-precipitation route 8a of FIG. 2. The process involves precipitating CFA nanoparticles from a precipitant solution and then spray-drying the CFA nanoparticles formed.

During the precipitation step, a precipitant solution containing CFA was mixed with an anti-solvent solution under conditions of high shear and high gravity to form a suspension of CFA nanoparticles in admixture with the excipients.

The precipitant solution was prepared by dissolving 20 g of CFA and 0.5 g of sodium lauryl sulphate (SLS) in 100 ml ethanol/acetone (in a ratio of 1:3) at a temperature of 40° C. The temperature of the solution was cooled down and maintained at 20° C.

The anti-solvent solution was prepared by dissolving 76 g of Lactose, 4 g of hydroxy propyl methyl cellulose (HPMC)-E3 and 1.5 g of SLS in 1000 ml water at a temperature of 25° C. The temperature of the solution was maintained at 4° C.

The precipitant solution and anti-solvent solution were introduced into the HGCP reactor 100" of FIG. 1c through liquid inlets 107a and 107b, respectively, to carry out high gravity controlled precipitation (HGCP). HGCP was carried out at room temperature, that is, at a temperature of about 20 to about 23.5° C. and at atmospheric pressure. The volumetric ratio of precipitant solution to anti-solvent solution was 1:10

The frequency of motor of the HGCP reactor 100" (or HGCP reactor) was set at 20 Hz such that the rotation speed of the packed bed 102 was about 2500 rpm.

After precipitation, the suspension of CFA nanoparticles in admixture with the excipients was removed from the outlet conduit 106 of the HGCP reactor and immediately spray dried using the Büchi™ mini spray dryer 200 (B-290). The spray drying conditions were set as follows: 0.7 mm nozzle; inlet temperature of the drying gas was 150° C.; atomizing rate was 600 L/hr; aspirator was set at 100%; and peristaltic pump rate was set at 10 ml/min.

The resultant spray dried CFA nanoparticles in admixture with the excipients were removed from the collector of the spray dryer 200 in a powder form. The yield of the CFA nanoparticles before and after the spray-drying step is 100% and 90~100%, respectively.

The CFA nanoparticles in admixture with the excipients before and after spray drying were characterized using a FESEM and a DLS Particle Size Analyzer.

FESEM

The samples to be examined were mounted on aluminium sample studs using double-sized carbon tapes and sputtered coated with gold at 50 mA for 50 seconds. The particle size and morphology were then observed using a field emission gun scanning electron microscope (FESEM) at 10 kV.

Figure 18A:
FIG. 18a is a FESEM image obtained at 5,000× magnification of crystalline cefuroxime axetil (CFA) that was not made according to a disclosed embodiment.

FIG. 18a is a FESEM image obtained at 5,000× magnification of crystalline cefuroxime axetil (CFA) that was not made according to a disclosed embodiment.

Figure 18B:
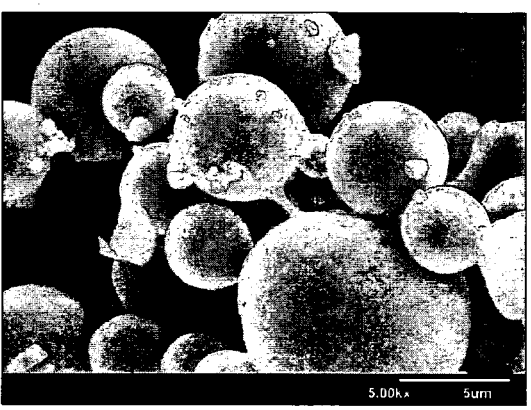
FIG. 18b is a FESEM image obtained at 5,000× magnification of spray-dried powder of CFA nanoparticles that were made according to a disclosed embodiment.

FIG. 18b is a FESEM image obtained at 5,000× magnification of spray-dried powder CFA nanoparticles that were made according to a disclosed embodiment.

Figure 19A:
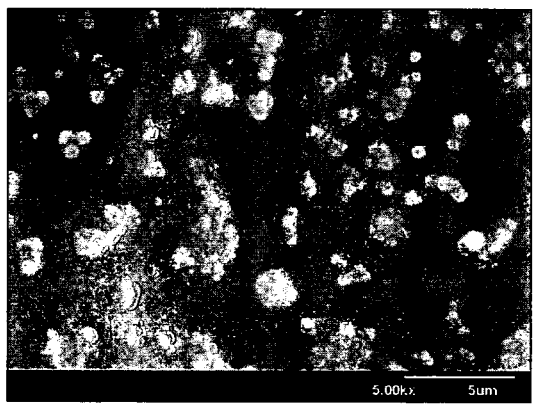
FIGS. 19a and 19b are FESEM images obtained at 5,000× and 3,000× magnification, respectively, of precipitated cefuroxime axetil (CFA) nanoparticles.
Figure 19B:
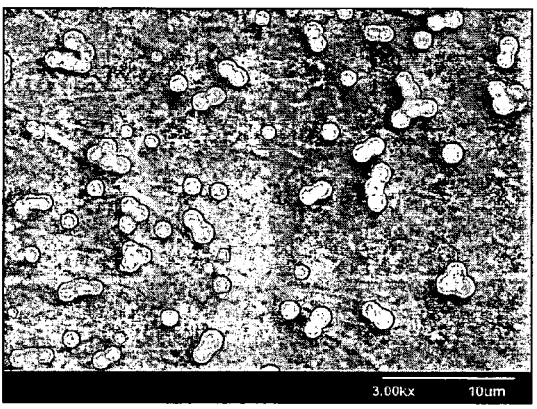

FIG. 19a and FIG. 19b are FESEM images at respective magnification at 5,000× and 3,000× of CFA nanoparticles in the suspension after the precipitation step. It can be seen from these figures that the CFA nanoparticles are in the nanometer range.

Figure 20A:
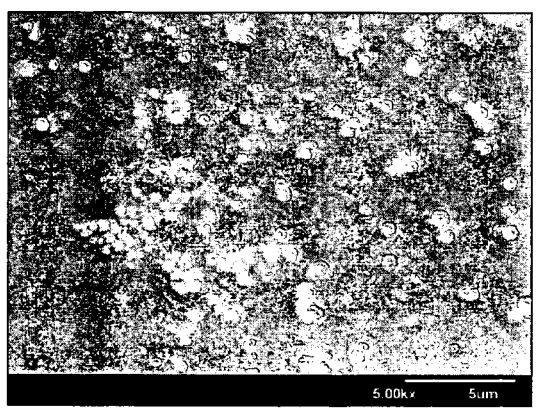
FIGS. 20a and 20b are FESEM images obtained at 5,000× and 10,000× magnification, respectively, of spray-dried CFA nanoparticles that are redispersed in water.
Figure 20B:
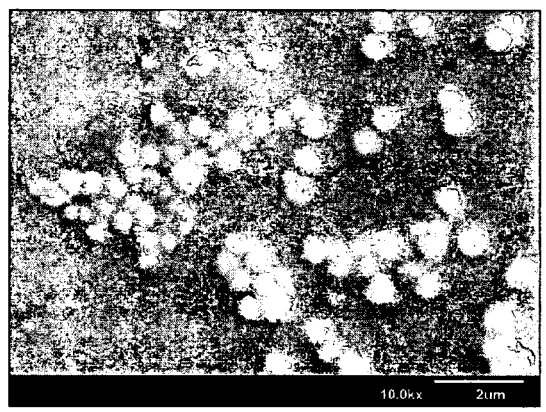
Figure 21:
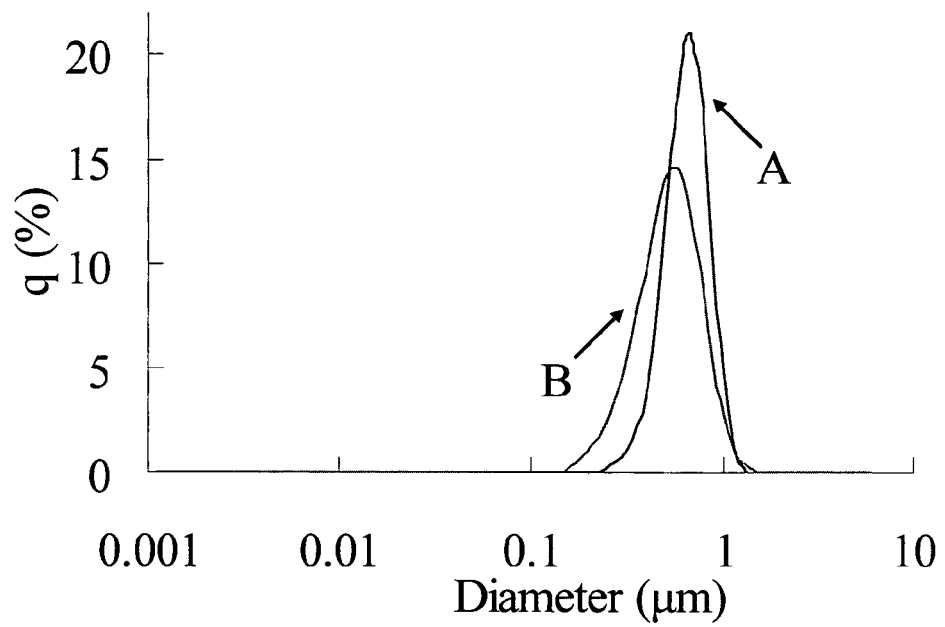
FIG. 21 is a graph of the particle size distribution of precipitated CFA nanoparticles (A) and of spray-dried CFA nanoparticles that were redispersed in water (B).

FIG. 20a and FIG. 20b are FESEM images of spray-dried powder CFA nanoparticles that were redispersed in water. FIG. 20a was obtained at a magnification of 5,000× and FIG. 20b was obtained at a magnification of 10,000×. FIG. 20a and FIG. 20b shows that upon redispersion in water, the CFA nanoparticles are discrete, individualised particles that are substantially separated from each other by an excipient-formed matrix.

DLS Particle Size Analyzer

Two samples were tested using the DLS Particle Size Analyzer. The first sample (Sample A) is an aliquot of the suspension of CFA nanoparticles in admixture with the excipients that was obtained after the precipitation step. The second sample (Sample B) is the redispersed powder CFA nanoparticles step.

Figure 22A:
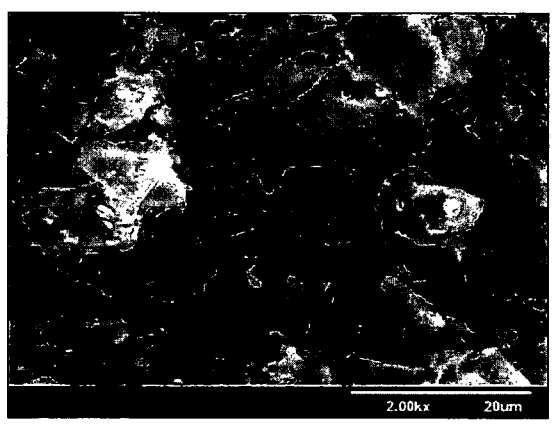
FIG. 22a is a FESEM image obtained at 2,000× magnification of crystalline cyclosporine that was not made according to a disclosed embodiment.

For Sample A, 0.2 ml of the suspension was diluted ten times with 2 ml water and the diluted sample was measured in a cuvette using DLS. For Sample B, 50 mg of the dried powder was ultrasonically dispersed in 10 ml deionized water, sonicated for one minute and tested using a DLS. The results of this analysis are shown in FIG. 21 and in Table 5 below.

FIG. 21 is a graph of the particle size distribution obtained from the DLS Particle Size Analyzer. The y-axis indicates the percentage of CFA nanoparticles (volume %) that corresponds to the diameter (in μm) on the x-axis. It can be seen from FIG. 21 that the diameter of the CFA nanoparticles from Sample B is smaller than that of the CFA nanoparticles from Sample A.

TABLE 5

| Sample | Mean Size (μm) | $D_{10}$ (μm) | $D_{50}$ (μm) | $D_{90}$ (μm) |
|---|---|---|---|---|
| Suspension after precipitation (A) | 0.6202 | 0.4200 | 0.6096 | 0.8380 |
| Powder redispersion in water (B) | 0.5178 | 0.2918 | 0.4962 | 0.7681 |

As seen from Table 5, the particle size of the CFA nanoparticles in Sample A is greater than that of the CFA nanoparticles in Sample B. One possible reason for this is that Sample A still contains solvents while it has been processed for the DLS test. Since the drug is in the amorphous state, it is highly unstable and, hence the drug tends to aggregate or grow, leading to an increased particle size. On the other hand, Sample B is the powder that had been immediately spray dried. Hence, the solvent is removed quickly and the particles retain its particle size.

Example 4

Manufacture of Cyclosporine Nanoparticles

In this example, Cyclosporine nanoparticles are manufactured according to a disclosed process and according to post-precipitation route 8*a* of FIG. 2. The process involves precipitating Cyclosporine nanoparticles from a precipitant solution and then spray-drying the Cyclosporine nanoparticles formed.

During the precipitation step, a precipitant solution containing Cyclosporine was mixed with an anti-solvent solution under conditions of high shear and high gravity to form a suspension of Cyclosporine nanoparticles in admixture with the excipients.

The precipitant solution was prepared by dissolving 20 g of Cyclosporine and 0.5 g of sodium lauryl sulphate (SLS) in 100 ml ethanol at a temperature of 40° C. The temperature of the solution was cooled down and maintained at 20° C.

The anti-solvent solution was prepared by dissolving 76 g of Lactose, 4 g of hydroxy propyl methyl cellulose (HPMC)-E3 and 1.5 g of SLS in 1000 ml water at a temperature of 25° C. The temperature of the solution was maintained at 4° C.

The precipitant solution and anti-solvent solution were introduced into the HGCP reactor 100" of FIG. 1*c* through liquid inlets 107*a* and 107*b*, respectively, to carry out high gravity controlled precipitation (HGCP). HGCP was carried out at room temperature, that is, at a temperature of about 20 to about 23.5° C. and at atmospheric pressure. The volumetric ratio of precipitant solution to anti-solvent solution was 1:10.

The frequency of motor of the HGCP reactor 100" (or HGCP reactor) was set at 20 Hz such that the rotation speed of the packed bed 102 was about 2500 rpm.

After precipitation, the suspension of Cyclosporine nanoparticles in admixture with the excipients was removed from the outlet conduit 106 of the HGCP reactor and immediately spray dried using the Büchi™ mini spray dryer 200 (B-290). The spray drying conditions were set as follows: 0.7 mm nozzle; inlet temperature of the drying gas was 150° C.; atomizing rate was 600 L/hr; aspirator was set at 100%; and peristaltic pump rate was set at 10 ml/min.

The resultant spray dried Cyclosporine nanoparticles in admixture with the excipients were removed from the collector of the spray dryer 200 in a powder form. The yield of the Cyclosporine nanoparticles before and after the spray-drying step is 100% and 90~100%, respectively.

The Cyclosporine nanoparticles in admixture with the excipients before and after spray drying were characterized using a FESEM and a DLS Particle Size Analyzer.

FESEM

The samples to be examined were mounted on aluminium sample studs using double-sized carbon tapes and sputtered coated with gold at 50 mA for 50 seconds. The particle size and morphology were then observed using a field emission gun scanning electron microscope (FESEM) at 10 kV.

FIG. 22a is a FESEM image obtained at 2,000× magnification of crystalline cyclosporine that was not made according to a disclosed embodiment.

Figure 22B:
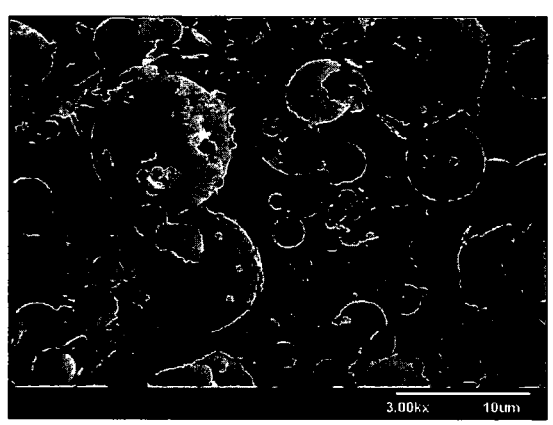
FIG. 22b is a FESEM image obtained at 3,000× magnification of spray-dried powder of cyclosporine nanoparticles that were made according to a disclosed embodiment.

FIG. 22b is a FESEM image obtained at 3,000× magnification of spray-dried powder cyclosporine nanoparticles that were made according to a disclosed embodiment.

FIG. 23a and FIG. 23b are FESEM images of spray-dried powder Cyclosporine nanoparticles that were redispersed in water. FIG. 23a was obtained at a magnification of 20,000× and FIG. 23b was obtained at a magnification of 40,000×. FIG. 23b shows that upon redispersion in water, the Cyclosporine nanoparticles are discrete, individualised particles that are substantially separated from each other by an excipient-formed matrix.

DLS Particle Size Analyzer

Two samples were tested using the DLS Particle Size Analyzer. The first sample (Sample A) is an aliquot of the suspension of Cyclosporine nanoparticles in admixture with the excipients that was obtained after the precipitation step. The second sample (Sample B) is the redispersed powder Cyclosporine nanoparticles.

For Sample A, 0.2 ml of the suspension was diluted ten times with 2 ml of deionised water and the diluted sample was measured in a cuvette using DLS. For Sample B, 50 mg of the dried powder was ultrasonically dispersed in deionized water, sonicated for one minute and analysed using DLS. The results of this analysis are shown in FIG. 24 and in Table 6 below.

FIG. 24 is a graph of the particle size distribution obtained from the DLS Particle Size Analyzer. The y-axis indicates the percentage of Cyclosporine nanoparticles (volume %) that corresponds to the diameter (in μm) on the x-axis. It can be seen from FIG. 24 that the diameter of the Cyclosporine nanoparticles from Sample B is greater than that of the Cyclosporine nanoparticles from Sample A.

TABLE 6

| Sample | Mean Size (μm) | $D_{10}$ (μm) | $D_{50}$ (μm) | $D_{90}$ (μm) |
| --- | --- | --- | --- | --- |
| Suspension after precipitation (A) | 0.1263 | 0.0694 | 0.1201 | 0.1911 |
| Powder redispersion in water (B) | 0.1785 | 0.1052 | 0.1785 | 0.2741 |

As seen from Table 6, the particle size of the Cyclosporine nanoparticles in Sample A is smaller than that of the Cyclosporine nanoparticles in Sample B. This increase in the particle size could be due to the highly unstable nature of the amorphous nanoparticles which tend to aggregate as a result of their high surface area and high energy.

Example 5

Manufacture of Bicalutamide Nanoparticles

In this example, Bicalutamide nanoparticles are manufactured according to a disclosed process and according to the post-precipitation route 8c of FIG. 2. The process involves precipitating Bicalutamide nanoparticles from a precipitant solution, filtering the suspension of Bicalutamide drug nanoparticles and then spray-drying the isolated Bicalutamide nanoparticles.

During the precipitation step, a precipitant solution containing Bicalutamide was mixed with an anti-solvent solution under conditions of high shear and high gravity to form a suspension of Bicalutamide nanoparticles in admixture with the excipients.

The precipitant solution was prepared by dissolving 20 g of Bicalutamide in 200 ml DMSO at room temperature (that is, about 20 to about 23.5° C.).

The anti-solvent solution used was made up by dissolving 30 g Lutrol F127 in 3000 ml deionised water at a temperature of 25° C.

The precipitant solution and anti-solvent solution were introduced into the HGCP reactor 100" of FIG. 1c through liquid inlets 107a and 107b, respectively, to carry out high gravity controlled precipitation (HGCP). HGCP was carried out at room temperature, that is, at a temperature of about 20 to about 23.5° C. and at atmospheric pressure. The volumetric ratio of precipitant solution to anti-solvent solution was 1:15.

The frequency of motor of the HGCP reactor 100" (or HGCP reactor) was set at 15 Hz such that the rotation speed of the packed bed 102 was about 2000 rpm.

After precipitation, the suspension of Bicalutamide nanoparticles in admixture with the excipients was removed from the outlet conduit 106 of the HGCP reactor, pressure-filtered and washed with pure deionized water. The filter cake was then re-dispersed in 400 ml 5% (w/v) lactose water solution under homogenization and then spray dried using a Büchi™ mini spray dryer (B-290) to obtain nanodispersed Bicalutamide powder formulation. The spray drying conditions were set as follows: 1.5 mm nozzle; inlet temperature of the drying gas was 150° C.; atomizing rate was 600 L/hr; aspirator was set at 100%; and peristaltic pump rate was set at 10 ml/min.

The Bicalutamide nanoparticles in admixture with the excipients before and after spray drying were characterized using a FESEM and a DLS Particle Size Analyzer.

FESEM 2 mg of dry powder samples to be examined were mounted on aluminium sample studs using double-sized carbon tapes and sputtered coated with gold at 50 mA for 50 seconds. For suspension sample, the sample was dropped on to the copper grids for FESEM. The particle size and morphology were then observed using a field emission gun scanning electron microscope (FESEM) at 10 kV.

Figure 25A:
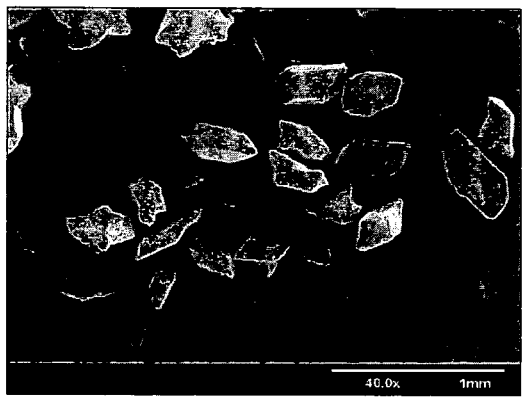
FIG. 25a and FIG. 25b are FESEM images at 40× and 300× magnification, respectively, of crystalline bicalutamide particles that were not made according to a disclosed embodiment.
Figure 25B:
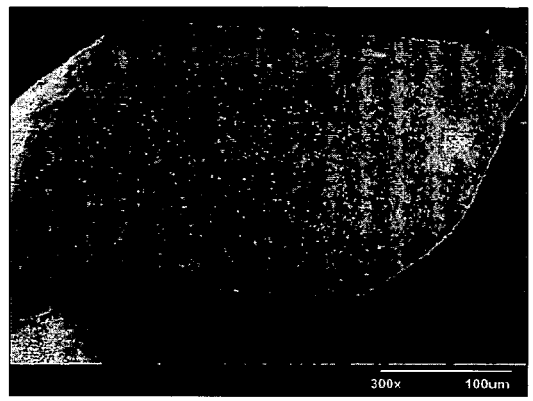

FIG. 25a and FIG. 25b are FESEM images at 40× and 300× magnification, respectively, of crystalline bicalutamide particles that were not made according to a disclosed embodiment.

Figure 26A:
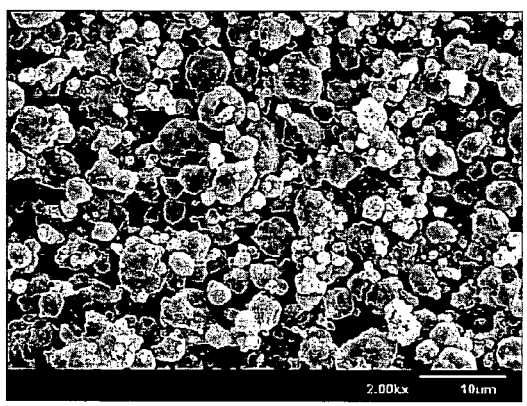
FIG. 26a and FIG. 26b are FESEM images at 2,000× and 10,000× magnification, respectively, of spray-dried powder bicalutamide nanoparticles that were made according to a disclosed embodiment.
Figure 26B:
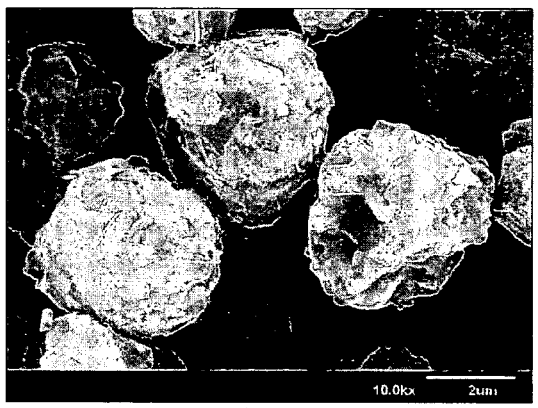

FIG. 26a and FIG. 26b are FESEM images at 2,000× and 10,000× magnification, respectively, of spray-dried powder bicalutamide nanoparticles that were made according to this Example. FIG. 26a and FIG. 26b show that the Bicalutamide nanoparticles and excipients formed spherical-shaped matrix particles after the spray drying step.

Figure 27A:
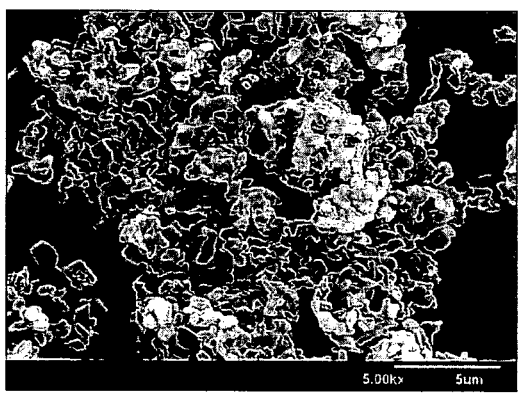
FIG. 27a and FIG. 27b are FESEM images at 5,000× and 20,000× magnification, respectively, of the powder bicalutamide nanoparticles of FIG. 26a and FIG. 26b, respectively, that are re-dispersed in water.
Figure 27B:
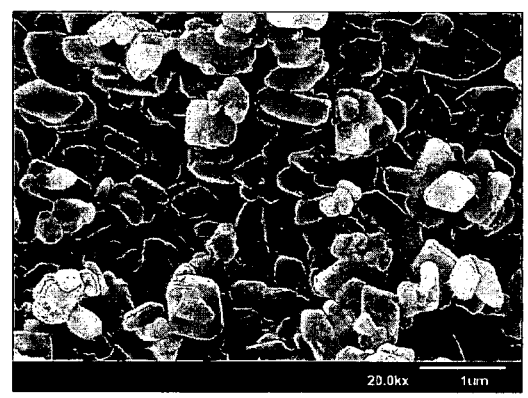

FIG. 27a and FIG. 27b are FESEM images at 5,000× and 20,000× magnification, respectively, of powder bicalutamide nanoparticles of FIG. 26a and FIG. 26b, respectively, that are re-dispersed in water. The Bicalutamide nanoparticles separate from the matrix particles and were suspended in the water solution.

DLS Particle Size Analyzer

Two samples were tested using the DLS Particle Size Analyzer. The first sample (Sample A) is an aliquot of the suspension of Bicalutamide nanoparticles in admixture with the excipients that was obtained after the precipitation step. The second sample (Sample B) is the redispersed powder spray dried Bicalutamide nanoparticles.

For Sample A, 0.2 ml of the suspension was diluted ten times with 2 ml of deionised water and the diluted sample was measured in a cuvette using DLS. For Sample B, 50 mg of the dried powder was ultrasonically dispersed in deionized water and sonicated for one minute. The dispersed particles were diluted 2 times and then measured in a cuvette using DLS. The results of this analysis are shown in Table 7 below.

TABLE 7

| Sample | Mean Size (μm) | $D_{10}$ (μm) | $D_{50}$ (μm) | $D_{90}$ (μm) |
| --- | --- | --- | --- | --- |
| Suspension after precipitation (A) | 0.6426 | 0.2606 | 0.4005 | 0.7466 |
| Powder redispersion in water (B) | 0.5852 | 0.3709 | 0.5582 | 0.8386 |

Table 7 shows that nanoparticulate of Bicalutamide drug formulation was obtained in this Example.

Example 6

Manufacture of Levodopa Nanoparticles

In this example, Levodopa nanoparticles are manufactured according to a disclosed process and according to the post-precipitation route 8c of FIG. 2. The process involves precipitating Levodopa nanoparticles from a precipitant solution, centrifuging the suspension of Levodopa drug nanoparticles and then spray-drying the isolated Levodopa nanoparticles.

During the precipitation step, a precipitant solution containing Levodopa was mixed with an anti-solvent solution under conditions of high shear and high gravity to form a suspension of Levodopa nanoparticles.

The precipitant solution was prepared by dissolving 10 g of Levodopa in 50 ml methanol and 5 ml of 37% concentrated hydrochloric acid mixture at room temperature (that is, about 20 to about 23.5° C.).

The anti-solvent solution used was made up by dissolving 4.5 ml of 2.5% ammonia solution in 300 ml isopropyl alcohol at room temperature (that is, about 20 to about 23.5° C.).

The precipitant solution and anti-solvent solution were introduced into the HGCP reactor 100" of FIG. 1c through liquid inlets 107a and 107b, respectively, to carry out high gravity controlled precipitation (HGCP). HGCP was carried out at room temperature, that is, at a temperature of about 20 to about 23.5° C. and at atmospheric pressure. The volumetric ratio of precipitant solution to anti-solvent solution was 1:10.

The frequency of motor of the HGCP reactor 100" (or HGCP reactor) was set at 15 Hz such that the rotation speed of the packed bed 102 was about 2000 rpm.

After precipitation, the suspension of Levodopa nanoparticles in admixture with the excipients was removed from the outlet conduit 106 of the HGCP reactor, centrifuged and washed with methanol. This process of washing was repeated twice, followed by centrifugation after each wash. The filter cake was then re-dispersed in 200 ml ethanol to form sample "Levo-1". In another sample, "Levo-2", 11 g of povidone was added to the ethanol under sonication for 2 minutes. Povidone was used as a polymer to encapsulate the drug nanoparticles and to retard the dissolution of the drug nanoparticles. The resultant suspension was spray dried using a Büchi™ mini spray dryer (B-290) to obtain nanodispersed Levodopa powder formulation.

The spray drying conditions were set as follows: 0.7 mm nozzle; inlet temperature of the drying gas was 120° C.; atomizing rate was 600 L/hr; aspirator was set at 100%; and peristaltic pump rate was set at 10 ml/min.

The Levodopa nanoparticles in admixture with the excipients before and after spray drying were characterized using a FESEM and a DLS Particle Size Analyzer.

FESEM 2 mg of dry powder samples to be examined were mounted on aluminium sample studs using double-sized carbon tapes and sputtered coated with gold at 50 mA for 50 seconds. For suspension sample, the sample was dropped on to the copper grids for FESEM. The particle size and morphology were then observed using a field emission gun scanning electron microscope (FESEM) at 10 kV.

Figure 28A:
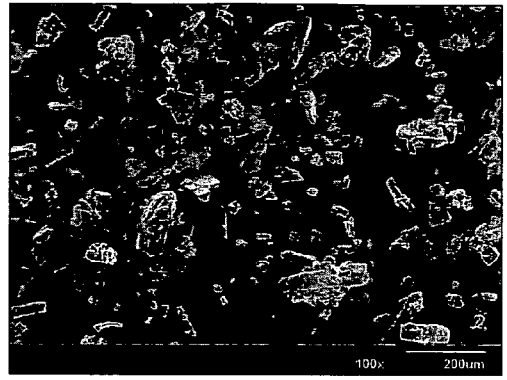
FIG. 28a and FIG. 28b are FESEM images at 100× and 1000× magnification, respectively, of crystalline levodopa particles that were not made according to a disclosed embodiment.
Figure 28B:
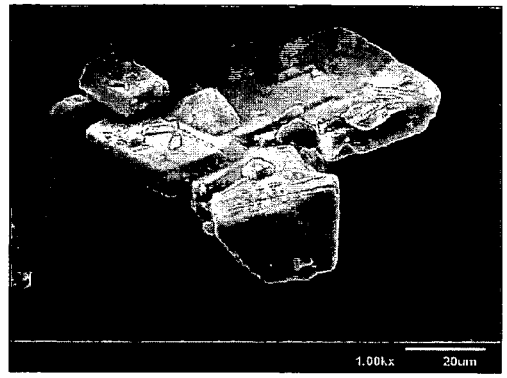

FIG. 28a and FIG. 28b are FESEM images at 100× and 1000× magnification, respectively, of crystalline Levodopa particles that were not made according to a disclosed embodiment.

Figure 29:
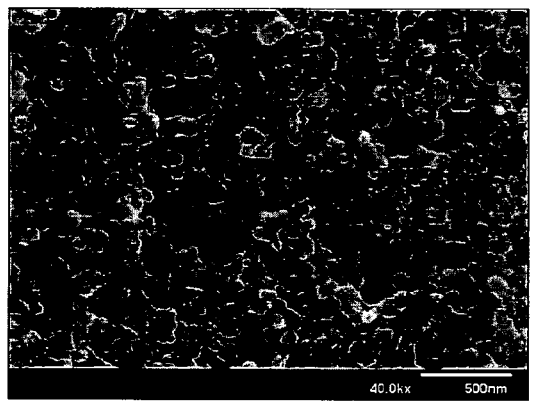
FIG. 29 is a FESEM image at 40,000× magnification of levodopa nanoparticles in suspension after the precipitation step.

FIG. 29 is a FESEM image at 40,000× magnification of levodopa nanoparticles in suspension after the precipitation step. This result is the same for both "Levo-1" and "Levo-2".

Figure 30A:
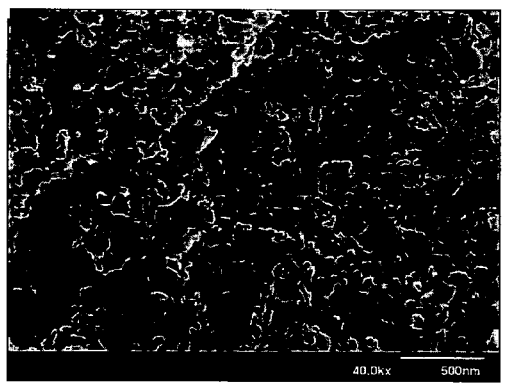
FIG. 30a and FIG. 30b are FESEM images at 40,000× and 2,000× magnification, respectively, of spray-dried powder levodopa nanoparticles that were made according to a disclosed embodiment.
Figure 30B:
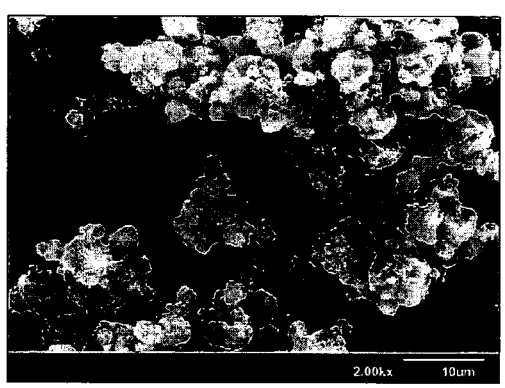

FIG. 30a and FIG. 30b are FESEM images at 40,000× and 2,000× magnification, respectively, of spray-dried powder levodopa nanoparticles that were made according to a disclosed embodiment. In FIG. 30b, the levodopa nanoparticles (Levo-2) are further provided in a povidone matrix with an irregular shape. It can be seen from FIG. 30a that the nano-sized Levodopa particles (Levo-1) aggregated together and cannot be redispersed as well as Levodopa particles provided with an excipient matrix (Levo-2). Hence, the excipient plays a role in keeping the drug particles nanodispersed within the matrix particles.

FIG. 31a and FIG. 31b are FESEM images at 20,000× and 30,000× magnification, respectively, of the powder levodopa nanoparticles of FIG. 30a and FIG. 30b, respectively, that are re-dispersed in methanol. Upon redispersion in methanol, the Levodopa nanoparticles separated from the matrix particles and were suspended in the methanol solution.

DLS Particle Size Analyzer

Three samples were tested using the DLS Particle Size Analyzer. The first sample (Sample A) is an aliquot of the suspension of precipitated Levodopa nanoparticles. The second sample (Sample B) is the redispersed spray dried powder Levodopa nanoparticles and povidone that were redispersed in methanol. The third sample (Sample C) is spray-dried powder pure levodopa nanoparticles that were redispersed in methanol (C).

For Sample A, 0.2 ml of the suspension was diluted ten times with 2 ml of deionised water and the diluted sample was measured in a cuvette using DLS. For Sample B and C, 50 mg of the dried powder was ultrasonically dispersed in 10 ml methanol and sonicated for one minute. The dispersed particles were diluted with methanol twice and then measured in a cuvette using DLS. The results of this analysis are shown in FIG. 32a, FIG. 32b and Table 8 below.

FIG. 32a and FIG. 32b are graphs of the particle size distribution of the samples.

TABLE 8

| Sample | Mean Size (μm) | $D_{10}$ (μm) | $D_{50}$ (μm) | $D_{90}$ (μm) |
| --- | --- | --- | --- | --- |
| Suspension after precipitation (A) | 0.0161 | 0.0118 | 0.0160 | 0.0207 |
| Powder redispersion in Methanol (with povidone) (B), Levo - 2 | 0.0167 | 0.0118 | 0.0166 | 0.0217 |
| Powder redispersion in Methanol (pure nanoparticles) (C), Levo - 1 | 4.9803 | 4.0749 | 5.0428 | 5.7976 |

FIG. 32b and Table 8 show that nanoparticulate of Levodopa drug formulation was obtained in this Example.

Example 7

Manufacture of Silybin Nanoparticles

In this example, silybin nanoparticles are manufactured according to a disclosed process and according to post-precipitation route 8a of FIG. 2. The process involves precipitating silybin nanoparticles from a precipitant solution and then spray-drying the silybin nanoparticles formed.

During the precipitation step, a precipitant solution containing silybin was mixed with an anti-solvent solution under micro-mixing environment to form a suspension of silybin nanoparticles in admixture with the excipients.

The precipitant solution was prepared by dissolving 10 g of silybin in 500 ml acetone at temperature of 25° C. The temperature of the solution was cooled down and maintained at 3° C.

The anti-solvent solution was prepared by dissolving 50 g of PVP, 0.2 g of SLS in 5000 ml water at a temperature of 25° C. The temperature of the solution was maintained at 3° C.

The precipitant solution and anti-solvent solution were introduced into the MMISM reactor 100' of FIG. 1b through liquid inlets 202 and 203, respectively, to carry out the precipitation. The precipitation was carried out at room temperature, that is, at a temperature of about 20 to about 23.5° C. and at atmospheric pressure. The volumetric ratio of precipitant solution to anti-solvent solution was 1:10.

The flow rate of the precipitant solution was set at 100 ml/min.

After precipitation, the suspension of silybin nanoparticles in admixture with the excipients was removed from the outlet conduit 106 of the MMISM reactor and immediately spray dried using the Büchi™ mini spray dryer 200 (B-290). The spray drying conditions were set as follows: 0.7 mm nozzle; inlet temperature of the drying gas was 140° C.; atomizing rate was 600 L/hr; aspirator was set at 100%; and peristaltic pump rate was set at 20 ml/min.

The resultant spray dried silybin nanoparticles in admixture with the excipients were removed from the collector of the spray dryer 200 in a powder form. The yield of the silybin nanoparticles before and after the spray-drying step is 100% and 90~100%, respectively.

The silybin nanoparticles in admixture with the excipients before and after spray drying were characterized using a FESEM.

FESEM

The samples to be examined were mounted on aluminium sample studs using double-sized carbon tapes and sputtered coated with gold at 50 mA for 50 seconds. The particle size and morphology were then observed using a field emission gun scanning electron microscope (FESEM) at 10 kV.

FIG. 33a is a FESEM image obtained at 5,000× magnification of micro-sized silybin that was not made according to a disclosed embodiment.

FIG. 33b is a FESEM image obtained at 5,000× magnification of spray-dried powder silybin that were made according to a disclosed embodiment.

Figure 33C:
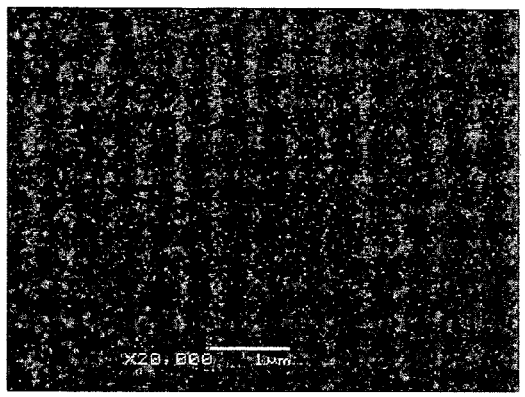
FIG. 33c is FESEM image obtained at 20,000× magnification of precipitated silybin nanoparticles.

FIG. 33c is a FESEM image at respective magnification at 20,000× of silybin nanoparticles in the suspension after the precipitation step. It can be seen from these figures that the silybin nanoparticles are in the nanometer range. The average particle size is about 70 nm.

Figure 33D:
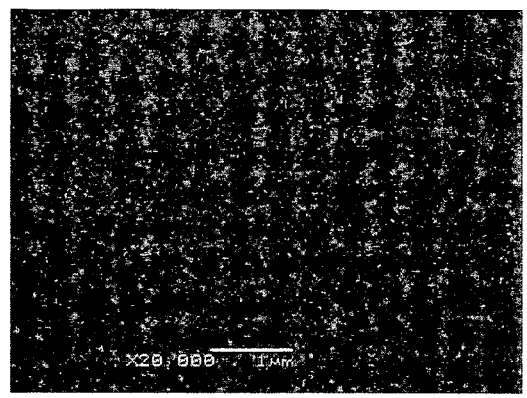
FIG. 33d is a FESEM image obtained at 20,000× magnification of the processed spray-dried powder silybin nanoparticles of FIG. 33b that were redispersed in water.

FIG. 33d is a FESEM image of spray-dried powder silybin nanoparticles that were redispersed in water. FIG. 33d was obtained at a magnification of 20,000×. FIG. 33d shows that upon redispersion in water, the silybin nanoparticles are discrete, individualised particles that are substantially separated from each other by an excipient-formed matrix.

Dissolution Characteristic Analysis

Three samples were analyzed for their inherent dissolution properties.

For each sample, 40 mg of silybin particles was added to 900 ml of USP simulated gastric fluid without enzymes (pH of 1.2) with 0.3% SLS as the dissolution medium. The temperature of the solution was maintained at 37° C. (±0.5° C.) to mimic the conditions in the stomach. The speed of the USP Dissolution Apparatus 2 (Paddle) was set at 50 rpm. At specific time intervals of 2.5 minutes, 5 minutes, 10 minutes, 15 minutes, 20 minutes, 30 minutes, 45 minutes and 60 minutes 120 minutes, a 5 ml aliquot was removed and filtered through a 0.22 μm syringe filter. The concentration of silybin in the dissolution medium was then determined by comparing the raw value to a known standard solution using a High Performance Liquid Chromatography (HPLC) from Shimadzu-Prominence HPLC System.

Figure 34:
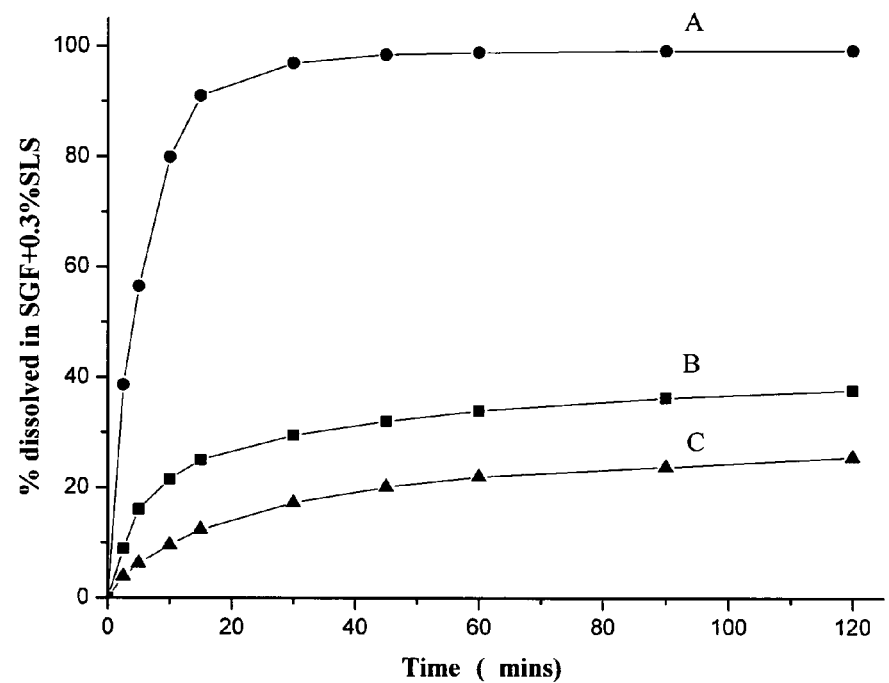
FIG. 34 shows the dissolution profiles of three silybin samples. Sample A refers to silybin particles that were made according to a disclosed embodiment. Sample B refers to spray dried micron-sized silybin particles that were physically mixed with excipients in water. Sample C refers to micron-sized silybin.

The result of this test is shown in FIG. 34, which is a graph showing the percentage of silybin dissolved in the dissolution medium as a function of time. Sample A refers to silybin particles that were made according to a disclosed embodiment. Sample B refers to spray dried micron-sized silybin particles that were physically mixed with excipients in water. Sample C refers to micron-sized silybin.

From FIG. 34, the advantage of nanoparticles of silybin can be seen in the dissolution test compared to the microparticles of silybin. The nanodispersed silybin powder sample made by a disclosed process has higher dissolution rate and extent compared to the micron-sized silybin powder sample in the discriminatory medium. Therefore, by using the disclosed process to make nanodispersed silybin powder sample that is suitable to be made into an oral solid dosage form, a greater amount of silybin will be available to a patient at a faster rate upon ingestion.

Example 8

Tablet Manufacture 1

Manufacturing Procedure: Wet Granulation

The fenofibrate tablets were manufactured according to the steps as shown below.

1. Weigh all the ingredients according to the formula in Table 9 below.
2. Sift intragranular excipients through ASTM 40 mesh s.s.seive; blend Fenofibrate Nanoparticulate granulate and intragranular excipients for 15 min in a blender (Inversina powder blender) and sift thrice through ASTM 40 mesh s.s.seive.
3. Dissolve binder in the water to make granulating liquid, knead step 2 blend with granulating liquid till granulation end point is achieved.
4. Dry the wet granules in the vacuum oven at 35° C. for 2 hrs or until the granules are dried.
5. Sift the granules through ASTM 20 mesh s.s.seive. Weigh the granules and calculate the yield.
6. Weigh the extra granular excipients and pass it through ASTM 40 mesh s.s.seive as per the yield of granules. Sift the lubricant through ASTM 60 mesh s.s.seive.
7. Blend lubricant with step 5 granules for 1 min in the bottle and put in the blender.
8. Accurately weigh the desired quantity of the lubricated blend.

9. Compress the blend using 18×9 mm oval biconcave punches on the rotary tablet press.

TABLE 9

| Tablet No. | Processed powder sample | Tablet making process | Excipients used in tablets | Weight of drug/ Weight of tablet |
|---|---|---|---|---|
| 71 | Feno-20080522* (37%-drug loading powder) | Wet-granulation | Lactose (50-90%), HPMC (1-5%), SLS (0.5-5%), Crospovidone (1-15%), SMCC (10-70%), Sodium-stearyl fumarate (0.5-5%) | 145 mg/ 630 mg |

*Fenofibrate was obtained from Example 1

Dissolution Characteristic Analysis

Three samples were analyzed here for their inherent dissolution properties. Feno-20080522 sample is processed fenofibrate drug powder that had been made according to Example 1. Feno Tab-71 sample had been made according to Table 9 above. Tricor 145 mg Fenofibrate tablet sample is a commercially available tablet sample that is used as a comparison sample.

For each sample, USP simulated gastric fluid without enzymes (pH 1.2) with 0.3% (w/w) SLS was used as the dissolution medium. The temperature of the solution was maintained at 37° C. (±0.5° C.). The speed of the USP Dissolution Apparatus 2 (Paddle) was set at 50 rpm. At specific time intervals of 2.5 minutes, 5 minutes, 10 minutes, 15 minutes, 20 minutes, 30 minutes, 45 minutes and 60 minutes, a 5 ml aliquot was removed and filtered through a 0.22 μm syringe filter. Then, the concentration of fenofibrate in the dissolution medium was determined by comparing the raw value (reference value) to a known standard solution using a High Performance Liquid Chromatography (HPLC).

Figure 35:
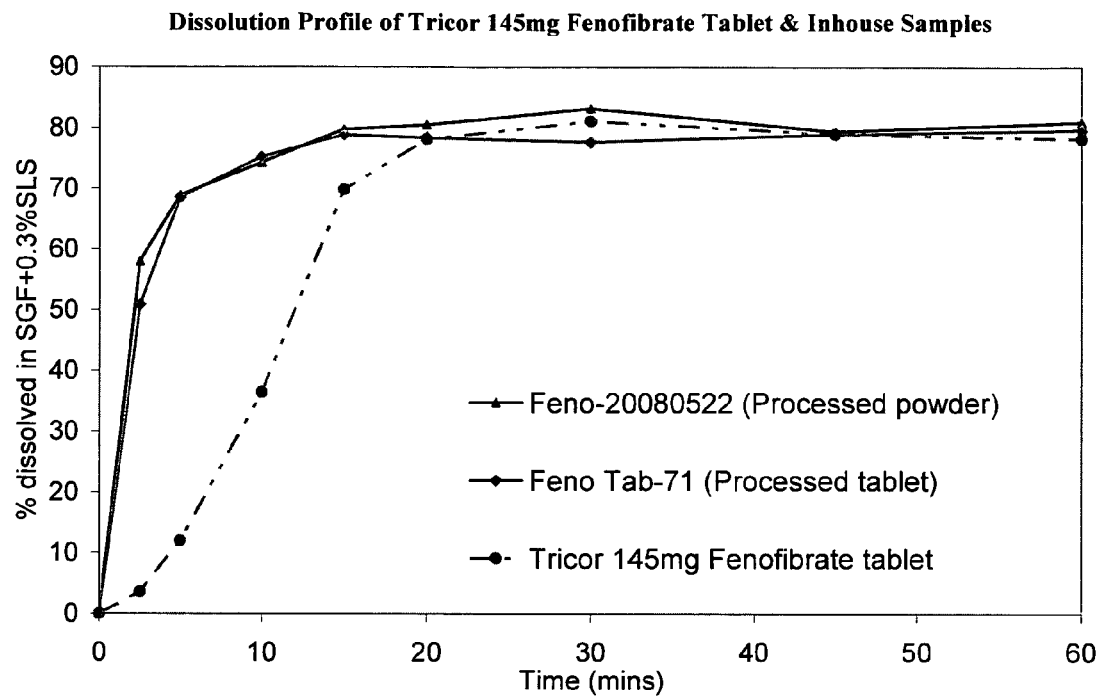
FIG. 35 shows the dissolution profiles of three fenofibrate samples. Feno-20080522 and Feno Tab-71 samples are formed according to the methodology of Example 8 below and the sample "Tricor 145 mg Fenofibrate tablet" is a reference tablet sample.

The result of this test is shown in FIG. 35, which is a graph showing the percentage of fenofibrate dissolved in the dissolution medium as a function of time. From FIG. 35, it can be seen that the nanoparticulate fenofibrate formulation produced in this Example has comparable dissolution extent as the reference sample.

Example 9

Tablet Manufacture 2

Manufacturing Procedure: Wet Granulation

The fenofibrate tablets were manufactured according to the steps as shown below for wet granulation.
1. Weigh all the ingredients according to the formula in Table 10 below.
2. Sift intragranular excipients through ASTM 40 mesh s.s.seive; blend Fenofibrate Nanoparticulate granulate and intragranular excipients for 15 min in a blender (Inversina powder blender) and sift thrice through ASTM 40 mesh s.s.seive.
3. Dissolve binder in the water to make granulating liquid, knead step 2 blend with granulating liquid until granulation end point is achieved.
4. Dry the wet granules in the vacuum oven at 35° C. for 2 hrs or until the granules are dried.
5. Sift the granules through ASTM 20 mesh s.s.seive. Weigh the granules and calculate the yield.
6. Weigh the extra granular excipients and pass it through ASTM 40 mesh s.s.seive as per the yield of granules. Sift the lubricant through ASTM 60 mesh s.s.seive.
7. Blend lubricant with step 5 granules for 1 min in the bottle and put in the blender.
8. Accurately weigh the desired quantity of the lubricated blend.
9. Compress the blend using 18×9 mm oval biconcave punches on the rotary tablet press.

Manufacturing Procedure: Direct Compression

The fenofibrate tablets were manufactured according to the steps as shown below for direct compression.
1. Weigh all the ingredients according to the formula in Table 10 below. Sift excipients through ASTM 40 mesh except the lubricant.
2. Add the excipients to the Fenofibrate granulate and mix in the blender (Inversina powder blender) for 10 min.
3. Sift the lubricant sodium stearyl fumarate through ASTM 60 mesh s.s.seive.
4. Blend lubricant with step 2 blend for 2 min in the blender.
5. Accurately weigh the desired quantity of the lubricated blend.
6. Compress the blend using 18×9 mm oval biconcave punches on the rotary tablet press.

TABLE 10

| Tablet No. | Processed powder sample | Tablet making process | Excipients used in tablets | Weight of drug/ Weight of tablet |
|---|---|---|---|---|
| 71D | Feno-20080522 (37%-drug loading) | Wet-granulation | Lactose (50-90%), HPMC (1-5%), SLS (0.5-5%), Crospovidone (1-15%), SMCC (10-70%), Sodium stearyl fumarate (0.5-5%) | 145 mg/ 630 mg |
| 77C | Feno-20080522 (37%-drug loading) | Powder direct compression | | |
| 77D | Feno-20080529 (31%-drug loading) | Powder direct compression | | |

Dissolution Characteristic Analysis

Five samples were analyzed here for their inherent dissolution properties. Feno-20080522 sample (with 37% drug loading) is processed fenofibrate drug powder that had been made according to Example 1. Feno Tab-77C sample had been made according to Table 10 above. Feno Tab-71D sample had been made according to Table 10 above. Feno Tab-77D sample had been made according to Table 10 above. Tricor 145 mg Fenofibrate tablet sample is a commercially available tablet sample that is used as a comparison sample.

For each sample, USP simulated gastric fluid without enzymes (pH 1.2) with 0.3% (w/w) SLS was used as the dissolution medium. The temperature of the solution was maintained at 37° C. (±0.5° C.). The speed of the USP Dissolution Apparatus 2 (Paddle) was set at 50 rpm. At specific time intervals of 2.5 minutes, 5 minutes, 10 minutes, 15 minutes, 20 minutes, 30 minutes, 45 minutes and 60 minutes, a 5 ml aliquot was removed and filtered through a 0.22 μm syringe filter. Then, the concentration of fenofibrate in the dissolution medium was determined by comparing the raw value to a known standard solution using a High Performance Liquid Chromatography (HPLC).

Figure 36:
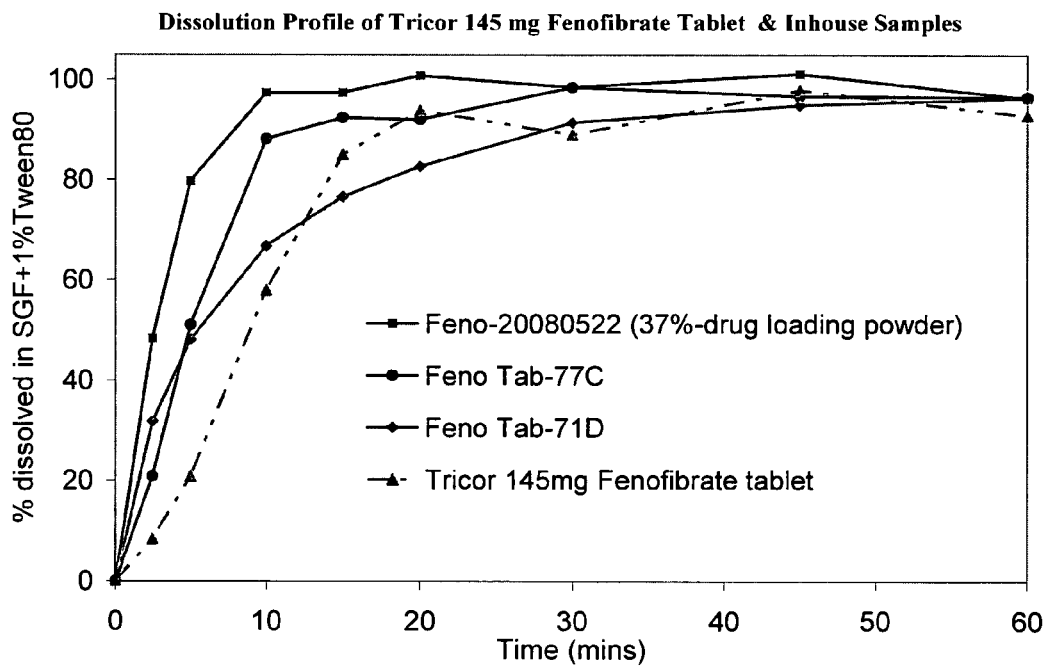
FIG. 36 shows the dissolution profiles of four fenofibrate samples. Feno-20080522, Feno Tab-77C and Feno Tab-71D samples are formed according to the methodology of Example 9 below and the sample "Tricor tablet 145 mg" is a reference tablet sample.
Figure 37:
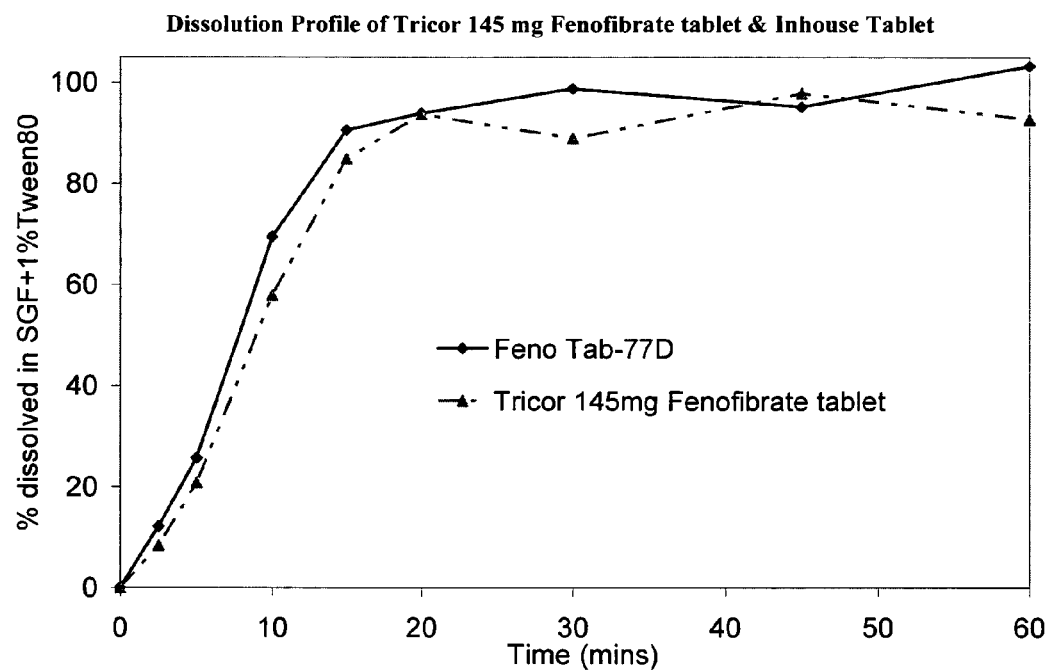
FIG. 37 shows the dissolution profiles of two fenofibrate samples. Feno Tab-77D sample is formed according to the methodology of Example 9 below and the sample "Tricor tablet 145 mg" is a reference tablet sample.

The results of this test are shown in FIG. 36 and FIG. 37, which are graphs showing the percentage of fenofibrate dissolved in the dissolution medium as a function of time. From FIG. 36 and FIG. 37, it can be seen that the nanoparticulate fenofibrate formulation produced in this Example has comparable dissolution effect as the reference sample.

Comparative Example

Micromixing Vs Normal Mixing

To validate the superiority of micro-mixing precipitation to normal mixing, fenofibrate powders are prepared according to different mixing ways. Micro-mixing precipitation can be performed in two ways, one is using the HGCP reactor as in example 1 and the other is using a multiple micro-channels impinging stream mixer (MMISM). Therefore, fenofibrate nanoparticles are manufactured according to example 1 except that the precipitation is performed in MMISM rather than in HGCP reactor. For the normal mixing comparative test, fenofibrate particles are manufactured according to Example 1, except that the precipitation step under the micromixing environment of Example 1 is replaced by normal mixing. Here, the precipitant solution containing fenofibrate (200 ml) was mixed with the anti-solvent solution (2000 ml) at magnetic stirring 1250 rpm to form a suspension of fenofibrate particles in admixture with the excipients. The composition of the fenofibrate powder was similar to that in Table 2.

FESEM, DLS, DSC and dissolution tests were performed according to the same conditions to Example 1.

FESEM

Figure 38A:
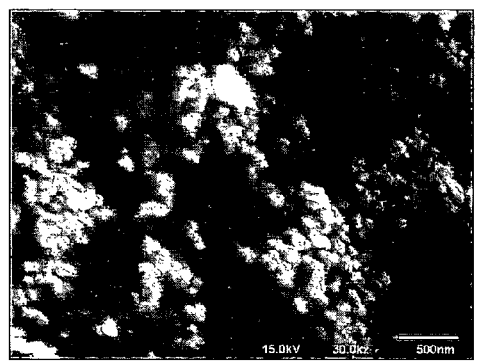
FIG. 38a is FESEM image at 30,000× magnification of fenofibrate particles made from MMISM in the comparative example.
Figure 38B:
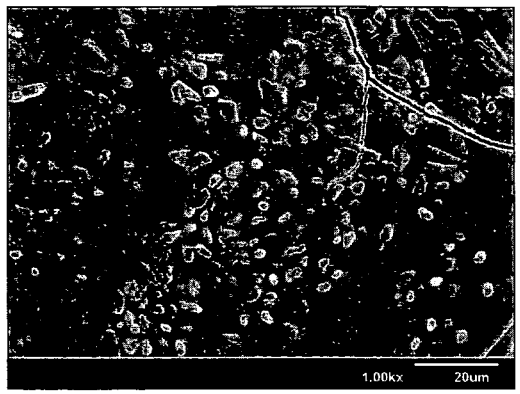
FIG. 38b and FIG. 38c are FESEM images at 1000× magnification of fenofibrate particles made from normal mixing in the Comparative Example.
Figure 38C:
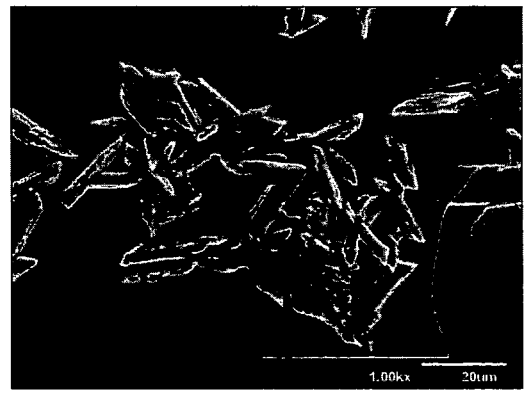

FIG. 38a is a FESEM image at 30000× magnification of fenofibrate nanoparticles made from MMISM. FIG. 38b and FIG. 38c are FESEM images at 1000× magnification of fenofibrate particles in the suspension after immediate precipitation by normal mixing and after stirring for 30 minutes. As compared to FIG. 4a and FIG. 4b of the fenofibrate particles of Example 1, the fenofibrate particles obtained from micro-mixing precipitation are in nanometer range while particles from normal mixing are in the micro-sized range and grow bigger rapidly during stirring.

Figure 39A:
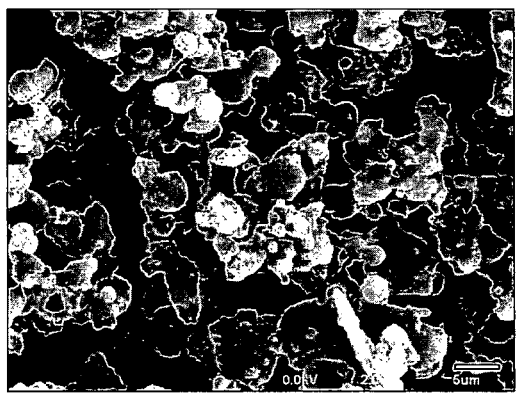
FIG. 39a is a FESEM image of spray dried fenofibrate powder from MMISM in the Comparative Example at 2000× magnification.
Figure 40A:
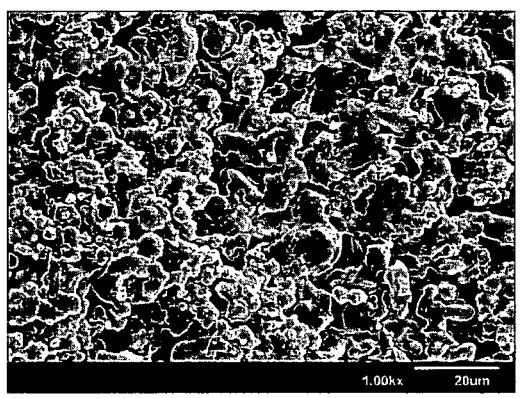
FIG. 40a is a FESEM image of spray dried fenofibrate powder from normal mixing in the Comparative Example at 1000× magnification.

FIG. 39a is a FESEM image at 2000× magnification of spray dried fenofibrate powders using MMISM according to example 1. FIG. 40a is a FESEM image at 1000× magnification of spray dried fenofibrate powders using normal mixing according to this comparative example. As seen in FIG. 39a and FIG. 40a, most fenofibrate powders from MMISM are spherical with smooth surface, which are almost the same as those in FIG. 5a in example 1. However, many powders from normal mixing are in irregular shape. Rod-shaped fenofibrate particles of several microns can be observed in the powders. This is probably caused by fenofibrate drug particles of different sizes. Smaller particles obtained from micro-mixing may be dispersed well in excipient matrix during spray drying and might not influence matrix powder shape while big drug particles from normal mixing can not be encapsulated by excipient matrix efficiently and appear in powders alone.

Figure 39B:
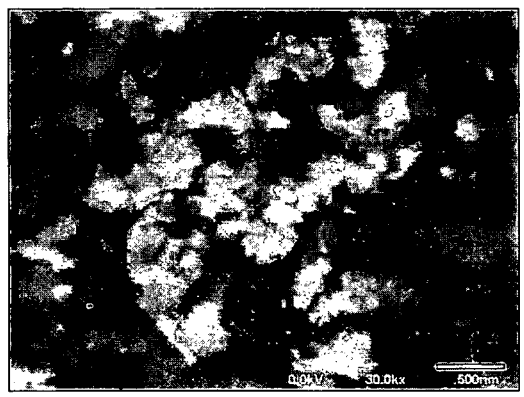
FIG. 39b is a FESEM image at 30000× magnification of the fenofibrate powder of FIG. 39a after being redispersed in water.
Figure 40B:
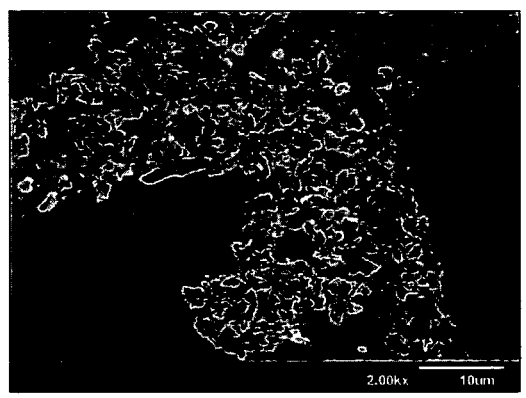
FIG. 40b is a FESEM image at 2000× magnification of the fenofibrate powder of FIG. 40a after being redispersed in water.

FIG. 39b is a FESEM image at 30000× magnification of the fenofibrate particles of FIG. 39a being redispersed in water. FIG. 40b is a FESEM image at 2000× magnification of the fenofibrate particles of FIG. 40a being redispersed in water. In comparing with example 1 in FIG. 5b, the fenofibrate particles using MMISM are in the nano-sized range, which are smaller than those using normal mixing. That is, micromixing precipitation is better than normal mixing to produce smaller particles and MMISM is equivalent to HGCP reactor to obtain fenofibrate nanoparticles.

DLS Particle Size Analyzer

Figure 41:
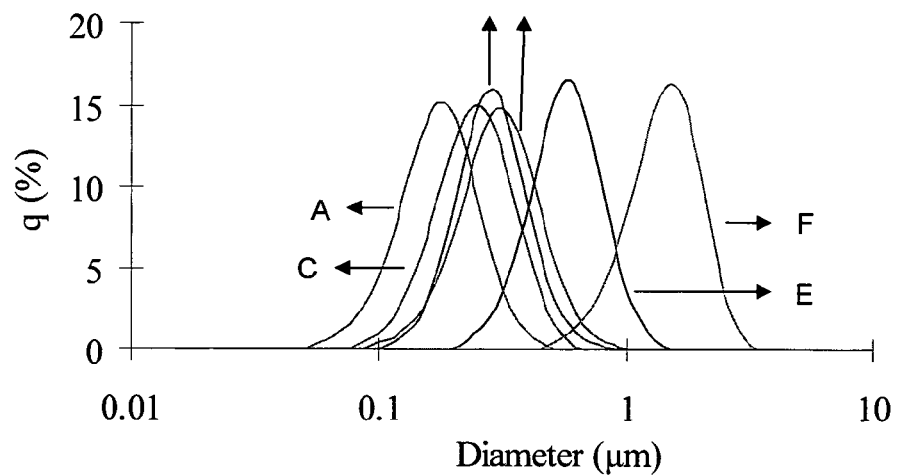
FIG. 41 is a comparison of the particle size distribution of fenofibrate nanoparticles from Example 1, the nanoparticles from MMISM and the particles from normal mixing in Comparative Example.

FIG. 41 shows the particle size distribution of fenofibrate nanoparticles among Example 1 (Samples A and B), nanoparticles obtained using MMISM (Samples C and D) and particles obtained using normal mixing (Samples E and F). Samples A and B were obtained from Example 1. Sample C is the suspension of fenofibrate nanoparticles precipitated from MMISM in the comparative example. Sample D is the powder redispersion of fenofibrate nanoparticles from MMISM. Sample E is the suspension of fenofibrate particles during precipitation step with excipients at 2L scale by normal mixing in the comparative example. Sample F is the powder redispersion of fenofibrate particles in the comparative example.

It can be seen that the mean diameter of fenofibrate particles using normal mixing is bigger than those obtained from Example 1 and example using MMISM which were manufactured according to the present process.

DSC Analysis

Figure 42A:
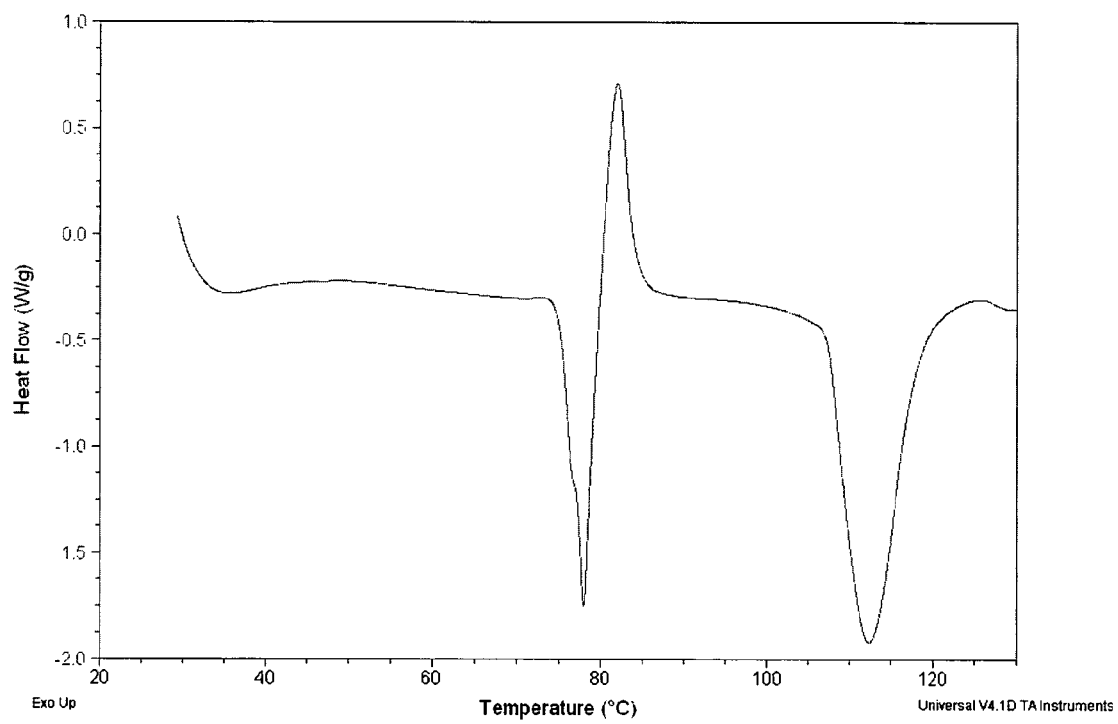
FIGS. 42a and 42b are DSC profiles of the fenofibrate particle powder from MMISM and normal mixing respectively in the Comparative Example.
Figure 42B:
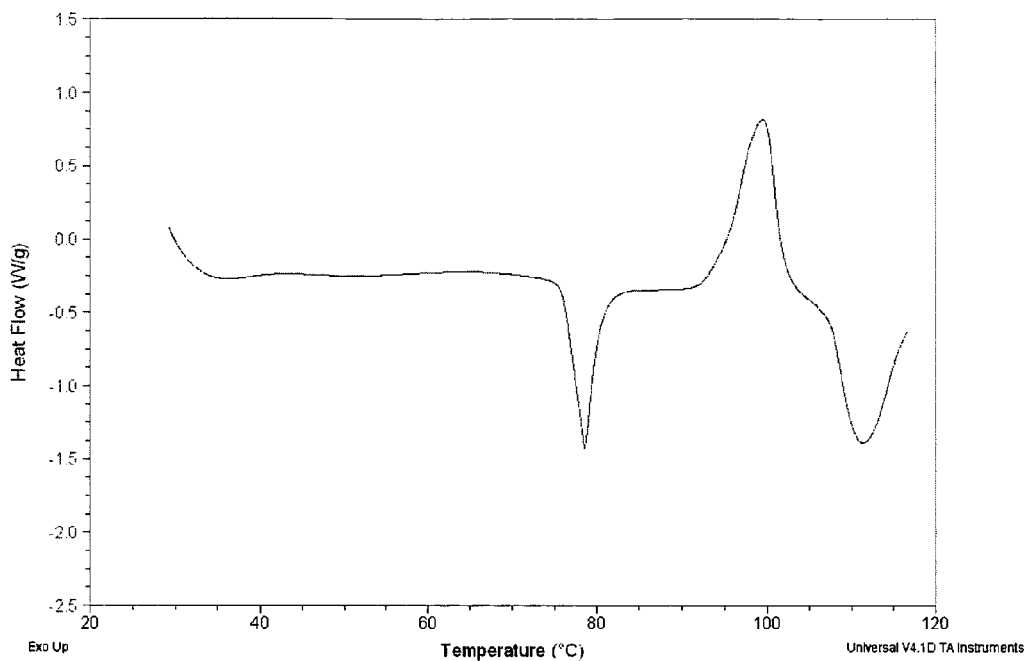

FIG. 42a is a DSC profile of the fenofibrate particles obtained from MMISM and FIG. 42b for fenofibrate particles obtained from normal mixing, both showing that the fenofibrate particles are crystalline.

Dissolution Characteristic Analysis

Figure 43:
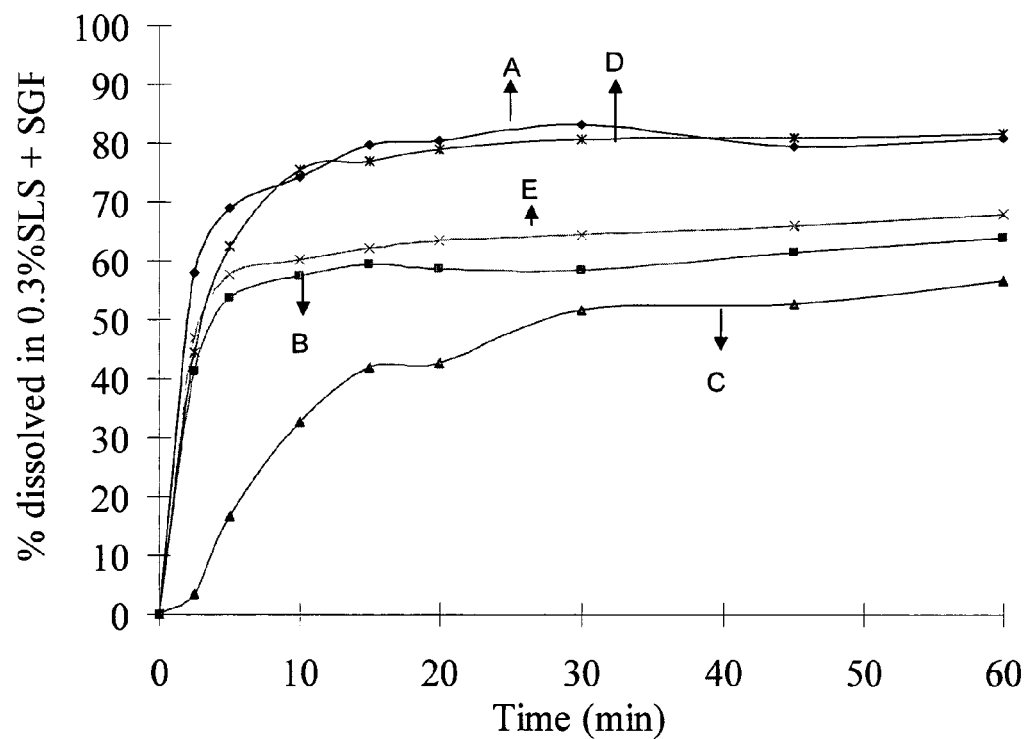
FIG. 43 shows the dissolution profiles of five fenofibrate samples. Samples A to C are the same samples as Samples A to C of FIG. 9 and Sample D is the dissolution profile of the fenofibrate particle powder from MMISM in the Comparative Example. Sample E is the dissolution profile of fenofibrate powder from normal mixing in the comparative example.

FIG. 43 is the dissolution profiles of five fenofibrate samples as a function of time. Samples A to C are the same samples as those shown in FIG. 9 of Example 1. Sample D is the fenofibrate particle powder obtained using MMISM. Sample E is the fenofibrate powder obtained using normal mixing in the comparative example. The dissolution profile of sample D is almost the same as that of sample A from example 1. The dissolution profile of Sample E is similar to that of Sample B, which are spray dried micro-sized fenofibrate particles. Based on particle size test results, sample A and sample D form suspension of fenofibrate nanoparticles during redispersion, which are slightly bigger than those during precipitation, and therefore dissolve faster than fenofibrate particles of samples B, C and E which are micron-sized. As the fenofibrate particles from precipitation via normal mixing are bigger than those nanoparticles obtained by micro-mixing (Sample A and D) in the disclosed process and grow bigger rapidly into microparticles during spray drying, the powder of sample E shows the dissolution characteristic of microparticles rather than nanoparticles. The key of fast and high dissolution is the drug particle size in the matrix powder rather than matrix powder size. Therefore, the disclosed process to prepare nanoparticles ensures the small particle size and narrow size distribution and prevents significant growth of drug particle size during powder formation step. Such powder can be easily redispersed in water to form suspension in which drug particle size is similar to or slightly higher than that in the slurry in the precipitation step. The disclosed process is also easy to scale-up and can be a continuous process, with minimal down-time.

Applications

The disclosed process may be capable of being scaled up to an industrial scale. The disclosed process may result in savings in time and cost due to the rapid nature of the process.

The disclosed process may be used to make nanoparticles of poorly-soluble drugs that have a narrow particle size distribution.

The disclosed process may be used to make solid oral dosage forms of drugs that are typically known to be poorly-soluble drugs. The formulations made from a disclosed process may have a substantially high dissolution rate and dissolution extent as compared to other formulations that are not made from the disclosed process. The formulations may have a high level of bioavailability in the body upon ingestion. The formulations may be suitable for oral administration to a mammal in need thereof.

In the disclosed process, the polymorphic form of a drug may be modulated depending on the process conditions and nature of the drug. Accordingly, depending on the type of post-precipitation route used, the polymorphic form of the drug may change such that the polymorphic form of the end product is different from that of the starting product.

The disclosed process may aid in changing the morphology of a drug. This may be achieved by altering the process conditions such that drug particles of different shapes may be generated, which may affect the type of oral dosage form used.

In the disclosed process, introduction of impurities into the process is substantially minimized due to the type of process units used. This is in comparison to conventional processes such as milling, which introduces impurity into the drug product due to corrosion and grinding.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A process for making excipient matrix particles for delivery of drug nanoparticles, the process comprising the steps of:
   a. forming a suspension of drug nanoparticles by mixing a precipitant solution with an anti-solvent solution under micro-mixing environment, where said formed drug nanoparticles have a narrow particle size distribution;
   b. providing an excipient to at least one of said precipitant solution, said anti-solvent solution and said suspension of drug nanoparticles, said excipient being selected to maintain said drug nanoparticles in a dispersed state when in liquid form; and
   c. drying said suspension of drug nanoparticles containing said excipient therein in a spray dryer to remove solvent therefrom so that said drug nanoparticles are substantially individualized and surrounded or encapsulated by said excipient, wherein the spray dryer has an inlet temperature of drying gas in a range of 110-220° C, an outlet temperature in a range of 20-80° C, and a drying time of less than about 10 seconds, wherein removal of said solvent causes said excipient to solidify and thereby form micro-sized matrix particles with dimension of 1μm to 10μm, each micro-sized matrix particle being comprised of said drug nanoparticles dispersed in a solid matrix of said excipient.

2. The process according to claim 1, further comprising the step of:
   d. aging said formed suspension of drug nanoparticles.

3. The process according to claim 1, further comprising the step steps of:
   e. isolating said formed drug nanoparticles from said suspension, wherein said isolating step is carried out by centrifuging or filtering said suspension;
   f. washing said isolated formed drug nanoparticles; and
   g. suspending said washed drug nanoparticles in a redispersion solvent that contains the excipient.

4. The process according to claim 1, wherein said drug is selected from the group consisting of an analgesic drug, an anti-inflammatory drug, an antianginal, an anti-arrhythmic drug, an antibacterial agent, an antiprotozoal agent, an anticoagulant, an antidepressant, an anti-diabetic drug, an antiepileptic drug, an antifungal agent, an antihistamine, an antihypertensive drug, an anti-muscarinic agent, an antineoplastic agent, an anti-migraine drug, an anti-parasitic agent, an anti-Parkinsonian drug, an antipsychotic agent, a hypnotic agent, a sedating agent, an anti-stroke agent, an anti-thrombotic agent, an antitussive, an antiviral, a beta-adrenoceptor blocking agent, a calcium channel blocker, a cardiac inotropic agent, a contraceptive agent, a corticosteroid, a dermatological agent, a disinfectant, a diuretic, a gastro-intestinal agent, a general anaesthetic, a haemostatic, a local anaesthetic, an opioid analgesic, a parasympathomimetic, a peptide, a sex hormone, a steroid, a stimulating agent, a vasodilator, the N-oxides thereof, the pharmaceutically acceptable acid or base addition salts thereof and the stereochemically isomeric forms thereof.

5. The process according to claim 4, wherein said drug is selected from the group consisting of fenofibrate, Lopinavir, cefuroxime axetil, cyclosporine, silybin, megestrol acetate, azithromycin, Bicalutamide and Levodopa.

6. The process according to claim 1, wherein said excipient is selected from the group consisting of a diluent, a surfactant and a disintegrant.

7. The process according to claim 6, wherein said excipient is selected from the group consisting of hydroxypropylmethylcellulose, sodium lauryl sulfate, lactose, mannitol, sucrose, silicified microcrystalline cellulose and crosslinked polyvinyl pyrrolidone.

8. The process according to claim 1, wherein said micro-mixing environment is generated by a high impingement force.

9. The process according to claim 1, wherein said micro-mixing environment is generated by a high shear force.

10. The process according to claim 9, wherein said high shear force is generated at a high gravity level.

11. The process according to claim 1, wherein the amount of excipient provided in said matrix particle is in the range of 0.1 wt % to 90 wt % based on the weight of said matrix particle.

12. The process according to claim 1, wherein the amount of drug nanoparticles dispersed within said matrix particle is in the range of 5 wt % to 90 wt % based on the weight of said matrix particle.

13. A continuous process for making particles for delivery of drug nanoparticles, the process comprising the steps of:
   a. forming a suspension of drug nanoparticles by mixing a precipitant solution with an anti-solvent solution under micro-mixing environment, where said formed nanoparticles have a narrow particle size distribution, and wherein at least one of said precipitant solution and said anti-solvent solution comprises an excipient therein, said excipient being selected to maintain said drug nanoparticles in a dispersed state when in liquid form; and
   b. drying said suspension of drug nanoparticles containing said excipient therein in a spray dryer to remove solvent therefrom so that said drug nanoparticles are substantially individualized and surrounded or encapsulated by said excipient, wherein the spray dryer has an inlet temperature of drying gas in a range of 110-220° C, an outlet temperature in a range of 20-80° C, and a drying time of less than about 10 seconds, wherein removal of said solvent causes said excipient to solidify and thereby form micro-sized matrix particles with dimension of 1 μm to 10 μm, each micro-sized matrix particle being comprised of said drug nanoparticles dispersed in a solid matrix of said excipient, with the proviso that said process does not comprise an aging step.

14. A process for making particles for delivery of drug nanoparticles, the process comprising the steps of:
   a. forming a suspension of drug nanoparticles by mixing a precipitant solution with an anti-solvent solution under micro-mixing environment, where said formed nanoparticles have a narrow particle size distribution;
   b. aging said formed suspension of drug nanoparticles for a period of time sufficient to alter the polymorphic form of said drug;
   c. isolating said drug nanoparticles from said suspension;
   d washing said isolated drug nanoparticles to substantially remove solvent therefrom;
   e. adding said washed drug nanoparticles to an aqueous solvent having an excipient therein to thereby form a second suspension of drug nanoparticles, said excipient being selected to maintain said drug nanoparticles in a dispersed state when in liquid form; and
   f. drying said suspension of drug nanoparticles containing said excipient therein in a spray dryer to remove solvent therefrom so that said drug nanoparticles are substantially individualized and surrounded or encapsulated by said excipient, wherein the spray dryer has an inlet temperature of drying gas in a range of 110-220° C, an outlet temperature in a range of 20-80° C, and a drying time of less than about 10 seconds, wherein removal of said solvent causes said excipient to solidify and thereby form micro-sized matrix particles with dimension of 1 µm to 10 µm, each micro-sized matrix particle being comprised of said drug nanoparticles dispersed in a solid matrix of said excipient.

15. A process for making particles for delivery of drug nanoparticles, the process comprising the steps of:
   a. forming a suspension of drug nanoparticles by mixing a precipitant solution with an anti-solvent solution under micro-mixing environment, where said formed nanoparticles have a narrow particle size distribution;
   b. isolating said drug nanoparticles from said suspension;
   c. washing said isolated drug nanoparticles to substantially remove solvent therefrom;
   d. adding said washed drug nanoparticles to an aqueous solvent having an excipient therein to thereby form a second suspension of drug nanoparticles, said excipient being selected to maintain said drug nanoparticles in a dispersed state when in liquid form; and
   e. drying said suspension of drug nanoparticles containing said excipient therein in a spray dryer to remove solvent therefrom so that said drug nanoparticles are substantially individualized and surrounded or encapsulated by said excipient, wherein the spray dryer has an inlet temperature of drying gas in a range of 110-220° C, an outlet temperature in a range of 20-80° C, and a drying time of less than about 10 seconds, wherein removal of said solvent causes said excipient to solidify and thereby form micro-sized matrix particles with dimension of 1 µm to 10 µm, each micro-sized matrix particle being comprised of said drug nanoparticles dispersed in a solid matrix of said excipient.

\* \* \* \* \*